(12) United States Patent
Thanos et al.

(10) Patent No.: US 11,471,398 B2
(45) Date of Patent: Oct. 18, 2022

(54) DEVICES AND METHODS FOR DELIVERING THERAPEUTICS

(71) Applicant: Vertex Pharmaceuticals Incorporated, Boston, MA (US)

(72) Inventors: Christopher Thanos, Cumberland, RI (US); Yang Qui, Providence, RI (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 16/294,631

(22) Filed: Mar. 6, 2019

(65) Prior Publication Data

US 2019/0201323 A1    Jul. 4, 2019

Related U.S. Application Data

(63) Continuation of application No. PCT/US2018/037637, filed on Jun. 14, 2018.

(60) Provisional application No. 62/519,702, filed on Jun. 14, 2017.

(51) Int. Cl.
| | |
|---|---|
| *A61M 31/00* | (2006.01) |
| *A61K 9/00* | (2006.01) |
| *A61K 35/39* | (2015.01) |
| *A61K 38/43* | (2006.01) |
| *A61K 38/18* | (2006.01) |
| *A61K 9/70* | (2006.01) |
| *C12N 5/071* | (2010.01) |

(52) U.S. Cl.
CPC .............. *A61K 9/00* (2013.01); *A61K 9/0024* (2013.01); *A61K 9/7007* (2013.01); *A61K 35/39* (2013.01); *A61K 38/18* (2013.01); *A61K 38/43* (2013.01); *A61M 31/002* (2013.01); *C12N 5/0676* (2013.01); *C12N 5/0678* (2013.01); *C12N 5/0613* (2013.01); *C12N 2537/10* (2013.01)

(58) Field of Classification Search
None
See application file for complete search history.

(56) References Cited

U.S. PATENT DOCUMENTS

| | | |
|---|---|---|
| 670,317 A | 3/1901 | Friedlaender |
| 798,204 A | 8/1905 | Nelson |
| 2,984,599 A | 5/1961 | Edwards et al. |
| 5,066,397 A | 11/1991 | Muto et al. |
| 5,320,512 A | 6/1994 | Moore et al. |
| 5,814,020 A | 9/1998 | Gross |
| 5,997,900 A | 12/1999 | Wang et al. |
| 7,033,831 B2 | 4/2006 | Fisk et al. |
| 7,407,703 B2 | 8/2008 | Deyoung et al. |
| 7,985,585 B2 | 7/2011 | D'Amour et al. |
| 7,993,916 B2 | 8/2011 | Agulnick et al. |
| 7,993,920 B2 | 8/2011 | Martinson et al. |
| 8,129,182 B2 | 3/2012 | D'Amour et al. |
| 8,153,429 B2 | 4/2012 | Robins et al. |
| 8,187,878 B2 | 5/2012 | Dalton et al. |
| 8,211,699 B2 | 7/2012 | Robins et al. |
| 8,216,836 B2 | 7/2012 | D'Amour et al. |
| 8,278,106 B2 | 10/2012 | Martinson et al. |
| 8,334,138 B2 | 12/2012 | Robins et al. |
| 8,338,170 B2 | 12/2012 | Kelly et al. |
| 8,415,158 B2 | 4/2013 | Robins et al. |
| 8,425,928 B2 | 4/2013 | Martinson et al. |
| 8,445,273 B2 | 5/2013 | Green et al. |
| 8,574,905 B2 | 11/2013 | D'Amour et al. |
| 8,586,357 B2 | 11/2013 | D'Amour et al. |
| 8,603,811 B2 | 12/2013 | D'Amour et al. |
| 8,623,645 B2 | 1/2014 | D'Amour et al. |
| 8,623,650 B2 | 1/2014 | Robins et al. |
| 8,633,024 B2 | 1/2014 | D'Amour et al. |
| 8,647,873 B2 | 2/2014 | D'Amour et al. |
| 8,658,151 B2 | 2/2014 | Kelly et al. |
| 8,658,352 B2 | 2/2014 | Robins et al. |
| 8,895,300 B2 | 11/2014 | Schulz |
| 9,045,736 B2 | 6/2015 | Kelly et al. |
| 9,132,226 B2 | 9/2015 | Martinson et al. |
| 9,222,069 B2 | 12/2015 | D'Amour et al. |
| 9,267,110 B2 | 2/2016 | Robins et al. |
| 9,433,557 B2 | 9/2016 | Green et al. |
| 9,499,795 B2 | 11/2016 | D'Amour et al. |
| 9,506,034 B2 | 11/2016 | Kelly et al. |
| 9,526,880 B2 | 12/2016 | So et al. |
| 9,585,917 B2 | 3/2017 | Martinson et al. |
| 9,605,243 B2 | 3/2017 | D'Amour et al. |
| 9,732,318 B2 | 8/2017 | D'Amour et al. |
| 9,764,062 B2 | 9/2017 | Martinson et al. |
| 9,913,930 B2 | 3/2018 | Martinson et al. |
| 10,087,413 B2 | 10/2018 | Desai et al. |
| 10,138,463 B2 | 11/2018 | Schulz |

(Continued)

FOREIGN PATENT DOCUMENTS

| | | |
|---|---|---|
| DE | 102007006634 A1 | 8/2008 |
| EP | 2377922 A3 | 5/2013 |

(Continued)

OTHER PUBLICATIONS

Thanos et al., Expert Opin. Biol. Ther (2009), vol. 9 No. 1, pp. 29-44.*
Hall et al., Acta Biomater. Feb. 2011; 7(2): 614-624.*
Vernon et al., Journal of Biomaterials Science, Polymer Edition, vol. 10, No. 2, pp. 183-198 (1999).*
An et al Biomaterials (2015) vol. 37, pp. 40-48 (Year: 2015).*
Barkai et al., World Journal of Transplantation, Mar. 24, 2016: 6(1): 69-90 (Year: 2016).*

(Continued)

*Primary Examiner* — Evelyn Y Pyla

(74) *Attorney, Agent, or Firm* — Wolf, Greenfield & Sacks, P.C

(57) ABSTRACT

The present invention provides devices and methods for delivering a population of cells or a therapeutic agent to a subject in need thereof.

36 Claims, 11 Drawing Sheets

(56) References Cited

U.S. PATENT DOCUMENTS

| | | |
|---|---|---|
| 10,172,791 B2 | 1/2019 | Ma et al. |
| 10,272,179 B2 | 4/2019 | Martinson et al. |
| 2002/0098559 A1 | 7/2002 | Opara |
| 2004/0022691 A1 | 2/2004 | Allen et al. |
| 2004/0037813 A1* | 2/2004 | Simpson ............ A61F 2/08 424/93.7 |
| 2004/0047837 A1 | 3/2004 | Fong et al. |
| 2005/0026977 A1 | 2/2005 | Jennings |
| 2005/0265977 A1 | 12/2005 | Elliott et al. |
| 2006/0167468 A1 | 7/2006 | Gabbay |
| 2007/0156103 A1 | 7/2007 | Chatlynne et al. |
| 2009/0105811 A1 | 4/2009 | Dinh et al. |
| 2009/0214660 A1 | 8/2009 | Vasconcellos et al. |
| 2010/0311164 A1 | 12/2010 | Robins et al. |
| 2011/0305672 A1 | 12/2011 | Dalton et al. |
| 2012/0214237 A1 | 8/2012 | Robins et al. |
| 2013/0115695 A1 | 5/2013 | Schulz |
| 2013/0122520 A1 | 5/2013 | Kelly et al. |
| 2013/0131828 A1 | 5/2013 | Legeay et al. |
| 2013/0274691 A1 | 10/2013 | De, Jr. et al. |
| 2013/0309708 A1 | 11/2013 | Robins et al. |
| 2013/0316357 A1 | 11/2013 | D'Amour et al. |
| 2014/0099713 A1 | 4/2014 | Robins et al. |
| 2014/0099717 A1 | 4/2014 | Fraker et al. |
| 2014/0134726 A1 | 5/2014 | D'Amour et al. |
| 2014/0134727 A1 | 5/2014 | D'Amour et al. |
| 2014/0147483 A1 | 5/2014 | Hubbell et al. |
| 2014/0154801 A1 | 6/2014 | D'Amour et al. |
| 2014/0154802 A1 | 6/2014 | Robins et al. |
| 2014/0193902 A1 | 7/2014 | D'Amour et al. |
| 2014/0193904 A1 | 7/2014 | D'Amour et al. |
| 2014/0193905 A1 | 7/2014 | Kelly et al. |
| 2015/0017135 A1 | 1/2015 | Agulnick |
| 2015/0132846 A1 | 5/2015 | Schulz |
| 2015/0265657 A1 | 9/2015 | Martinson et al. |
| 2015/0283514 A1 | 10/2015 | Aguilar et al. |
| 2015/0297294 A1 | 10/2015 | So et al. |
| 2015/0298388 A1 | 10/2015 | Wong et al. |
| 2015/0299662 A1 | 10/2015 | Kelly et al. |
| 2015/0374637 A1* | 12/2015 | Wang ............ A61K 9/5073 424/556 |
| 2016/0031054 A1 | 2/2016 | Chang |
| 2016/0036923 A1 | 2/2016 | Phanishayee et al. |
| 2016/0145569 A1 | 5/2016 | Robins et al. |
| 2016/0152950 A1 | 6/2016 | Zhang et al. |
| 2016/0177267 A1 | 6/2016 | Melton et al. |
| 2016/0184569 A1 | 6/2016 | Lathuiliere et al. |
| 2016/0222346 A1 | 8/2016 | Robins et al. |
| 2016/0250262 A1 | 9/2016 | Agulnick et al. |
| 2016/0340645 A1 | 11/2016 | D'Amour et al. |
| 2016/0355787 A1 | 12/2016 | D'Amour et al. |
| 2016/0365556 A1 | 12/2016 | Liu et al. |
| 2016/0369239 A1 | 12/2016 | Agulnick et al. |
| 2016/0374900 A1 | 12/2016 | Green et al. |
| 2017/0022474 A1 | 1/2017 | D'Amour et al. |
| 2017/0029769 A1 | 2/2017 | D'Amour et al. |
| 2017/0029778 A1 | 2/2017 | Peterson et al. |
| 2017/0044498 A1 | 2/2017 | Kelly et al. |
| 2017/0092986 A1 | 3/2017 | Ogawa et al. |
| 2017/0095514 A1 | 4/2017 | Ma et al. |
| 2017/0113028 A1 | 4/2017 | So et al. |
| 2017/0159011 A1 | 6/2017 | D'Amour et al. |
| 2017/0203255 A1 | 7/2017 | Mundrigi et al. |
| 2017/0216365 A1 | 8/2017 | D'Amour et al. |
| 2017/0216489 A1 | 8/2017 | Hubbell et al. |
| 2017/0266372 A1 | 9/2017 | Green et al. |
| 2017/0313979 A1 | 11/2017 | D'Amour et al. |
| 2017/0349884 A1 | 12/2017 | Karp et al. |
| 2017/0354760 A1 | 12/2017 | Martinson et al. |
| 2017/0362572 A1 | 12/2017 | Rieck et al. |
| 2018/0064763 A1 | 3/2018 | Agulnick et al. |

FOREIGN PATENT DOCUMENTS

| | | |
|---|---|---|
| EP | 2650359 A1 | 10/2013 |
| EP | 2730649 A1 | 5/2014 |
| EP | 2056759 B1 | 1/2015 |
| EP | 2954045 A1 | 12/2015 |
| EP | 2722387 A3 | 8/2016 |
| EP | 3131497 A1 | 2/2017 |
| EP | 2420565 B1 | 8/2017 |
| EP | 1994141 B1 | 11/2017 |
| EP | 1786896 B1 | 1/2018 |
| EP | 2356227 B1 | 3/2018 |
| EP | 2964147 B1 | 5/2018 |
| EP | 3220996 A4 | 8/2018 |
| EP | 2674485 B1 | 6/2019 |
| EP | 2650360 B1 | 7/2019 |
| EP | 2341147 B1 | 9/2019 |
| JP | 2004043749 A | 2/2004 |
| WO | WO-9632076 | 10/1996 |
| WO | WO-2006112734 A1 | 10/2006 |
| WO | WO-2008011518 A2 | 1/2008 |
| WO | WO-2008097498 A1 | 8/2008 |
| WO | WO 2008/112190 A1 | 9/2008 |
| WO | WO-2014124172 A1 | 8/2014 |
| WO | WO-2014138671 A2 | 9/2014 |
| WO | WO-2015025686 A1 | 2/2015 |
| WO | WO-2015048184 A1 | 4/2015 |
| WO | WO-2015160348 A1 | 10/2015 |
| WO | WO-2016080943 A1 | 5/2016 |
| WO | WO-2017078177 A1 | 5/2017 |
| WO | WO-2017091943 A1 | 6/2017 |
| WO | WO-2018112026 A1 | 6/2018 |
| WO | WO-2018230588 A1 | 12/2018 |
| WO | WO-2018232180 A1 | 12/2018 |
| WO | WO-2019068059 | 4/2019 |
| WO | WO-2019099725 | 5/2019 |
| WO | WO-2019169351 | 9/2019 |

OTHER PUBLICATIONS

Amilan Nylon Resin, retreived from the internet Jun. 29, 2020: https://www.toray.jp/plastics/en/amilan/technical/tec_003.html#:~:text=Water%20absorption%20rate,Therefore%20nylon%20is%20water%2Dabsorbent.&text=Assuming%20ordinary%20atmospheric%20conditions%20(23,and%201.5%25%20for%20nylon%20610. (Year: 2020).*

Balguid et al., Tissue Engineering: Part A, vol. 15, No. 2, 2009, pp. 437-444 (Year: 2009).*

Kang et al., Journal of Polymer Science: Part A: Polymer Chemistry, vol. 45, pp. 4276-4283 (2007) (Year: 2007).*

Kumagai-Braesch et al., Cell Transplantation, vol. 22, pp. 1137-1146, 2013 (Year: 2013).*

Geller et al., Annals of the New York Academy of Sciences, pp. 438-451, 2006 (Year: 2006).*

Teotia et al., Materials Science and Engineering C, vol. 77 (2017), pp. 857-866 (Year: 2017).*

Trott et al. "Long-Term Culture of Self-renewing Pancreatic Progenitors Derived from Human Pluripotent Stem Cells," Stem Cell Reports, Jun. 6, 2017 (Jun. 6, 2017), vol. 8, No. 6, pp. 1675-1688. entire document.

Chang, et al. Nanoporous Immunoprotective Device for Stem Cell Derived # Cell Replacement Therapy. ACS Nano, Just Accepted Manuscript • DOI: 10.1021/acsnano.7b01239 • Publication Date (Web): Aug. 1, 2017. Downloaded from http://pubs.acs.org on Aug. 2, 2017.

Choukroun, et al., Platelet-rich fibrin (PRF): a second-generation platelet concentrate. Part IV: clinical effects on tissue healing. Oral Surg Oral Med Oral Pathol Oral Radiol Endod. Mar. 2006;101(3):e56-60.

Do, et al., Insulin secretion from beta cells within intact islets: Location matters, Clinical and Experimental Pharmacology & Physiology, Mar. 27, 2015, vol. 42, No. 4, pp. 406-414.

Final Office Action dated Jun. 11, 2019 for U.S. Appl. No. 14/850,755.

Gotoh et al., Gamma-Irradiation as a Tool to Reduce Immunogenicity of Islet Allo-and-Xeonograpfs, Horm Metab Res Suppl., Jan. 1, 1990, vol. 25, pp. 89-96.

(56) References Cited

OTHER PUBLICATIONS

Hao, et al., In Vivo Structure Activity Relationship Study of Dorsomorphin Analogs Identifies Selective VEGF and BMP Inhibitors, ACS Chem Biol., Feb. 19, 2010, vol. 5, No. 2, pp. 245-253.
Hess et al., Bone Marrow-Derived Stem Cells Initiate Pancreatic Regeneration, Nature Biotechnology, Jun. 22, 2003, vol. 21, Issue 7, pp. 763-770.
International Search Report and Written Opinion dated Apr. 29, 2019 for PCT/US18/061364.
International Search Report and Written Opinion dated Jul. 17, 2019 for PCT/US2019/21904.
International Search Report and Written Opinion dated May 8, 2019 for PCT/US2019/020430.
Kalaoglu-Altan, et al., Reactive and 'clickable' electrospun polymeric nanofibers, Polymer Chemistry, 6.18 (2015): 3372-81.
Kishan, et al., In situ crosslinking of electrospun gelatin for improved fiber morphology retention and tunable degradation, Journal of Materials Chemistry B 3, (2015),7930-38.
Kuroyanagi, et al., Establishment of banking system for allogeneic cultured dermal substitute. Artif Organs. Jan. 2004;28(1):13-21.
Lee et al., Differentiation into Endoderm Lineage: Pancreatic differentiation from Embryonic Stem Cells, International Journal of Stem Cells, Apr. 4, 2011, vol. 4, No. 1, pp. 35-42.
Lee, et al., Rapid Formation of Acrylated Microstructures by Microwave-Induced Thermal Crosslinkinga, Macromol Rapid Commun, Jun. 22, 2009, 30(16):1382-86.
Lee, et al., The effects of varying poly(ethylene glycol) hydrogel crosslinking density and the crosslinking mechanism on protein accumulation in three-dimensional hydrogels, Biomaterialia, 2014, 8 pages.
Liang, et al., Functional electrospun nanofibrous scaffolds for biomedical applications, Advanced drug delivery reviews 59.14 (2007): 1392-1412.
Lima et al., Generation of Functional Beta-Like Cells from Human Exocrine Pancreas, PLoS One, May 31, 2016, vol. 11, No. 5, pp. 1-19.
Lin, et al., In situ UV-crosslinking gelatin electrospun fibers for tissue engineering applications, Biofabrication, 5.3 (2013): 035008.
Mehta, et al., Platelet rich concentrate: basic science and current clinical applications. J Orthop Trauma. Jul. 2008;22(6):432-8. doi: 10.1097/BOT.0b013e31817e793f.
Neely et al., DMH1, a Highly Selective Small Molecule BGMP Inhibitor Promotes Neurogenesis of hiPSCs: Comparison of PAX6 and SOX1 Expression During Neural Induction, ACS Chem Neurosci, Mar. 5, 2012, vol. 3, No. 6, pp. 482-491.
Non-Final Office Action dated Apr. 5, 2019 for U.S. Appl. No. 14/563,802.
Pan, et al., Preparation of polyacrylonitrile and polyethyleneglycol blend fibers through electrospinning, Rapid Communications, Jan.-Feb. 2012, 6(1-2):230-34.
PCT/US2018/037637 International Search Report and Written Opinion dated Sep. 21, 2018.
Rezaee, et al., Crosslinked Electrospun Poly (Vinyl Alcohol) Nanofibers Coated by Antibacterial Copper Nanoparticles, Iranian Journal of Chemical Engineering (Summer 2014), 11(3):45-58.
Sarier, et al., Production of PEG grafted PAN copolymers and Their Electrospun Nanowebs as Novel Thermal Energy Storage Materials, 31 Pages.
Skrzypek, K., et al., Pancreatic islet microencapsulation using microwell porous membranes, Scientific Reports, vol. 7, No. 1, Aug. 23, 2017, Abstract; pp. 2-3, 7-10.
Stefani, et al., Development of an in-process UV-crosslinked, electrospun PCL/aPLA-co-TMC composite polymer for tubular tissue engineering applications, Acta biomaterialia, 36 (2016): 231-240.
Vondran, et al., Crosslinked, electrospun chitosan-poly (ethylene oxide) nanofiber mats, Journal of Applied Polymer Science, pp. 968-975. Published online Apr. 11, 2008 in Wiley InterScience (www.interscience.wiley.com).
Wong, et al., Analysis of PAN and PEGDA Coated Membranes for Filtering Water with Reduced Fouling and Increased Heavy Metal Adsorption, Jan. 2012, 1(3):44-50.
Xu, et al., Fabrication of cross-linked polyethyleneimine microfibers by reactive electrospinning with in situ photo-cross-linking by UV radiation, Biomacromolecules 11.9 (2010): 2283-89.
Yun, et al., Fabrication and characterization of electrospun biocompatible PU/PEGMA hybrid nanofibers by in-situ UV photopolymerization, Jul. 2012, 55(7):1189-93.
Zhang, et al., The Microstructure Characterization and the Mechanical Properties of Electrospun Polyacrylonitrile-Based Nanofibers, Nanofibers—Production, Properties and Functional Applications, 178-196.
Zhou, et al., UV-initiated crosslinking of electrospun poly (ethylene oxide) nanofibers with pentaerythritol triacrylate: Effect of irradiation time and incorporated cellulose nanocrystals, Carbohydrate polymers, 87 (2012), pp. 1779-1786.
International Search Report and Written Opinion dated Jan. 24, 2019 for PCT/US18/53665.
[No Author Listed], ASTM D882-02, Standard Test Method for Tensile Properties of Thin Plastic Sheeting. ASTM International. 2002. 10 pages. https://doi.org/10.1520/D0882-02.
[No Author Listed], ASTM D882-18, Standard Test Method for Tensile Properties of Thin Plastic Sheeting. ASTM International. 2018. 12 pages. https://doi.org/10.1520/D0882-18.
[No Author Listed], Semisolid Drug Products—Performance Tests. General Information. Semisolid Drug Products. The United States Pharmacopeial Convention. Aug. 1, 2014:1273-84.
Erdodi et al., A novel macroencapsulating immunoisolatory device: the preparation and properties of nanomat-reinforced amphiphilic co-networks deposited on perforated metal scaffold. Biomed Microdevices. Feb. 2009;11(1):297-312. doi: 10.1007/s10544-008-9236-x.
Risbud et al., Suitability of cellulose molecular dialysis membrane for bioartificial pancreas: in vitro biocompatibility studies. J Biomed Mater Res. Mar. 5, 2001;54(3):436-44. doi: 10.1002/1097-4636(Mar. 5, 2001)54:3<436::aid-jbm180>3.0.co;2-8.
Thanos et al., Considerations for Successful Encapsulated β-Cell Therapy. In: Cell Therapy, Molecular and Translational Medicine. 2017. Emerich et al., Eds. Chapter 2:19-52.

* cited by examiner

Base Electrospun Membrane

Crosslinked Electrospun Membrane

C=C transitions to C-C

DEVICES AND METHODS FOR DELIVERING THERAPEUTICS

CROSS-REFERENCE

This application is a continuation of PCT/US2018/037637, filed Jun. 14, 2018, which claims the benefit of U.S. Provisional Application No. 62/519,702, filed Jun. 14, 2017, which are hereby incorporated herein by reference in their entirety.

BACKGROUND

Diabetes is a chronic disease, which impacts a patient's quality of life. Therapeutic devices to support automated delivery of insulin can be bulky and cumbersome for a patient to use. Implantable devices may provide advantages as they can be discreet and easy to manage. Implantable devices may benefit from exhibiting long term structural integrity and may benefit from allowing passage of therapeutics without allowing infiltration of host proteins. The present invention provides devices and methods of administering the same devices, which allow for high flux of low molecular weight therapeutic moieties while restricting passage of larger proteins or cells.

SUMMARY

Disclosed here are devices, methods, and compositions for delivering a therapeutic (e.g., a cell or a therapeutic agent).

In one aspect, disclosed is a device comprising a membrane and a population of non-native pancreatic β cells, wherein said non-native pancreatic β cells exhibit an in vitro glucose-stimulated insulin secretion (GSIS) response to a glucose challenge, wherein said membrane comprises a $$\frac{D_{first}}{D_{second}}$$

ratio equal to or greater than about 2, wherein $D_{first}$ is a first diffusion coefficient for a first molecule comprising a first molecular weight and $D_{second}$ is a second diffusion coefficient for a second molecule comprising a second molecular weight, and wherein a ratio of said second molecular weight to said first molecular weight is equal to or greater than about 10.

In some cases, said non-native pancreatic β cells are encapsulated within said device. In some cases, said non-native pancreatic β cells do not express somatostatin, glucagon, or both. In some cases, said device is configured to produce and release insulin when implanted into a subject. In some cases, said non-native pancreatic β cells are encapsulated within said device from a range of about $10^4$ to about $10^6$ cells per μL of volume. In some cases, said membrane is configured to block passage of said non-native pancreatic β cells.

In another aspect, disclosed is a device comprising a membrane and a population of cells, wherein at least one cell of said population of cells produces a first molecule comprising a first molecular weight and at least one cell of said population of cells produces a second molecule comprising a second molecular weight, wherein said device, when implanted into a subject, is configured to release said first molecule at a first flux rate and said second molecule at a second flux rate, wherein said first flux rate is different from said second flux rate, and wherein a ratio of said first molecular weight to said second molecular weight is from about 1.0 to about 5.0.

In some cases, said first molecule or said second molecule comprises a therapeutic agent. In some cases, said first molecule is insulin. In some cases, said second molecule is glucagon. In some cases, said ratio of said first molecular weight to said second molecular weight is about 1.6. In some cases, said second molecule is somatostatin. In some cases, said ratio of said first molecular weight to said second molecular weight is about 3.5. In some cases, said therapeutic agent is a hormone or an enzyme. In some cases, said therapeutic agent is a hormone. In some cases, said therapeutic agent is an amino acid derived hormone, an eicosanoid, a peptide hormone, or a steroid. In some cases, said therapeutic agent is selected from the group consisting of glucagon, growth hormone, insulin, pancreatic polypeptide, parathyroid hormone, somatostatin, and glucocorticoid. In some cases, said therapeutic agent is an enzyme. In some cases, said therapeutic agent is a protease, lipase, amylase, phospholipase A2, lysophospholipase, or cholesterol esterase. In some cases, said therapeutic agent is selected from the group consisting of angiotensinogen, trypsinogen, chymotrypsinogen, pepsinogen, fibrinogen, procaspase, pacifastin, proelastase, prolipase, and procarboxypolypeptidase. In some cases, said cells comprise hormone or enzyme secreting cells. In some cases, said cells comprise non-native cells. In some cases, said cells comprise stem cell-derived islet cells. In some cases, said cells comprise non-native pancreatic β cells. In some cases, said cells exhibit an in vitro glucose-stimulated insulin secretion (GSIS) response to a glucose challenge. In some cases, said cells are encapsulated within said device. In some cases, said cells do not express somatostatin, glucagon, or both. In some cases, said device is configured to produce and release insulin when implanted into said subject. In some cases, said cells are encapsulated within said device from a range of about $10^4$ to about $10^6$ cells per μL of volume. In some cases, said membrane is configured to block passage of said cells.

In another aspect, disclosed is a device comprising a membrane and a therapeutic agent, wherein said therapeutic agent is encapsulated within said device, wherein said membrane comprises a $$\frac{D_{first}}{D_{second}}$$

ratio equal to or greater man about 2, wherein $D_{first}$ is a first diffusion coefficient for a first molecule comprising a first molecular weight and $D_{second}$ is a second diffusion coefficient for a second molecule comprising a second molecular weight, and wherein a ratio of said second molecular weight to said first molecular weight is equal to or greater than about 10.

In some cases, said therapeutic agent is a prodrug. In some cases, said therapeutic agent is less than 10 kDa. In some cases, said therapeutic agent is a small molecule. In some cases, said therapeutic agent is a biologic. In some cases, said biologic is a peptide or a protein. In some cases, said therapeutic agent is a hormone or an enzyme. In some cases, said therapeutic agent is a hormone. In some cases, said therapeutic agent is an amino acid derived hormone, an eicosanoid, a peptide hormone, or a steroid. In some cases, said therapeutic agent is selected from the group consisting of glucagon, growth hormone, insulin, pancreatic polypeptide, parathyroid hormone, somatostatin, and glucocorticoid. In some cases, said therapeutic agent is an enzyme. In some cases, said therapeutic agent is a protease, lipase, amylase, phospholipase A2, lysophospholipase, or cholesterol esterase. In some cases, said therapeutic agent is selected from the group consisting of angiotensinogen, trypsinogen, chymotrypsinogen, pepsinogen, fibrinogen, procaspase, pacifastin, proelastase, prolipase, and procarboxypolypeptidase. In some cases, said therapeutic agent is present at a range of from about 0.01 mg therapeutic agent/mg polymer to about 0.5 mg therapeutic agent/mg polymer. In some cases, said therapeutic agent is configured to be released from said membrane for at least 3 days. In some cases, said therapeutic agent is hydrophobic. In some cases, said therapeutic agent is hydrophilic. In some cases, said therapeutic agent is in a form of a micronized particulate.

In another aspect, disclosed is a device comprising a membrane, wherein said membrane comprises a polymer configured to allow encapsulation of a population of cells or a therapeutic agent to said membrane, wherein said membrane comprises at least one of the following: a) an average fiber diameter equal to or less than about 1000 nm; b) an average pore size equal to or less than about 5 μm; and c) an average thickness equal to or less than about 500 μm; and wherein said membrane comprises a $$\frac{D_{first}}{D_{second}}$$

ratio equal to or greater than about 2, wherein $D_{first}$ is a first diffusion coefficient for a first molecule comprising a first molecular weight and $D_{second}$ is a second diffusion coefficient for a second molecule comprising a second molecular weight, and wherein a ratio of said second molecular weight to said first molecular weight is equal to or greater than about 10.

In some cases, said polymer is configured to allow encapsulation of said population of cells. In some cases, said cells comprise hormone or enzyme secreting cells. In some cases, said cells secret a therapeutic agent. In some cases, said therapeutic agent is a hormone. In some cases, said therapeutic agent is an amino acid derived hormone, an eicosanoid, a peptide hormone, or a steroid. In some cases, said therapeutic agent is selected from the group consisting of glucagon, growth hormone, insulin, pancreatic polypeptide, parathyroid hormone, somatostatin, and glucocorticoid. In some cases, said therapeutic agent is an enzyme. In some cases, said therapeutic agent is a protease, lipase, amylase, phospholipase A2, lysophospholipase, or cholesterol esterase. In some cases, said therapeutic agent is selected from the group consisting of angiotensinogen, trypsinogen, chymotrypsinogen, pepsinogen, fibrinogen, procaspase, pacifastin, proelastase, prolipase, and procarboxypolypeptidase. In some cases, said cells comprise non-native cells. In some cases, said cells comprise stem cell-derived islet cells. In some cases, said cells comprise non-native pancreatic β cells. In some cases, said cells exhibit an in vitro glucose-stimulated insulin secretion (GSIS) response to a glucose challenge. In some cases, said cells are encapsulated within said device. In some cases, said cells do not express somatostatin, glucagon, or both. In some cases, said device is configured to produce and release insulin when implanted into said subject. In some cases, said cells are encapsulated within said device from a range of about $10^4$ to about $10^6$ cells per μL of volume. In some cases, said membrane is configured to block passage of said cells.

In some cases, said polymer is configured to allow encapsulation of said therapeutic agent. In some cases, said therapeutic agent is a prodrug. In some cases, said therapeutic agent is less than 10 kDa. In some cases, said therapeutic agent is a small molecule. In some cases, said therapeutic agent is a biologic. In some cases, said biologic is a peptide or a protein. In some cases, said therapeutic agent is a hormone or an enzyme. In some cases, said therapeutic agent is a hormone. In some cases, said therapeutic agent is an amino acid derived hormone, an eicosanoid, a peptide hormone, or a steroid. In some cases, said therapeutic agent is selected from the group consisting of glucagon, growth hormone, insulin, pancreatic polypeptide, parathyroid hormone, somatostatin, and glucocorticoid. In some cases, said therapeutic agent is an enzyme. In some cases, said therapeutic agent is a protease, lipase, amylase, phospholipase A2, lysophospholipase, or cholesterol esterase. In some cases, said therapeutic agent is selected from the group consisting of angiotensinogen, trypsinogen, chymotrypsinogen, pepsinogen, fibrinogen, procaspase, pacifastin, proelastase, prolipase, and procarboxypolypeptidase. In some cases, said therapeutic agent is present at a range of from about 0.01 mg therapeutic agent/mg polymer to about 0.5 mg therapeutic agent/mg polymer. In some cases, said therapeutic agent is configured to be released from said membrane for at least 3 days. In some cases, said therapeutic agent is hydrophobic. In some cases, said therapeutic agent is hydrophilic. In some cases, said therapeutic agent is in a form of a micronized particulate.

In some cases, said membrane comprises an average fiber diameter equal to or less than about 1000 nm. In some cases, said average fiber diameter is equal to or less than about 800 nm. In some cases, said average fiber diameter is equal to or less than about 500 nm. In some cases, said membrane comprises an average pore size equal to or less than about 5 μm. In some cases, said average pore size is equal to or less than about 2 μm. In some cases, said average pore size is equal to or less than about 1 μm. In some cases, said membrane comprises an average thickness equal to or less than about 800 μm. In some cases, said average thickness is equal to or less than about 500 μm. In some cases, said average thickness is equal to or less than about 200 μm. In some cases, said first molecular weight is less than about 10 kDa and said second molecular weight is greater than about 100 kDa. In some cases, said first molecular weight is about 4 kDa and said second molecular weight is about 150 kDa. In some cases, said first molecule is a 4 kDa FITC-dextran molecule and said second molecule is a 500 kDa FITC-dextran molecule. In some cases, said membrane is an electrospun polymer membrane. In some cases, said membrane further comprises a base polymer. In some cases, said base polymer comprises PAN, PET, PLG, PHEMA, PCL, or PLLA. In some cases, said base polymer is PAN. In some cases, said membrane further comprises a functional polymer. In some cases, said functional polymer comprises PEG, PEGMA, PEGDA, or TEGDA. In some cases, said functional polymer is PEGMA. In some cases, said functional polymer is TEGDA. In some cases, said functional polymer comprises a reactive functional group. In some cases, said reactive functional group is a carboxylate group, a hydroxyl group, an amide group, an azide group, or a maleimide group. In some cases, said functional polymer comprises a molecular weight within a range of about 400 to 4000 Da. In some cases, said functional polymer comprises a molecular weight of about 480 Da. In some cases, said functional polymer comprises a molecular weight within a range of about 1500 to 2500 Da. In some cases, said functional polymer comprises a molecular weight of about 2000 Da. In some cases, said ratio is equal to or greater than about 3. In some cases, said ratio is equal to or greater than about 5. In some cases, said ratio is equal to or greater than about 10. In some cases, said membrane comprises a tensile strength equal to or more than about 1 MPa. In some cases, said membrane comprises a Young's Modulus equal to or more than about 5 MPa. In some cases, said membrane is hydrophilic. In some cases, said membrane is hydrophobic.

In another aspect, disclosed is a method of treating a condition comprising: placing any device disclosed herein in a subject in need thereof. In some cases, said device is configured to remain in said subject for a period of more than six months. In some cases, said condition is a chronic disease. In some cases, said chronic disease is diabetes. In some cases, said condition is a tissue wound. In some cases, said condition is hypoparathyroidism. In some cases, said method further comprises monitoring an insulin level of said subject over said period of more than six months.

In another aspect, disclosed is a method of making a device for delivering a population of cells or a therapeutic agent to a subject in need thereof, comprising: dissolving a polymer in a solvent to provide a polymer solution; forming a membrane comprising fibers using said polymer solution; and assembling said membrane into said device, wherein said device is any device disclosed herein.

In some cases, said method further comprises crosslinking said membrane. In some cases, crosslinking said membrane comprises exposing said membrane to ultraviolet (UV) light in presence of a photoinitiator. In some cases, said photoinitiator comprises acetophenone, anisoin, anthraquinone, benzyl, benzoin, benzene tricarbonylchromium, benzoin ethyl ether, benzoin isobutyl ether, benzoin methyl ether, benzophenone, 3,3',4,4'-benzophenonetetracarboxylic dianhydride, 4-benzoylbiphenyl, 2-benzyl-2-(dimethylamino)-4'-morpholinobutyrophenone, 4,4'-bis(diethylamino) benzophenone, camphorquinone, 2-chlorothioxanthen-9-one, (cumene)cyclopentadienyliron(II) hexafluorophosphate, dibenzosuberenone, 2,2-diethoxyacetophenone, 4,4'-dihydroxybenzophenone, 2,2-dimethoxy-2-phenylacetophenone, 4-(dimethylamino)benzophenone, 4,4'-dimethylbenzil, 2,5-dimethylbenzonphenone, 3,4-dimethylbenzophenone, diphenyl(2,4,6-trimethylbenzoyl)phosphine oxide, 4'-ethoxyacetophenone, 2-ethylanthraquinone, ferrocene, 3-hydroxyacetophenone, 4-hydroxyacetophenone, 1-hydroxycyclohexyl phenyl ketone, 2-hydroxy-2-methylpropiophenone, 2-methylbenzophenone, 3-methylbenzophenone, methybenzoylformate, 2-methyl-4'-(methylthio)-2-morpholinoproiophenone,
phenanthrenequinone, 4'-phenoxyacetophenone, thioxanthene-9-one, triarylsulfonium, hexafluoroantimonate salts, triarylsulfonium hexafluorophosphate salts, or any combination thereof. In some cases, crosslinking said membrane comprises exposing said membrane to heat in presence of a heat initiator. In some cases, said heat initiator comprises ammonia persulfate, tert-amyl peroxybenzoate, 4,4-azobis (4-cyanovaleric acid), 1,1'-azobis(cyclohexanecarbonitrile), 2,2'-azobissobutyronitrile, benzoyl peroxide, 2,2-bis(tert-butylperoxy)butane, 1,1-bis(tert-butylperoxy)cyclohexane, 2,5-bis(tert-butylperoxy)-2,5-dimethylhexane, 2,5-bis(tert-butylperoxy)-2,5-dimethyl-3-hexyne, bis(1-(tert-butylperoxyl)-1-methylethyl)benzene, 1,1-bis(tert-butylperoxy)-3,3,5-trimethylcyclohexane, tert-butyl hydroperoxide, tert-butyl peracetate, tert-butyl peroxide, tert-butyl peroxybenzoate, tert-butylperoxy isopropyl carbonate, cumene, hydroperoxide, cyclohexanone peroxide, dicumyl peroxide, lauroyl peroxide, 2,4-pentanedione peroxide, peracetic acid, potassium persulfate, or any combination thereof. In some cases, crosslinking said membrane comprises exposing said membrane to a transition metal. In some cases, said transition metal comprises ions of beryllium, magnesium, calcium, barium, manganese, copper, iron, or any combination thereof. In some cases, crosslinking said membrane further comprises exposing said membrane to a crosslinking agent. In some cases, said crosslinking agent comprises tetra (ethylene glycol) diacrylate, polyethylene glycol diacralte, bis (2-(succinimidyl-oxycarbonyloxyl)ethyl) sulfone, di(n-succinimidyl)glutarate, disuccinimidyl tartrate], 3,3'-dithiobis (sulfosuccinimidyl propionate, p-phenylene diisothiocyanate, sebacic acid bis(N-succinimidyl) ester, suberic acid bis(N-hydroxy succinimide ester), APN-CHO, bromoacetic acid N-hydroxy succinimide ester, CBTF, iodoacetic acid N-hydroxysuccinimide ester, maleimide-PEG-succinimidyl ester, maleimidoacetic acid N-hydroxysuccinimide ester, adipic acid dihydrazide, alkyne-PEG-maleimide, APN-amine, APN-azide, APN-BCN, APN-COCl, biotin-benzyl-tetrazine, biotin-PEG-TPG, 1,11-diazido-3,6,9-trioxaundecane, dibenzocyclooctyne-N-hydroxy succinimidyl ester, dibenzocyclooctyne-maleimide, dibenzocyclooctyne-PEG-maleimide, 4-(maleinimido)phenyl isocyanate purum, 4,4'-methylenebis(phenyl isocyanate), 3-(2-pyridyldithio)propionyl hydrazide, propargyl-N-hydroxylsuccinimidyl ester, PTAD-azide, sulfo-NHS-diazirine) (sulfosuccinimidyl 4,4'-azipentanoate, 4-(N-maleimido)benzophenone, 4-azidopehenacyl bromide, 5-azido-2-nitrobenzoic acid N-hydroxy succinimide ester, succinimidyl-[4-(psoralen-8-yloxy)]butyrate, 4-benzoylbenzoic acid N-succinimidyl ester, 1,4-bis[3-(2-pyridyldithio) propionamido]butane, bis-maleimidoethane, dithio-bis-maleimidoethane, or any combination thereof.

In some cases, said method further comprises adding a drug in to said polymer solution. In some cases, said solvent is a miscible solvent. In some cases, said drug is a hydrophobic drug. In some cases, said drug is a hydrophilic drug. In some cases, said drug is in a form of micronized particulates. In some cases, said method further comprises encapsulating cells within said device. In some cases, said cells are non-native cells. In some cases, said cells are stem cell-derived islet cells. In some cases, said cells exhibit an in vitro glucose-stimulated insulin secretion (GSIS) response to a glucose challenge. In some cases, said method further comprises collecting said fibers in with aid of a rotating drum collector. In some cases, said method further comprises collecting said fibers on a patterned structure. In some cases, said membrane comprises a shape of said patterned structure. In some cases, said solvent comprises DMF, acetone, acetonitrile, aniline, n-butyl acetate, cyclohexanone, chloroform, diacetone alcohol, di(ethylene glycol), dimethyle sulfoxide, dichloromethane, ethanol, ethyl acetate, ethylene dichloride, formic acid, glycerol, methanol, methyl acetate morpholine, 2-nitropropane, 1-pentanol, n-propanol, pyridine, trifloroethanol, tetrahydrofuran, water, or any combination thereof. In some cases, dissolving said polymer in said solvent comprises solving a base polymer and a functional polymer in said solvent. In some cases, said dissolving said base polymer and said functional polymer at a ratio of equal to or less than about 1:1 (w/w) in said solvent. In some cases, said base polymer and said functional polymer at a ratio of equal to or less than about 1:5 (w/w) in said solvent. In some cases, said base polymer and said functional polymer at a ratio of equal to or less than about 1:10 (w/w) in said solvent. In some cases, said base polymer and said functional polymer at a ratio of equal to or less than about 1:20 (w/w) in said solvent. In some cases, said base polymer and said functional polymer are present with said solvent at about a 6% weight to volume percent. In some cases, said membrane does not comprising a coating.

In various aspects, the present disclosure provides a composition for delivering a cell or a therapeutic to a user, the composition comprising a membrane (e.g., electrospun polymer), wherein the membrane comprises: a base polymer; and a functional polymer configured to allow (1) crosslinking of the membrane, and/or (2) conjugation of a therapeutic to the membrane, wherein the membrane comprises a $$\frac{D_{first}}{D_{second}}$$

ratio equal to or greater than about 2, wherein $D_{first}$ is a first diffusion coefficient for moieties comprising a first molecular weight and $D_{second}$ is a second diffusion coefficient for moieties comprising a second molecular weight, and wherein a ratio of the second molecular weight to the first molecular weight is equal to or greater than about 10. In some aspects, the composition further comprises a cell encapsulated within a device comprised of a membrane. In some aspects, the cell is configured to produce insulin. In further aspects, the cell is an engineered stem cell derived beta cell. In still further aspects, the engineered stem cell expresses insulin.

In further aspects, the engineered stem cell is configured to secrete insulin immediately after encapsulation. In some aspects, the cell is encapsulated within the device from a range of about $10^4$ to about $10^6$ cells per μL of volume. In some aspects, the composition further comprises a drug. In some aspects, the drug is a prodrug. In further aspects, the drug is less than 10 kDa. In some aspects, the drug is a small molecule. In other aspects, the drug is a biologic. In further aspects, the biologic is a peptide or a protein.

In some aspects, the drug is present at a range of from about 0.01 mg drug/mg polymer to about 0.5 mg drug/mg polymer. In some aspects, the drug is configured to be released from the membrane for at least 3 days. In some aspects, the drug is a hydrophobic drug. In some aspects, the drug is included in fibers of the membrane (e.g., electrospun polymer membrane). In some aspects, the drug is a hydrophilic drug. In some aspects, the drug is in a form of a micronized particulate. In further aspects, the drug is dispersed within the membrane (e.g., electrospun polymer membrane). In some aspects, the ratio of the second molecular weight to the first molecular weight is equal to or greater than about 20.

In other aspects, the ratio of the second molecular weight to the first molecular weight is equal to or greater than about 30. In some aspects, the first molecular weight is less than about 10 kDa and the second molecular weight is greater than about 100 kDa. In further aspects, the first molecular weight is equal to about 4 kDa and the second molecular weight is equal to about 150 kDa.

In some aspects, the composition further comprises antioxidants, macrophage inhibitors, or anti-inflammatories. In some aspects, the membrane is configured to allow for passage of the cells. In further aspects, the membrane has a pore size equal to or greater than about 5 μm.

In other aspects, the membrane is configured to block passage of cells. In further aspects, the membrane has a pore size equal to or less than about 3 μm. In some aspects, the membrane does not comprise a coating. In some aspects, the base polymer comprises PAN, PET, PLG, PHEMA, PCL, or PLLA. In some aspects, the functional polymer comprises PEG, PEGMA, PEGDA, or TEGDA. In further aspects, the base polymer is PAN. In still further aspects, the functional polymer is PEGMA. In other aspects, the functional polymer is PEGDA. In still other aspects, the functional polymer is TEGDA.

In some aspects, the functional polymer comprises a reactive functional group. In some aspects, the reactive functional group is a carboxylate group, a hydroxyl group, an amide group, an azide group, or a maleimide group. In some aspects, the composition further comprises anti-fibrotic agents, anti-inflammatory agents, pro-vascularizing agents, or hydrophilizing agents. In some aspects, the functional polymer comprises a molecular weight within a range of about 400 to 4000 Da. In further aspects, the functional polymer comprises a molecular weight within a range of about 1500 to 2500 Da.

In some aspects, the functional polymer comprises a molecular weight of about 2000 Da. In some aspects, the functional polymer comprises a molecular weight of about 480 Da. In some aspects, the $D_{first}$ is equal to or more than $10^{-7}$ cm$^2$/sec. In further aspects, the $D_{first}$ corresponds to a diffusion coefficient for insulin, and $D_{second}$ corresponds to a diffusion coefficient for IgG.

In some aspects, the membrane comprises a tensile strength equal to or more than about 1 MPa. In some aspects, the membrane comprises a Young's Modulus equal to or more than about 5 MPa. In some aspects, the membrane comprises fibers.

In further aspects, the fibers comprise diameter within a range of about 180-240 nm. In other aspects, the fibers comprise a diameter within a range of about 520-560 nm. In some aspects, the fibers comprise a diameter equal to or less than about 1000 nm. In some aspects, the membrane comprises a thickness within a range of about 10-150 μm. In further aspects, the membrane comprises a thickness within a range of about 80-120 μm.

In some aspects, the membrane comprises the base polymer and the functional polymer in a ratio of about 1:1. In other aspects, the membrane comprises the base polymer and the functional polymer in a ratio of about 1:5. In still other aspects, the membrane comprises the base polymer and the functional polymer in a ratio of about 1:10. In still other aspects, the membrane comprises the base polymer and the functional polymer in a ratio of about 1:20. In some aspects, the membrane is hydrophilic. In some aspects, the base polymer is configured to provide structural integrity to the membrane. In some aspects, the base polymer is hydrophobic.

In various aspects, the present disclosure provides a method of providing the composition of disclosed herein for a therapy session comprising placing the membrane in a user, wherein the membrane is configured to remain in the user for a period of more than six months. In some aspects, the user has a chronic disease. In further aspects, the chronic disease is diabetes. In some aspects, the method further comprises monitoring an insulin level of the user over the period of more than six months.

In various aspects, the present disclosure provides a method of providing a membrane for delivering cells or therapeutics to a user, the method comprising: dissolving in a solvent, a base polymer and a functional polymer configured to allow (1) crosslinking of the membrane, and/or (2) conjugation of a therapeutic to the membrane to provide a copolymer solution; electrospinning the copolymer solution to generate fibers; collecting the fibers to form the membrane, wherein the membrane comprises a $$\frac{D_{first}}{D_{second}}$$

ratio equal to or greater than about 2, wherein $D_{first}$ is a diffusion coefficient for moieties comprising a first molecular weight and $D_{second}$ is a diffusion coefficient for moieties comprising a second molecular weight, wherein a ratio of the second molecular weight to the first molecular weight is more than about 10.

In some aspects, the method further comprises crosslinking the membrane, wherein the crosslinking step provides the membrane the $$\frac{D_{first}}{D_{second}}$$

ratio equal to or greater than about 2. In some aspects, crosslinking the membrane comprises exposing the membrane to ultraviolet (UV) light in the presence of a photoinitiator. In further aspects, the photoinitiator comprises acetophenone, anisoin, anthraquinone, benzyl, benzoin, benzene tricarbonylchromium, benzoin ethyl ether, benzoin isobutyl ether, benzoin methyl ether, benzophenone, 3,3',4,4'-benzophenonetetracarboxylic dianhydride, 4-benzoylbiphenyl, 2-benzyl-2-(dimethylamino)-4'-morpholinobutyrophenone, 4,4'-bis(diethylamino)benzophenone, camphorquinone, 2-chlorothioxanthen-9-one, (cumene)cyclopentadienyliron (II) hexafluorophosphate, dibenzosuberenone, 2,2-diethoxyacetophenone, 4,4'-dihydroxybenzophenone, 2,2-dimethoxy-2-phenylacetophenone, 4-(dimethylamino) benzophenone, 4,4'-dimethylbenzil, 2,5-dimethylbenzonphenone, 3,4-dimethylbenzophenone, diphenyl(2,4,6-trimethylbenzoyl)phosphine oxide, 4'-ethoxyacetophenone, 2-ethylanthraquinone, ferrocene, 3-hydroxyacetophenone, 4-hydroxyacetophenone, 1-hydroxycyclohexyl phenyl ketone, 2-hydroxy-2-methylpropiophenone, 2-methylbenzophenone, 3-methylbenzophenone, methybenzoylformate, 2-methyl-4'-(methylthio)-2-morpholinoproiophenone, phenanthrenequinone, 4'-phenoxyacetophenone, thioxanthene-9-one, triarylsulfonium, hexafluoroantimonate salts, triarylsulfonium hexafluorophosphate salts, or any combination thereof.

In some aspects, crosslinking the membrane comprises exposing the membrane to ultraviolet (UV) light in the presence of a photoinitiator and a crosslinking agent. In further aspects, the crosslinking agent comprises tetra (ethylene glycol) diacrylate, polyethylene glycol diacralte, bis (2-(succinimidyl-oxycarbonyloxyl)ethyl) sulfone, di(n-succinimidyl)glutarate, disuccinimidyl tartrate], 3,3'-dithiobis (sulfosuccinimidyl propionate, p-phenylene diisothiocyanate, sebacic acid bis(N-succinimidyl) ester, suberic acid bis(N-hydroxy succinimide ester), APN-CHO, bromoacetic acid N-hydroxy succinimide ester, CBTF, iodoacetic acid N-hydroxysuccinimide ester, maleimide-PEG-succinimidyl ester, maleimidoacetic acid N-hydroxysuccinimide ester, adipic acid dihydrazide, alkyne-PEG-maleimide, APN-amine, APN-azide, APN-BCN, APN-COCl, biotin-benzyl-tetrazine, biotin-PEG-TPG, 1,11-diazido-3,6,9-trioxaundecane, dibenzocyclooctyne-N-hydroxy succinimidyl ester, dibenzocyclooctyne-maleimide, dibenzocyclooctyne-PEG-maleimide, 4-(maleinimido)phenyl isocyanate purum, 4,4'-methylenebis(phenyl isocyanate), 3-(2-pyridyldithio)propionyl hydrazide, propargyl-N-hydroxylsuccinimidyl ester, PTAD-azide, sulfo-NHS-diazirine) (sulfosuccinimidyl 4,4'-azipentanoate, 4-(N-maleimido)benzophenone, 4-azidopehenacyl bromide, 5-azido-2-nitriobenzoic acid N-hydroxy succinimide ester, succinimidyl-[4-(psoralen-8-yloxy)]butyrate, 4-benzoylbenzoic acid N-succinimidyl ester, 1,4-bis[3-(2-pyridyldithio) propionamido]butane, bis-maleimidoethane, dithio-bis-maleimidoethane, or any combination thereof.

In some aspects, crosslinking the membrane comprises exposing the membrane to heat in presence of a heat initiator. In further aspects, the heat initiator comprises ammonia persulfate, tert-amyl peroxybenzoate, 4,4-azobis (4-cyanovaleric acid), 1,1'-azobis(cyclohexanecarbonitrile), 2,2'-azobissobutyronitrile, benzoyl peroxide, 2,2-bis(tert-butylperoxy)butane, 1,1-bis(tert-butylperoxy)cyclohexane, 2,5-bis(tert-butylperoxy)-2,5-dimethylhexane, 2,5-bis(tert-butylperoxy)-2,5-dimethyl-3-hexyne, bis(1-(tert-butylperoxyl)-1-methylethyl)benzene, 1,1-bis(tert-butylperoxy)-3,3,5-trimethylcyclohexane, tert-butyl hydroperoxide, tert-butyl peracetate, tert-butyl peroxide, tert-butyl peroxybenzoate, tert-butylperoxy isopropyl carbonate, cumene, hydroperoxide, cyclohexanone peroxide, dicumyl peroxide, lauroyl peroxide, 2,4-pentanedione peroxide, peracetic acid, potassium persulfate, or any combination thereof.

In other aspects, crosslinking the membrane comprises exposing the membrane to heat in presence of a heat initiator and a crosslinking agent. In further aspects, the crosslinking agent comprises tetra (ethylene glycol) diacrylate, polyethylene glycol diacralte, bis(2-(succinimidyl-oxycarbonyloxyl)ethyl) sulfone, di(n-succinimidyl)glutarate, disuccinimidyl tartrate], 3,3'-dithiobis(sulfosuccinimidyl propionate, p-phenylene diisothiocyanate, sebacic acid bis(N-succinimidyl) ester, suberic acid bis(N-hydroxy succinimide ester), APN-CHO, bromoacetic acid N-hydroxy succinimide ester, CBTF, iodoacetic acid N-hydroxysuccinimide ester, maleimide-PEG-succinimidyl ester, maleimidoacetic acid N-hydroxysuccinimide ester, adipic acid dihydrazide, alkyne-PEG-maleimide, APN-amine, APN-azide, APN-BCN, APN-COCl, biotin-benzyl-tetrazine, biotin-PEG-TPG, 1,11-diazido-3,6,9-trioxaundecane, dibenzocyclooctyne-N-hydroxy succinimidyl ester, dibenzocyclooctyne-maleimide, dibenzocyclooctyne-PEG-maleimide, 4-(maleinimido)phenyl isocyanate purum, 4,4'-methylenebis(phenylisocyanate), 3-(2-pyridyldithio)propionylhydrazide, propargyl-N-hydroxylsuccinimidyl ester, PTAD-azide, sulfo-NHS-diazirine) (sulfosuccinimidyl 4,4'-azipentanoate, 4-(N-maleimido)benzophenone, 4-azidopehenacyl bromide, 5-azido-2-nitriobenzoic acid N-hydroxy succinimide ester, succinimidyl-[4-(psoralen-8-yloxy)]butyrate, 4-benzoylbenzoic acid N-succinimidyl ester, 1,4-bis[3-(2-pyridyldithio) propionamido]butane, bis-maleimidoethane, dithio-bis-maleimidoethane, or any combination thereof.

In still other aspects, crosslinking the membrane comprises exposing the membrane to a transition metal. In further aspects, the transition metal comprises ions of beryllium, magnesium, calcium, barium, manganese, copper, iron, or any combination thereof.

In some aspects, the method further comprises incorporating a drug in to the copolymer solution. In some aspects, the solvent is a miscible solvent. In some aspects, the drug is a hydrophilic drug. In further aspects, the drug is in a form of micronized particulates. In some aspects, the method further comprises encapsulating cells within the membrane. In some aspects, the cells are configured to produce insulin.

In some aspects, the method further comprises collecting the fibers in the form of a membrane, which comprises collecting the fibers with aid of a rotating drum collector. In some aspects, the method further comprises collecting the fibers in form of a membrane, which comprises collecting the fibers on a patterned structure. In further aspects, the membrane comprises a shape of the patterned structure.

In some aspects, the solvent comprises DMF, acetone, acetonitrile, aniline, n-butyl acetate, cyclohexanone, chloroform, diacetone alcohol, di(ethylene glycol), dimethyle sulfoxide, dichloromethane, ethanol, ethyl acetate, ethylene dichloride, formic acid, glycerol, methanol, methyl acetate morpholine, 2-nitropropane, 1-pentanol, n-propanol, pyridine, trifloroethanol, tetrahydrofuran, water, or any combination thereof. In some aspects, dissolving the base polymer and the functional polymer in the solvent comprises dissolving the base polymer and the functional polymer at a ratio of about 1:1 in the solvent.

In some aspects, dissolving the base polymer and the functional polymer in the solvent comprises dissolving the base polymer and the functional polymer at a ratio of about 1:5 in the solvent. In other aspects, dissolving the base polymer and the functional polymer in the solvent comprises dissolving the base polymer and the functional polymer at a ratio of about 1:10 in the solvent. In still other aspects, dissolving the base polymer and the functional polymer in the solvent comprises dissolving the base polymer and the functional polymer at a ratio of about 1:20 in the solvent. In some aspects, the base polymer and the functional polymer are present with the solvent at about a 6% weight to volume percent. In some aspects, the method further comprises antioxidants, macrophage inhibitors, or anti-inflammatories.

In some aspects, the membrane is configured to allow passage of the cells. In further aspects, the membrane comprises a pore size equal to or greater than about 5 μm. In some aspects, the membrane is configured to block passage of cells. In further aspects, the membrane comprises a pore size equal to or less than about 3 μm. In some aspects, the membrane does not comprising a coating. In some aspects, the base polymer comprises PAN, PET, PLG, PHEMA, PCL, or PLLA.

In further aspects, the functional polymer comprises PEG, PEGMA, PEGDA, or TEGDA. In some aspects, the base polymer is PAN. In some aspects, the functional polymer is PEGMA. In some aspects, the method further comprises anti-fibrotic agents, anti-inflammatory agents, pro-vascularizing agents, or hydrophilizing agents. In some aspects, the functional polymer comprises a molecular weight within a range of about 500 to 4000 Da. In further aspects, the functional polymer comprises a molecular weight within a range of about 1500 to 2500 Da.

In some aspects, the $D_{first}$ is equal to or more than $10^{-7}$ cm$^2$/sec. In some aspects, the $D_{first}$ corresponds to a diffusion coefficient for insulin, and $D_{second}$ corresponds to a diffusion coefficient for IgG. In some aspects, the membrane comprises a tensile strength equal to or more than about 1 MPa. In further aspects, the membrane comprises a tensile strength from about 1 MPa to about 100 MPa. In some aspects, the membrane comprises a Young's Modulus equal to or more than about 30 MPa. In further aspects, the membrane comprises a Young's Modulus from about 10 MPa to about 100,000 MPa. In some aspects, the fibers comprise diameter within a range of about 180-240 nm.

In other aspects, the fibers comprise a diameter within a range of about 520-560 nm. In some aspects, the fibers comprise a diameter equal to or less than about 1000 nm. In some aspects, the membrane comprises a thickness within a range of about 10-150 um. In further aspects, the membrane comprises a thickness within a range of about 80-120 um. In some aspects, the membrane is hydrophilic. In some aspects, the base polymer is configured to provide structural integrity to the membrane. In some aspects, the base polymer is hydrophobic.

In various aspects the present disclosure provides a membrane for delivering cells or therapeutics to a user, the membrane comprising: a copolymer solution based electrospun fibers, wherein the copolymer solution comprises a base polymer and a functional polymer configured to allow (1) crosslinking of the membrane, and/or (2) conjugation of a therapeutic to the membrane, wherein the membrane comprises a $$\frac{D_{first}}{D_{second}}$$

ratio equal to or greater than about 2, wherein $D_{first}$ is a diffusion coefficient for moieties comprising a first molecular weight less than about 5 kDa and $D_{second}$ is a diffusion coefficient for moieties comprising a second molecular weight greater than about 150 kDa.

In some aspects, the method further comprises crosslinking the membrane, wherein the crosslinking step provides the membrane the $$\frac{D_{first}}{D_{second}}$$

ratio equal to or greater than about 2. In some aspects, crosslinking the membrane comprises exposing the membrane to ultraviolet (UV) light in the presence of a photoinitiator. In further aspects, the photoinitiator comprises acetophenone, anisoin, anthraquinone, benzyl, benzoin, benzene tricarbonylchromium, benzoin ethyl ether, benzoin isobutyl ether, benzoin methyl ether, benzophenone, 3,3',4,4'-benzophenonetetracarboxylic dianhydride, 4-benzoylbiphenyl, 2-benzyl-2-(dimethylamino)-4'-morpholinobutyrophenone, 4,4'-bis(diethylamino)benzophenone, camphorquinone, 2-chlorothioxanthen-9-one, (cumene)cyclopentadienyliron (II) hexafluorophosphate, dibenzosuberenone, 2,2-diethoxyacetophenone, 4,4'-dihydroxybenzophenone, 2,2-dimethoxy-2-phenylacetophenone, 4-(dimethylamino) benzophenone, 4,4'-dimethylbenzil, 2,5-dimethylbenzonphenone, 3,4-dimethylbenzophenone, diphenyl(2,4,6-trimethylbenzoyl)phosphine oxide, 4'-ethoxyacetophenone, 2-ethylanthraquinone, ferrocene, 3-hydroxyacetophenone, 4-hydroxyacetophenone, 1-hydroxycyclohexyl phenyl ketone, 2-hydroxy-2-methylpropiophenone, 2-methylbenzophenone, 3-methylbenzophenone, methybenzoylformate, 2-methyl-4'-(methylthio)-2-morpholinoproiophenone, phenanthrenequinone, 4'-phenoxyacetophenone, thioxanthene-9-one, triarylsulfonium, hexafluoroantimonate salts, triarylsulfonium hexafluorophosphate salts, or any combination thereof.

In some aspects, crosslinking the membrane comprises exposing the membrane to ultraviolet (UV) light in the presence of a photoinitiator and a crosslinking agent. In further aspects, the crosslinking agent comprises tetra (ethylene glycol) diacrylate, polyethylene glycol diacralte, bis (2-(succinimidyl-oxycarbonyloxyl)ethyl) sulfone, di(n-succinimidyl)glutarate, disuccinimidyl tartrate], 3,3'-dithiobis (sulfosuccinimidyl propionate, p-phenylene diisothiocyanate, sebacic acid bis(N-succinimidyl) ester, suberic acid bis(N-hydroxy succinimide ester), APN-CHO, bromoacetic acid N-hydroxy succinimide ester, CBTF, iodoacetic acid N-hydroxysuccinimide ester, maleimide-PEG-succinimidyl ester, maleimidoacetic acid N-hydroxysuccinimide ester, adipic acid dihydrazide, alkyne-PEG-maleimide, APN-amine, APN-azide, APN-BCN, APN-COCl, biotin-benzyl-tetrazine, biotin-PEG-TPG, 1,11-diazido-3,6,9-trioxaundecane, dibenzocyclooctyne-N-hydroxy succinimidyl ester, dibenzocyclooctyne-maleimide, dibenzocyclooctyne-PEG-maleimide, 4-(maleinimido)phenyl isocyanate purum, 4,4'-methylenebis(phenyl isocyanate), 3-(2-pyridyldithio)propionyl hydrazide, propargyl-N-hydroxylsuccinimidyl ester, PTAD-azide, sulfo-NHS-diazirine) (sulfosuccinimidyl 4,4'-azipentanoate, 4-(N-maleimido)benzophenone, 4-azidopehenacyl bromide, 5-azido-2-nitriobenzoic acid N-hydroxy succinimide ester, succinimidyl-[4-(psoralen-8-yloxy)]butyrate, 4-benzoylbenzoic acid N-succinimidyl ester, 1,4-bis[3-(2-pyridyldithio) propionamido]butane, bis-maleimidoethane, dithio-bis-maleimidoethane, or any combination thereof.

In some aspects, crosslinking the membrane comprises exposing the membrane to heat in presence of a heat initiator. In further aspects, the heat initiator comprises ammonia persulfate, tert-amyl peroxybenzoate, 4,4-azobis (4-cyanovaleric acid), 1,1'-azobis(cyclohexanecarbonitrile), 2,2'-azobissobutyronitrile, benzoyl peroxide, 2,2-bis(tert-butylperoxy)butane, 1,1-bis(tert-butylperoxy)cyclohexane, 2,5-bis(tert-butylperoxy)-2,5-dimethylhexane, 2,5-bis(tert-butylperoxy)-2,5-dimethyl-3-hexyne, bis(1-(tert-butylperoxyl)-1-methylethyl)benzene, 1,1-bis(tert-butylperoxy)-3,3, 5-trimethylcyclohexane, tert-butyl hydroperoxide, tert-butyl peracetate, tert-butyl peroxide, tert-butyl peroxybenzoate, tert-butylperoxy isopropyl carbonate, cumene, hydroperoxide, cyclohexanone peroxide, dicumyl peroxide, lauroyl peroxide, 2,4-pentanedione peroxide, peracetic acid, potassium persulfate, or any combination thereof.

In other aspects, crosslinking the membrane comprises exposing the membrane to heat in presence of a heat initiator and a crosslinking agent. In further aspects, the crosslinking agent comprises tetra (ethylene glycol) diacrylate, polyethylene glycol diacralte, bis(-(succinimidyl-oxycarbonyloxyl) ethyl) sulfone, di(n-succinimidyl)glutarate, disuccinimidyl tartrate], 3,3'-dithiobis(sulfosuccinimidyl propionate, p-phenylene diisothiocyanate, sebacic acid bis(N-succinimidyl) ester, suberic acid bis(N-hydroxy succinimide ester), APN-CHO, bromoacetic acid N-hydroxy succinimide ester, CBTF, iodoacetic acid N-hydroxysuccinimide ester, maleimide-PEG-succinimidyl ester, maleimidoacetic acid N-hydroxysuccinimide ester, adipic acid dihydrazide, alkyne-PEG-maleimide, APN-amine, APN-azide, APN-BCN, APN-COCl, biotin-benzyl-tetrazine, biotin-PEG-TPG, 1,11-diazido-3,6,9-trioxaundecane, dibenzocyclooctyne-N-hydroxy succinimidyl ester, dibenzocyclooctyne-maleimide, dibenzocyclooctyne-PEG-maleimide, 4-(maleinimido)phenyl isocyanate purum, 4,4'-methylenebis(phenylisocyanate), 3-(2-pyridyldithio)propionylhydrazide, propargyl-N-hydroxylsuccinimidyl ester, PTAD-azide, sulfo-NHS-diazirine) (sulfosuccinimidyl 4,4'-azipentanoate, 4-(N-maleimido)benzophenone, 4-azidopehenacyl bromide, 5-azido-2-nitriobenzoic acid N-hydroxy succinimide ester, succinimidyl-[4-(psoralen-8-yloxy)]butyrate, 4-benzoylbenzoic acid N-succinimidyl ester, 1,4-bis[3-(2-pyridyldithio) propionamido]butane, bis-maleimidoethane, dithio-bis-maleimidoethane, or any combination thereof.

In still other aspects, crosslinking the membrane comprises exposing the membrane to a transition metal. In further aspects, the transition metal comprises ions of beryllium, magnesium, calcium, barium, manganese, copper, iron, or any combination thereof.

In some aspects, the method further comprises incorporating a drug in to the copolymer solution. In some aspects, the solvent is a miscible solvent. In some aspects, the drug is a hydrophilic drug. In further aspects, the drug is in a form of micronized particulates. In some aspects, the method further comprises encapsulating cells within the membrane. In some aspects, the cells are configured to produce insulin.

In some aspects, the method further comprises collecting the fibers in the form of a membrane, which comprises collecting the fibers with aid of a rotating drum collector. In some aspects, the method further comprises collecting the fibers in form of a membrane, which comprises collecting the fibers on a patterned structure. In further aspects, the membrane comprises a shape of the patterned structure.

In some aspects, the solvent comprises DMF, acetone, acetonitrile, aniline, n-butyl acetate, cyclohexanone, chloroform, diacetone alcohol, di(ethylene glycol), dimethyle sulfoxide, dichloromethane, ethanol, ethyl acetate, ethylene dichloride, formic acid, glycerol, methanol, methyl acetate morpholine, 2-nitropropane, 1-pentanol, n-propanol, pyridine, trifloroethanol, tetrahydrofuran, water, or any combination thereof. In some aspects, dissolving the base polymer and the functional polymer in the solvent comprises dissolving the base polymer and the functional polymer at a ratio of about 1:1 in the solvent.

In some aspects, dissolving the base polymer and the functional polymer in the solvent comprises dissolving the base polymer and the functional polymer at a ratio of about 1:5 in the solvent. In other aspects, dissolving the base polymer and the functional polymer in the solvent comprises dissolving the base polymer and the functional polymer at a ratio of about 1:10 in the solvent. In still other aspects, dissolving the base polymer and the functional polymer in the solvent comprises dissolving the base polymer and the functional polymer at a ratio of about 1:20 in the solvent. In some aspects, the base polymer and the functional polymer are present with the solvent at about a 6% weight to volume percent. In some aspects, the method further comprises antioxidants, macrophage inhibitors, or anti-inflammatories.

In some aspects, the membrane is configured to allow passage of the cells. In further aspects, the membrane comprises a pore size equal to or greater than about 5 μm. In some aspects, the membrane is configured to block passage of cells. In further aspects, the membrane comprises a pore size equal to or less than about 3 μm. In some aspects, the membrane does not comprising a coating. In some aspects, the base polymer comprises PAN, PET, PLG, PHEMA, PCL, or PLLA.

In further aspects, the functional polymer comprises PEG, PEGMA, PEGDA, or TEGDA. In some aspects, the base polymer is PAN. In some aspects, the functional polymer is PEGMA. In some aspects, the method further comprises anti-fibrotic agents, anti-inflammatory agents, pro-vascularizing agents, or hydrophilizing agents. In some aspects, the functional polymer comprises a molecular weight within a range of about 500 to 4000 Da. In further aspects, the functional polymer comprises a molecular weight within a range of about 1500 to 2500 Da.

In some aspects, the $D_{first}$ is equal to or more than $10^{-7}$ cm$^2$/sec. In some aspects, the $D_{first}$ corresponds to a diffusion coefficient for insulin, and $D_{second}$ corresponds to a diffusion coefficient for IgG. In some aspects, the membrane comprises a tensile strength equal to or more than about 1 MPa. In further aspects, the membrane comprises a tensile strength from about 1 MPa to about 100 MPa. In some aspects, the membrane comprises a Young's Modulus equal to or more than about 30 MPa. In further aspects, the membrane comprises a Young's Modulus from about 10 MPa to about 100,000 MPa. In some aspects, the fibers comprise diameter within a range of about 180-240 nm. In other aspects, the fibers comprise a diameter within a range of about 520-560 nm. In some aspects, the fibers comprise a diameter equal to or less than about 1000 nm. In some aspects, the membrane comprises a thickness within a range of about 10-150 um. In further aspects, the membrane comprises a thickness within a range of about 80-120 um. In some aspects, the membrane is hydrophilic. In some aspects, the base polymer is configured to provide structural integrity to the membrane. In some aspects, the base polymer is hydrophobic.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
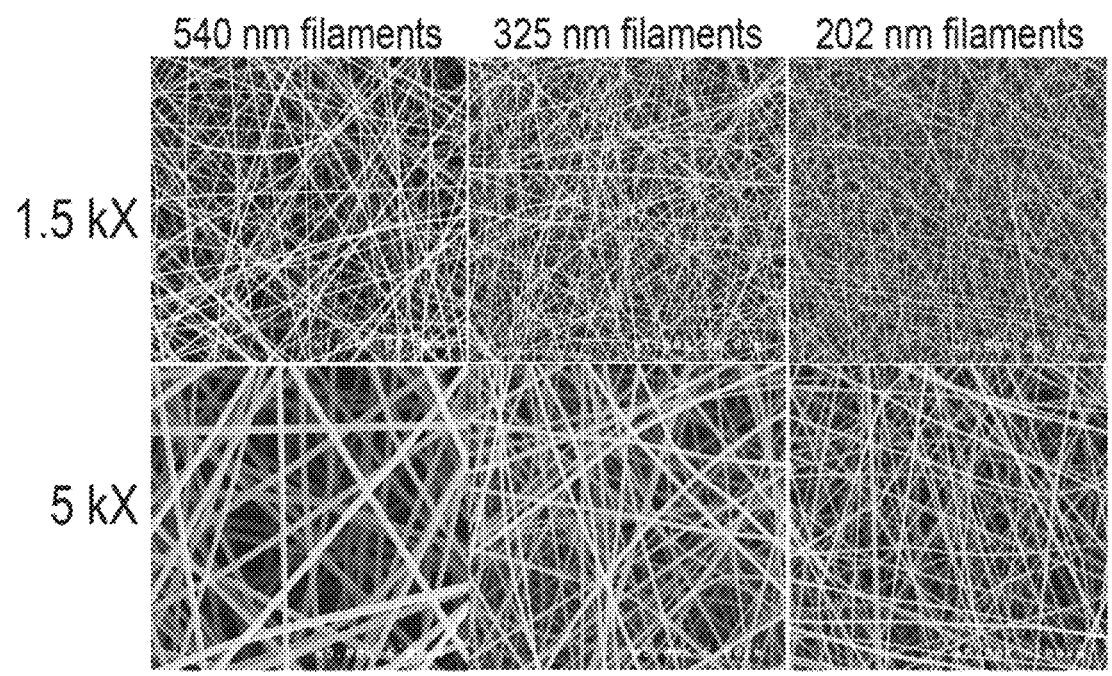
FIG. 1A illustrates scanning electron microscopy (SEM) images of electrospun polymers, in accordance with embodiments.

The present disclosure provides devices, compositions and methods for delivering a therapeutic. For example, various components and characteristics of the devices are disclosed herein, as well as methods of making and using such devices. In some instances, functional electrospun polymers may be crosslinked and/or may be provided in a form of a membrane. While the term membrane is primarily used herein, it is to be understood that a membrane may refer to any shape or form of the functional polymers described herein, and may be utilized for any purpose. For example, the membrane may or may not be thin, may or may not act as a boundary, or lining, or partition, and may or may not allow selective passage of components or different moieties. Optionally, the membrane may be provided as a device, or may be integrated with a device, such as a medical device.

The open terms for example "contain," "containing," "include," "including," and the like mean comprising.

The singular forms "a", "an", and "the" are used herein to include plural references unless the context clearly dictates otherwise.

Unless otherwise indicated, some embodiments herein contemplate numerical ranges. When a numerical range is provided, unless otherwise indicated, the range can include the range endpoints. Unless otherwise indicated, numerical ranges can include all values and subranges therein as if explicitly written out.

The term "about" in relation to a reference numerical value can include a range of values plus or minus 10% from that value. For example, the amount "about 10" includes amounts from 9 to 11, including the reference numbers of 9, 10, and 11. The term "about" in relation to a reference numerical value can also include a range of values plus or minus 10%, 9%, 8%, 7%, 6%, 5%, 4%, 3%, 2%, or 1% from that value.

As used herein, the phrase "membrane" may refer to membranes made by any technique. A subset of "membranes" may include "polymer membranes" in which the membranes are comprised of polymers. A subset of "membranes" may also include "electrospun polymer membranes" described in the present disclosure, in which polymer membranes are made using an electrospinning process disclosed herein. A subset of "electrospun polymer membranes" may include "crosslinked, functional electrospun polymer membranes," in which electrospun polymer membranes are crosslinked via functional polymers. All properties and characteristics described herein, such as diffusion ratios of encapsulated moieties, mechanical properties, and more, can be applicable to membranes, polymer membranes, electrospun polymer membranes, crosslinked, or functional electrospun polymer membranes.

The membranes (e.g., electrospun polymer membranes) described herein may provide advantages for their ease of manufacture and scale up, as well as the ability to modulate various properties of the membrane (e.g., electrospun polymer membrane) based on desired results. For example, the composition and method of making the membranes (e.g., electrospun polymer membranes) can be varied to modulate the diffusion coefficients of encapsulated or infiltrating agents, the mechanical properties (e.g., tensile strength and Young's modulus), and/or the long-term structural integrity. These aspects of the membrane (e.g., electrospun polymer membrane) can be tuned as desired by controlling individual fiber diameter, membrane (e.g., electrospun polymer membrane) thickness, selection of polymer and crosslinker components, amount of polymers (e.g., base polymer and functional polymers), amount of crosslinking polymer or crosslinking agents, method of crosslinking, or any combination thereof.

Functional electrospun polymers of the present disclosure can be used in a number of applications from providing filtration devices, which can be used in research and development, to actual implantable therapeutic products that provide relief for subjects with chronic conditions. As one example, the functional electrospun polymer may be utilized for the purposes of filtration. For example, the membranes (e.g., electrospun polymer membranes) of the present disclosure can be used as a cell filtration device or as a filtration device to exclude high molecular weight moieties (e.g., large proteins). As another example, the functional electrospun polymers may be utilized for the purpose of providing a therapeutic benefit, e.g., with membranes comprising therapeutics or active agents that can release the active agents at a desired rate. In some instances, a polymer based membrane or device may be delivered to a subject in need thereof. For example, the polymer based membrane may be placed adjacent to the subject, or be implanted within the subject. As used herein, a membrane may refer to a collection of the functional polymers.

In some instances, the polymer based membrane may comprise a therapeutic component (also referred to herein as therapeutic moieties). In some instances, the therapeutic component may be configured to be released from the membrane. For example, the membrane may comprise cells (e.g., engineered cells) configured to release a therapeutic moieties and/or drugs which are released from the membrane. The polymer based membrane may comprise characteristics as to allow diffusion or migration of relevant moieties (e.g., therapeutic moieties) into or out of the membrane to provide an effective treatment to a patient or a user. For example, the polymer based membrane may comprise, or be designed with, a diffusion coefficient and/or pore structure that allows relevant therapeutic moieties to diffuse out of the membrane at a desired rate. Alternatively or in addition, the membrane may comprise characteristics as to prevent, limit, or minimize diffusion or migration of relevant moieties (e.g., host proteins, cells, etc) into or out of the membrane. For example, the membrane may comprise, or be designed with a diffusion coefficient and/or pore size that may hinder movement of undesired moieties into the membrane.

In some instances, the polymer based membrane or device may comprise characteristics that meet a balance of providing easy diffusion of relevant moieties (e.g., therapeutic moieties) out of the device and into a subject, while limiting infiltration of undesired moieties (e.g., host proteins such as IgG and BSA). In some instances, polymer based devices encapsulating cells that secrete a therapeutic moiety may be designed or made to allow for release of the therapeutic moiety while preventing cells from migrating in and/or out of the polymer network. Alternatively, or in addition, the polymer based membranes or devices may be designed or made to allow cells from migrating in and/or out of the polymer network.

The membranes described herein may in some instances comprise, and/or be designed to provide a $D_{first}/D_{second}$ ratio, defining the diffusion coefficients of a low molecular weight moiety to a high molecular weight moiety. The low molecular weight moiety may be a therapeutic moiety while the high molecular weight moiety is a host infiltrate or cell. In some instances, cross-linking the membrane described herein may provide desired characteristics for the membrane, such as the $D_{first}/D_{second}$ ratio referred to above. Optionally, the $D_{first}/D_{second}$ ratio may be equal to or greater than 2. Thus, the crosslinked, functional membranes (e.g., electrospun polymer membranes) of the present disclosure may allow for high flux of lower molecular weight therapeutic moieties, while restricting passage of higher molecular weight infiltrates or preventing exit of engineered cells secreting the low molecular weight therapeutic moieties from the device. In some instances, the crosslinked nature of the functional membranes (e.g., electrospun polymer membranes) may additionally bolster the mechanical properties and structural integrity of the membranes disclosed herein.

The membranes (e.g., electrospun polymer membranes) described herein may be engineered to comprise a base polymer and a functional polymer, each of which can be modulated depending on the desired functionality or properties of the resulting membranes. As described above, the membranes may further be crosslinked to modulate the desired functionality or properties of the resulting membrane. Optionally, the membranes may comprise crosslinking agents and crosslinking initiators, as described in further detail below. The compositions and methods described herein enable the development of novel crosslinked, functional membranes (e.g., electrospun polymer membranes) that can be used for various applications, including, but not limited to implantable devices which may be implanted in a subject in need thereof for purposes of treating disease. In one example, the disease may be a chronic disease, such as diabetes. Methods of administration and methods of making crosslinked, functional membranes (e.g., electrospun polymer membranes) are also disclosed herein.

Base Polymers

The membranes described here can comprise a base polymer, or be made of a base polymer. Base polymers can include a number of different categories of polymers including, but not limited to, polyacrylonitriles, polyacrylates, acrylic polymers, methacrylic polymers, polyethers, polyesters, polyurethanes, lactic acid polymers, glycolic acid polymers, cellulose, celluloid, fluoropolymers, nuclear acids, organosilicon polymers, peptides, polyamide, polyacrylamides, polycarbonates, polyaryletherketone, polyolefins, polysaccharides, proteins, tannins, and/or vinyl polymers. Base polymers can be biodegradable or non-biodegradable. Optionally, the base polymers may be biocompatible. The present disclosure provides base polymers, which are biocompatible and suitable for implantation in a subject. In some instances, base polymers can be copolymers, such as poly(lactic-co-glycolic acid) (PLGA), poly(fumaric-co-sebacic anhydride (pFASA), poly(acrylonitrile-co-butadiene), poly(acrylonitrile-co-butyl methacrylate), poly(acrylonitrile-co-vinylidene chloride), or poly(acrylamide) copolymers. In other instances, base polymers can be diblock or triblock polymers. For example, a diblock or triblock polymer could be a fusion of a base polymer and another base polymer. In another example, a diblock or triblock polymer could be a fusion of a base polymer and a functional polymer (e.g., PLGA-PEG).

Controlled degradation can be achieved through incorporating biodegradable polymers (e.g., PLA, PGA, PLGA, PDS, chitosan etc.) into the base polymer solution. Altering the ratio of biodegradable/base polymer, the molecular weight of biodegradable polymer, and/or the electrospinning parameters, can enable control over the degradation kinetics, to achieve specific desirable in a variety of physiological environments (e.g., drug delivery targets, implant sites, pathological conditions). In one exemplary embodiment, a biodegradable polymer (e.g., PLA, PGA, PLGA, PDS, chitosan) is electrospun independently or with a nonbiodegradable polymer (e.g., PAN) in the presence of crosslinker (e.g., TEGDA) to construct biodegradable controlled release of a drug (e.g., CXCL12).

Base polymers can be configured to provide structural integrity to the membranes described herein. In some instances, the base polymer can be hydrophobic. For example, a hydrophobic base polymer could be selected stimulate a stronger foreign body response if desired. Optionally, specific base polymers can be chosen to design a polymer membrane, depending on the desired application. In some cases, to design an implantable membrane, a base polymer that is biocompatible, hydrophobic, and provides appropriate structurally integrity may be selected. In further cases, to design the implantable membrane, a non-biodegradable polymer is selected to provide long term structural integrity in biological conditions. In some instances, a base polymer may be selected according to a desired elasticity, hydrophilicity, reactivity in conjugation chemistry, surface energy, optical properties, swellability, or ability to electrospin at desired filament diameters.

Base polymers of the present disclosure include, but are not limited to, polyacrylonitrile (PAN), polyethylene terephthalate (PET), poly(d,l-lactide-co-glycolide) (PLG), poly (2-hydroxyethyl methacrylate) (PHEMA), polycaprolactone (PCL), poly(acrylonitrile)-poly(vinyl chloride) (PAN-PVC) copolymer, polycarbonate (PC), polydimethylsiloxane (PDMS), polyethylene (PE), polyethylene glycol (PEG, also referred to as poly(ethylene oxide) or PEO), polyethersulfone (PES), poly(glycolic acid) (PGA), Poly(methyl methacrylate) (PMMA), polysulfone (PSf), polystyrene (PSt), polytetrafluoroethylene (PTFE), polyurethane (PU), poly(vinyl acetate) (PVAc), poly(vinyl alcohol) (PVA), polyvinylidene fluoride (PVDF), polylactic acid (PLA) (including Poly(D,L-lactic acid) Poly(L-lactic acid)), cellulose, celluloid, fluoropolymers, nuclear acids, organosilicon polymers, peptides, polyamide, polyacrylamides, polycarbonates, polyaryletherketone, polyolefins, polysaccharides, proteins, tannins, vinyl polymers, or any combination thereof.

In an exemplary embodiment, membranes (e.g., electrospun polymer membranes) comprise a base polymer of PAN. In other embodiments, membranes (e.g., electrospun polymer membranes) can have base polymers of PAN, PCL, EVA, PLLA, pFASA, or any combination thereof. Any combination of the polymers described herein may be used herein to make up the base polymer composition. For example, any one base polymer described above, any two base polymers described above, any three base polymers described above, any four base polymers described above, any five base polymers, or more can be used in combination to make up the base polymer component of the membrane (e.g., electrospun polymer membrane). Excipients that can be included in any membrane (e.g., electrospun polymer membrane) described herein include excipients that can enhance or control tissue integration, including extracellular matrix proteins (laminin, collagen, others), hydrogels (alginate, chitosan, agarose, carboxymethylcellulose), gelatin, poly(dimethylsiloxane, poly(hydroxyethylmethacrylate), poly(ethylene glycol), and microtextured versions thereof.

Base polymers of the present disclosure can have a range of molecular weights including about 10 kDa to about 2,000 kDa. For example, a base polymer of the present disclosure, such as PAN, can have a molecular weight of 150,000 Da.

Functional Polymers

The membranes of the present disclosure may in some instances comprise, or be made of functional polymers. Functional polymers can be amenable to further synthetic manipulation to impart additional properties to the membrane. For example, the functional polymers may be configured to allow crosslinking of the membrane. Alternatively or in addition, the functional polymers may be configured to allow conjugation of a therapeutic to the membrane. Optionally, the functional polymers may impart properties to the membrane such as improved mechanical strength and/or device integrity. Functional polymers described herein can include, but are not limited to, polyethylene glycol (PEG), poly(ethylene glycol) methacylate (PEGMA), poly(ethylene glycol) diacylate (PEGDA), tetraethyleneglycol diacrylate (TEGDA), or any combination thereof.

Functional polymers can also include maleimide-PEG-succinimidyl ester, alkyne-PEG-maleimide, biotin-PEG-TPG, dibenzocyclooctyne-PEG-maleimide, Nonpolymer agents can include bis(2-(succinimidyl-oxycarbonyloxyl) ethyl) sulfone, di(n-succinimidyl)glutarate, disuccinimidyl tartrate], 3,3'-dithiobis(sulfosuccinimidyl propionate, p-phenylene diisothiocyanate, sebacic acid bis(N-succinimidyl) ester, suberic acid bis(N-hydroxy succinimide ester), APN-CHO, bromoacetic acid N-hydroxy succinimide ester, CBTF, iodoacetic acid N-hydroxysuccinimide ester, maleimidoacetic acid N-hydroxysuccinimide ester, adipic acid dihydrazide, APN-amine, APN-azide, APN-BCN, APN-COCl, biotin-benzyl-tetrazine, 1,11-diazido-3,6,9-trioxaundecane, dibenzocyclooctyne-N-hydroxy succinimidyl ester, dibenzocyclooctyne-maleimide, 4-(maleinimido)phenyl isocyanate purum, 4,4'-methylenebis(phenyl isocyanate), 3-(2-pyridyldithio)propionyl hydrazide, propargyl-N-hydroxylsuccinimidyl ester, PTAD-azide, sulfo-NHS-diazirine) (sulfosuccinimidyl 4,4'-azipentanoate, 4-(N-maleimido) benzophenone, 4-azidopehenacyl bromide, 5-azido-2-nitriobenzoic acid N-hydroxy succinimide ester, succinimidyl-[4-(psoralen-8-yloxy)]butyrate, 4-benzoylbenzoic acid N-succinimidyl ester, 1,4-bis[3-(2-pyridyldithio)propionamido]butane, bis-maleimidoethane, dithio-bis-maleimidoethane and more. In an exemplary embodiment, membranes (e.g., electrospun polymer membranes) comprise PEGMA as the functional polymer. Alternatively, PEGMA and TEGDA can be used as the functional polymers in the membranes (e.g., electrospun polymer membranes) of the present disclosure.

Functional polymers may also be referred to herein as "crosslinkers." In some embodiments, the further synthetic manipulation that functional polymers are amenable to include crosslinking. For example, after incorporation in membranes (e.g., electrospun polymer membranes) of the present disclosure, functional polymers can be crosslinked by ultraviolet (UV) light, heat, exposure to transition metals, chemical reaction-based crosslinking, or any combination thereof. For example, exemplary membranes (e.g., electrospun polymer membranes) of the present disclosure can include PAN as a base polymer and PEGMA or PEGMA and TEGDA as functional polymers. These membranes (e.g., electrospun polymer membranes) can be further exposed to UV light in the presence of a photoinitiator to promote crosslinking of the membrane, thus improving mechanical properties and device integrity as well as modulating release of any loaded agents (e.g., cells or drugs).

In some instances, functional polymers may provide the ability to conjugate a therapeutic moiety to the membrane. This can be achieved by the presence of activated sites, which can form chemical bonds or physical interactions with conjugate drugs or therapeutic agents onto the activated site. In some instances, the therapeutic moiety may be included or be a part of fibers of the membrane. For example, the drugs may be dispersed within a polymer solution prior to electrospinning of the polymer membrane as described herein. Alternatively or in addition, drugs may be conjugated to the membrane after the polymer solution has been electrospun to form the membrane. Drugs can also be incorporated into spun fibers or attached post-hoc using coupling chemistry. As used herein, a therapeutic moiety may refer to a drug and the terms may be used interchangeably. However, it is to be understood that the term "drug" is not meant to be limiting and may refer to any therapeutic moiety including, but not limited to prodrugs, small molecules, biologics, peptides, proteins, etc. The drug may be hydrophilic or hydrophobic. In some instances, the drug may be in a form of micronized particulates. In some cases the drugs could include anti-inflammatories such as cilostazol, dexamethasone, and triamcinolone, anti-colony stimulating factors, and other immunomodulatory cytokines and factors.

Functional polymer can also be defined by the presence of a reactive functional group for crosslinking and/or conjugation of a drug. The reactive functional group may include, but are not limited to, a carboxylate group, a hydroxyl group, an amide group, an azide group, a maleimide group, an isocyanate group, a aziridine group, an acrylic alkene group, a triaziridine group, an epoxy group, an activated alkene group, an aldehyde group, a ketone group, an acrylate group, an alcohol group, an acrylamide group, a multicarboxylic acid group, a metal alkoxide group, an acetylene group, an alkene group, a conjugated diene group, an alkyne group, or a cynide group. Specific crosslinking strategies are further described below.

Any mixture of the above described functional polymers can be used herein to make up the functional polymer composition. For example, any functional one polymer described above, any two functional polymers described above, any three functional polymers described above, any four functional polymers described above, or any five functional polymers described above can be used in combination to make up the functional polymer component of the membrane (e.g., electrospun polymer membrane).

Base and Functional Polymers

In some instances, the membranes described herein can comprise both a base polymer and a functional polymer. For example, a base and functional polymers may each be dissolved in a desired solvent as described herein and be mixed together prior to electrospinning. The membrane can comprise, or be made of different mass ratios of the base polymer to the functional polymer. For example, the membrane (e.g., electrospun polymer membrane) can comprise a mass ratio (w/w) equal or greater than about 5000 to 1, 2000 to 1, 1000 to 1, 800 to 1, 600 to 1, 400 to 1, 200 to 1, 100 to 1, 50 to 1, 20 to 1, 10 to 1, 5 to 1, 2 to 1, 1 to 1, 1 to 2, 1 to 5, 1 to 10, 1 to 20, 1 to 50, 1 to 100, 1 to 200, 1 to 400, 1 to 600, 1 to 800, 1 to 1000, 1 to 2000, 1 to 5000, or any value therebetween. In some instances, the membrane (e.g., electrospun polymer membrane) can comprise a mass ratio (w/w) within a range from about 0.001 to 1000, 0.001 to 100, 0.001 to 10, 0.001 to 1, 0.001 to 0.1, 0.001 to 0.01, 0.001 to 0.1, 0.01 to 1000, 0.01 to 100, 0.01 to 10, 0.01 to 1, 0.01 to 0.1, 0.1 to 1000, 0.1 to 100, 0.1 to 10, 0.1 to 1, 1 to 1000, 1 to 100, 1 to 10, 10 to 1000, 10 to 100, or 100 to 1000 of a functional polymer to a base polymer.

Optionally, the base polymer may be PAN and the functional polymer may be PEGMA. The membrane (e.g., electrospun polymer membrane) can comprise the same ratio of functional polymer as compared to base polymer, at least five fold higher base polymer than functional polymer, at least six fold higher base polymer than functional polymer, at least seven fold higher base polymer than functional polymer, at least eight fold higher base polymer than functional polymer, at least nine fold higher base polymer than functional polymer, at least 10 fold higher base polymer than functional polymer, at least 11 fold higher base polymer than functional polymer, at least 12 fold higher base polymer than functional polymer, at least 13 fold higher base polymer than functional polymer, at least 14 fold higher base polymer than functional polymer, at least 15 fold higher base polymer than functional polymer, at least 16 fold higher base polymer than functional polymer, at least 17 fold higher base polymer than functional polymer, at least 18 fold higher base polymer than functional polymer, at least 19 fold higher base polymer than functional polymer, or at least 20 fold higher base polymer than functional polymer. A functional polymer, such as PEGMA, can thus be incorporated into the membrane (e.g., electrospun polymer membrane) from at least 0.5% (w/w) to at least 50% (w/w) of the total polymer composition. In other cases, a functional polymer can also be incorporated at lower percentages, such as at least 2%, at least 3%, at least 4%, at least 5%, at least 6%, or at least 7% of the total polymer composition.

In some cases, incorporation of a higher percentage of crosslinker, or functional polymer, can result in dampening of the release of an encapsulated moiety. For example, a higher percentage of crosslinker may result in more crosslinking, which may result in a porosity (e.g., pore size) of the membrane decreasing, resulting in a dampened released of encapsulated moieties. For example, as shown in FIG. 9C, changing the ratio of PEGMA to PAN in a membrane (e.g., electrospun polymer membrane) from 1:5 PEGMA:PAN to 1:10 PEGMA:PAN resulted in increased burst release of drug. For example, as shown in FIG. 9C, increasing the concentration of PEGMA in the membrane from 1:10 PEGMA:PAN to 1:5 PEGMA PAN may result in a decrease in the flux of drug from membranes. As also shown in FIG. 7C, changing the ratio of PEGMA to PAN from 1:10 to 1:5 resulted in more crosslinking and a dampened release of a drug from membranes (e.g., electrospun polymer membranes).

Figure 6A:
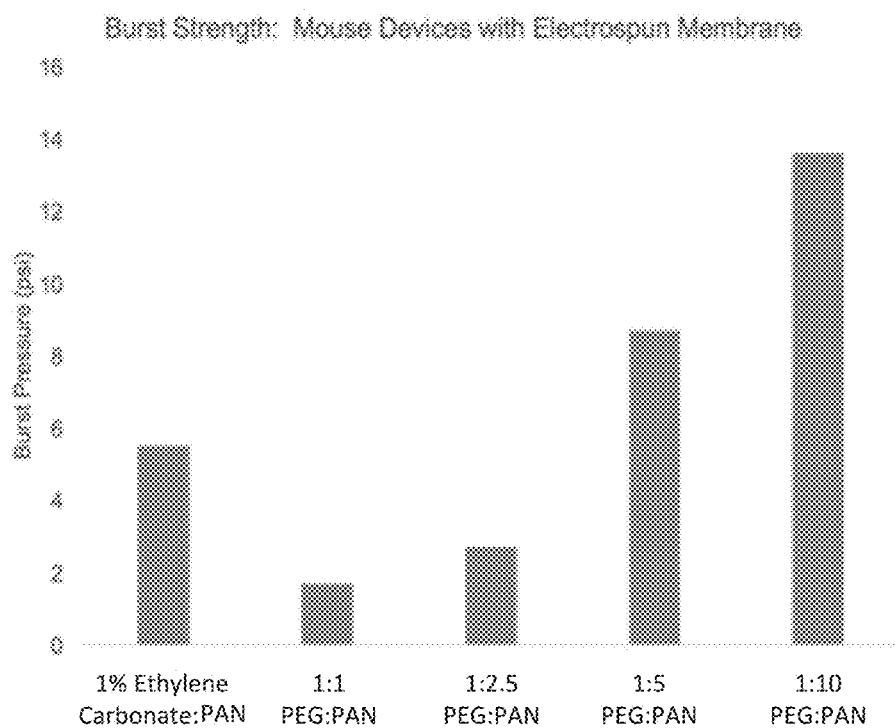
FIG. 6A illustrates the pressure (psi) at which electrospun polymer membranes burst, in accordance with embodiments.
Figure 6B:
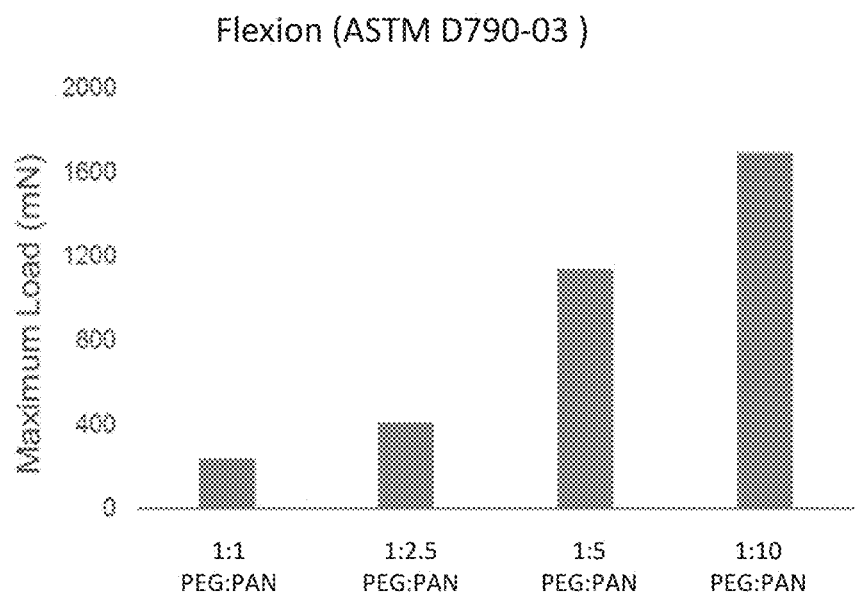
FIG. 6B illustrates the maximum load (mN) withstood by electrospun polymer membranes per ASTM D790-03, in accordance with embodiments.

The ratio of base polymer to a functional polymer may also influence the burst pressure of the membrane (e.g., electrospun polymer membrane). As shown in FIG. 6A, increasing the amount of the base polymer (PAN) in the membrane (e.g., electrospun polymer membrane) can increase the burst pressure. Thus, one strategy to improve the pressure a membrane (e.g., electrospun polymer membrane) of the present disclosure can withstand before rupture, may be to increase the amount of base polymer (e.g., PAN) and/or reduce the amount of functional polymer (e.g., PEG) used in the composition. The ratio of base polymer to a functional polymer can also influence the maximum load of the membrane (e.g., electrospun polymer membrane). As shown in FIG. 6B, increasing the amount of the base polymer (PAN) in the membrane (e.g., electrospun polymer membrane) can increase the maximum load. Thus, one strategy to improve the maximum load that a membrane (e.g., electrospun polymer membrane) of the present disclosure can withstand before failure is to increase the amount of base polymer (e.g., PAN) and/or reduce the amount of functional polymer (e.g., PEG).

Functional polymers compatible with the present disclosure can have molecular weights ranging from 100 Da to 10000 Da. In some instances, a base polymer of the present disclosure can have a molecular weight equal to, or less than 100 Da, 200 Da, 400 Da, 600 Da, 800 Da, 1,000 Da, 1,200 Da, 1,500 Da, 2,000 Da, 2,500 Da, 3,000 Da, 3,500 Da, 4,000 Da, 4,500 Da, 5,000 Da, 6,000 Da, 7,000 Da, 8,000 Da, 9,000 Da, 10,000 Da, 12,000 Da, 14,000 Da, 16,000 Da, 18,000 Da, 20,000 Da, 30,000 Da, 40,000 Da, 50,000 Da, 60,000 Da, 70,000 Da, 80,000 Da, 90,000 Da, 100,000 Da, 150,000 Da, 200,000 Da, 250,000 Da, 300,000 Da, 350,000 Da, 400,000 Da, 450,000 Da, 500,000 Da, 600,000 Da, 700,000 Da, 800,000 Da, 900,000 Da, 1,000,000 Da, 1,100,000 Da, 1,200,000 Da, 1,300,000 Da, 1,400,000 Da, 1,500,000 Da, 1,600,000 Da, 1,700,000 Da, 1,800,000 Da, 1,900,000 Da, or 2,000,000 Da. In some instances, a base polymer of the present disclosure can have a molecular weight equal to, or greater than 100 Da, 200 Da, 400 Da, 600 Da, 800 Da, 1000 Da, 1200 Da, 1500 Da, 2000 Da, 2500 Da, 3000 Da, 3500 Da, 4000 Da, 4500 Da, 5000 Da, 6000 Da, 7000 Da, 8000 Da, 9000 Da, 10000 Da, 12000 Da, 14000 Da, 16000 Da, 18000 Da, 20000 Da, 30,000 Da, 40,000 Da, 50,000 Da, 60,000 Da, 70,000 Da, 80,000 Da, 90,000 Da, 100,000 Da, 150,000 Da, 200,000 Da, 250,000 Da, 300,000 Da, 350,000 Da, 400,000 Da, 450,000 Da, 500,000 Da, 600,000 Da, 700,000 Da, 800,000 Da, 900,000 Da, 1,000,000 Da, 1,100,000 Da, 1,200,000 Da, 1,300,000 Da, 1,400,000 Da, 1,500,000 Da, 1,600,000 Da, 1,700,000 Da, 1,800,000 Da, 1,900,000 Da, or up to 2,000,000 Da. Optionally, the base polymers of the present disclosure can have a molecular weight within a range from about 100 Da to about 200 Da, from about 200 Da to about 400 Da, from about 400 Da to about 600 Da, from about 600 Da to about 800 Da, from about 800 Da to about 1,000 Da, from about 1,000 Da to about 1,200 Da, from about 1,200 Da to about 1,500 Da, from about 1,500 Da to about 2,000 Da, from about 2,000 Da to about 2,500 Da, from about 2,500 Da to about 3,000 Da, from about 3,000 Da to about 3,500 Da, from about 3,500 Da to about 4,000 Da, from about 4,000 Da to about 4,500 Da, from about 4,500 Da to about 5,000 Da, from about 5,000 Da to about 6,000 Da, from about 6,000 Da to about 7,000 Da, from about 7,000 Da to about 8,000 Da, from about 8,000 Da to about 9,000 Da, from about 9,000 Da to about 10,000 Da, from about 10,000 Da to about 12,000 Da, from about 12,000 Da to about 14,000 Da, from about 14,000 Da to about 16,000 Da, from about 16,000 Da to about 18,000 Da, from about 18,000 Da to about 20,000 Da, from about 20,000 Da to about 30,000 Da, from about 30,000 Da to about 40,000 Da, from about 40,000 Da to about 50,000 Da, from about 50,000 Da to about 60,000 Da, from about 60,000 Da to about 70,000 Da, from about 70,000 Da to about 80,000 Da, from about 80,000 Da to about 90,000 Da, from about 90,000 Da to about 100,000 Da, from about 100,000 Da to about 150,000 Da, from about 150,000 Da to about 200,000 Da, from about 200,000 Da to about 250,000 Da, from about 250,000 Da to about 300,000 Da, from about 300,000 Da to about 350,000 Da, from about 350,000 Da to about 400,000 Da, from about 400,000 Da to about 450,000 Da, from about 450,000 Da to about 500,000 Da, from about 500,000 Da to about 600,000 Da, from about 600,000 Da to about 700,000 Da, from about 700,000 Da to about 800,000 Da, from about 800,000 Da to about 900,000 Da, from about 900,000 Da to about 1,000,000 Da, from about 1,000,000 Da to about 1,100,000 Da, from about 1,100,000 Da to about 1,200,000 Da, from about 1,200,000 Da to about 1,300,000 Da, from about 1,300,000 Da to about 1,400,000 Da, from about 1,400,000 Da to about 1,500,000 Da, from about 1,500,000 Da to about 1,600,000 Da, from about 1,600,000 Da to about 1,700,000 Da, from about 1,700,000 Da to about 1,800,000 Da, from about 1,800,000 Da to about 1,900,000 Da, or from about 1,900,000 Da to about 2,000,000 Da. Functional polymers compatible with the present disclosure can have molecular weights from 1500 Da to 2500 Da. In some instances, a functional polymer of the present disclosure can have a molecular weight equal to, or less than 100 Da, 200 Da, 400 Da, 600 Da, 800 Da, 1000 Da, 1200 Da, 1500 Da, 2000 Da, 2500 Da, 3000 Da, 3500 Da, 4000 Da, 4500 Da, 5000 Da, 6000 Da, 7000 Da, 8000 Da, 9000 Da, 10000 Da, 12000 Da, 14000 Da, 16000 Da, 18000 Da, or 20000 Da. In some instances, a functional polymer of the present disclosure can have a molecular weight equal to, or greater than 100 Da, 200 Da, 400 Da, 600 Da, 800 Da, 1000 Da, 1200 Da, 1500 Da, 2000 Da, 2500 Da, 3000 Da, 3500 Da, 4000 Da, 4500 Da, 5000 Da, 6000 Da, 7000 Da, 8000 Da, 9000 Da, 10000 Da, 12000 Da, 14000 Da, 16000 Da, 18000 Da, or 20000 Da. Optionally, the functional polymers of the present disclosure can have a molecular weight within a range between 100 Da, 200 Da, 400 Da, 600 Da, 800 Da, 1000 Da, 1200 Da, 1500 Da, 2000 Da, 2500 Da, 3000 Da, 3500 Da, 4000 Da, 4500 Da, 5000 Da, 6000 Da, 7000 Da, 8000 Da, 9000 Da, 10000 Da, 12000 Da, 14000 Da, 16000 Da, 18000 Da, or 20000 Da. In some cases, a functional polymer (e.g., PEGMA) incorporated into the membrane (e.g., electrospun polymer membrane) can have a molecular weight of 480 Da. In other cases, a functional polymer (e.g., PEGMA) incorporated into the membrane (e.g., electrospun polymer membrane) can have a molecular weight of 2000 Da.

Figure 10:
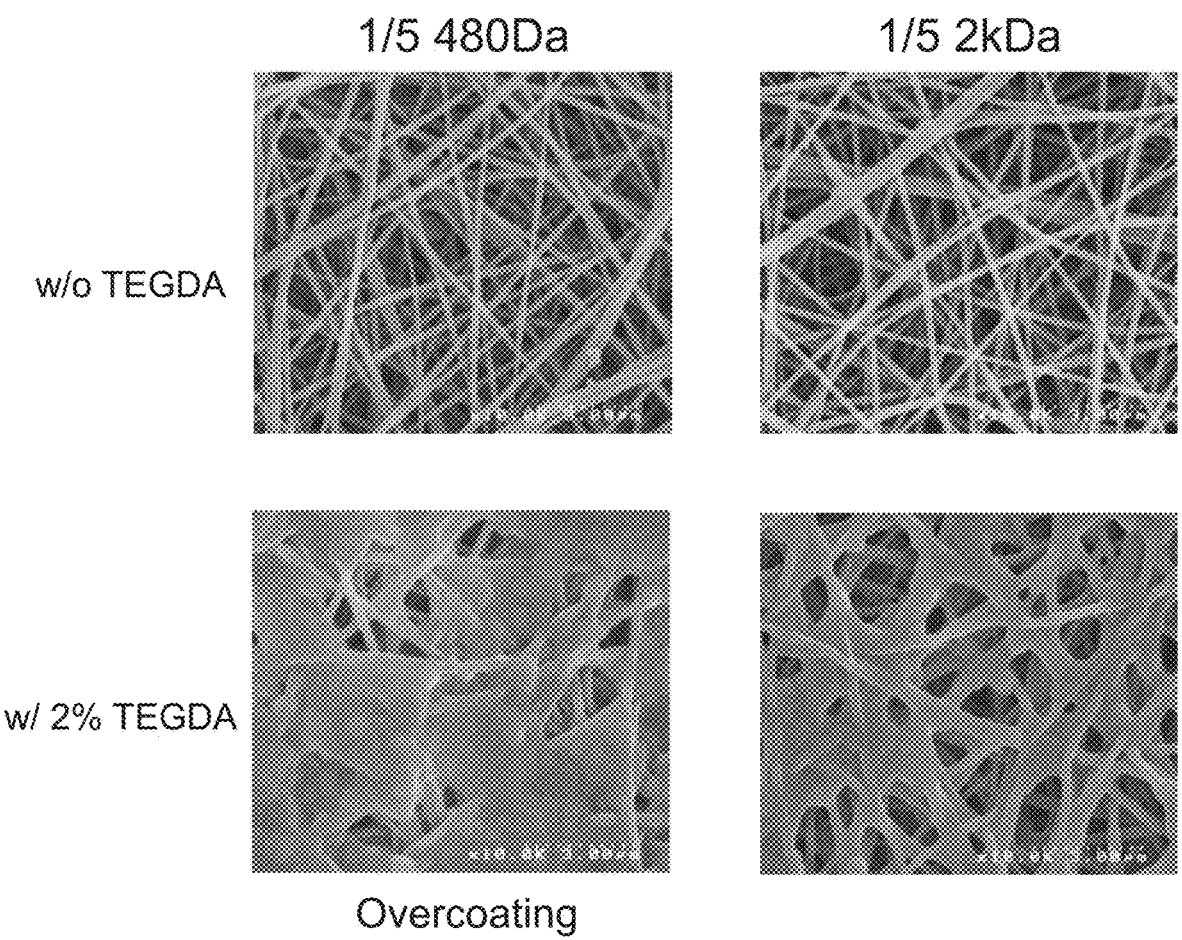
FIG. 10 illustrates SEM images showing the ultrastructure of functional, electrospun polymer membranes after UV-crosslinking, in accordance with embodiments.

The molecular weight of the functional polymer can be an important factor in determining the structure and/or functionality of the polymer membranes of the present disclosure. FIG. 10 demonstrates the change in the coating of crosslinked, functional membranes (e.g., electrospun polymer membranes) made of PAN/PEGMA polymers at a 1/5 ratio and TEGDA with different molecular weights of PEGMA, including 480 Da and 2 kDa. Lower molecular weight functional polymers may have more reactive functional groups that are points of crosslinking at a given chain length. In comparison, high molecular weight functional polymers may have less reactive functional groups that are points of crosslinking in the same given chain length. As a result, upon crosslinking, as shown in FIG. 10, lower molecular weight PEGMA in crosslinked, functional membranes (e.g., electrospun polymer membranes) may result in an overcoating such that porosity is significantly smaller than in high molecular weight PEGMA incorporated in the membranes.

Figure 9A:
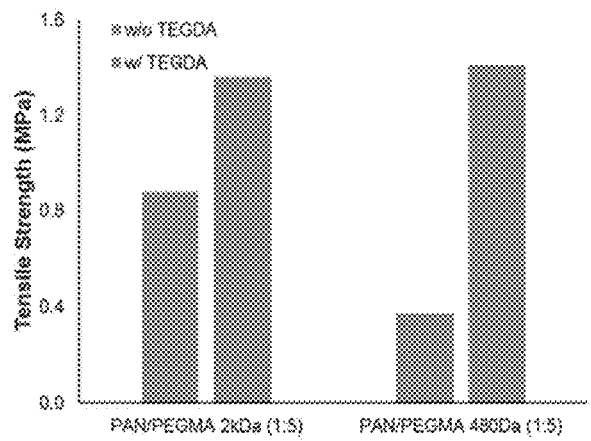
FIG. 9A illustrates the tensile strength (MPa) of crosslinked, functional electrospun polymer membranes, in accordance with embodiments.
Figure 9B:
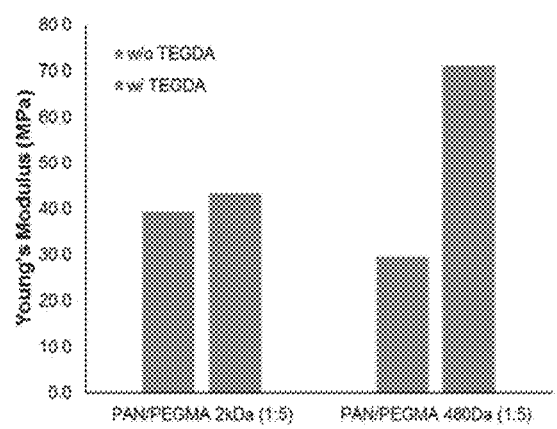
FIG. 9B illustrates the Young's modulus (MPa) of crosslinked, functional electrospun polymer membranes, in accordance with embodiments.
Figure 9C:
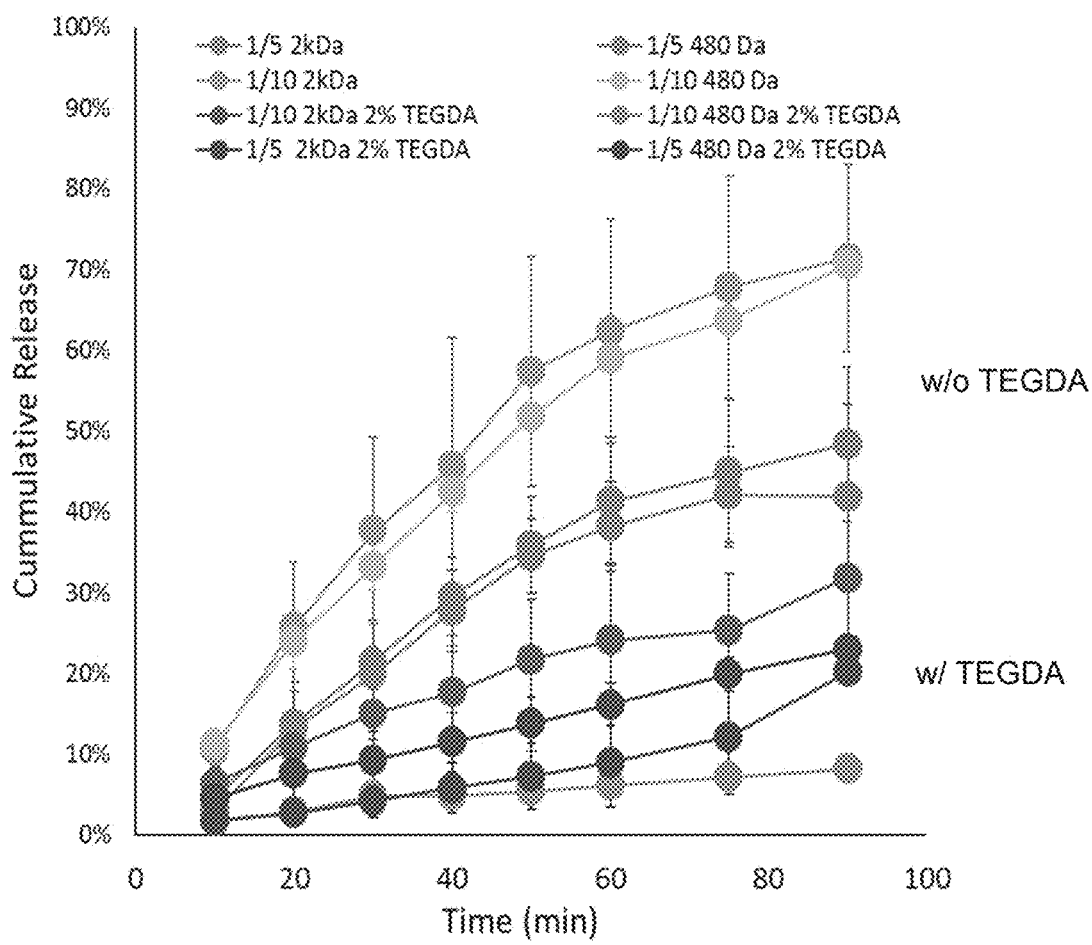
FIG. 9C illustrates a release profile of a molecule over time for various polymer membranes of the present disclosure, in accordance with embodiments.

Furthermore, as shown in FIG. 9A, without TEGDA, decreasing the molecular weight of PEGMA from 2 kDa to 480 Da results in a decrease in the tensile strength. As shown in FIG. 9B, without TEGDA, decreasing the molecular weight of PEGMA from 2 kDa to 480 Da results in a decrease in the Young's modulus. However, in crosslinked, functional membranes (e.g., electrospun polymer membranes) with TEGDA, decreasing the PEGMA molecular weight increased the Young's modulus. Thus, the molecular weight of the functional polymer can influence both the tensile strength and the Young's modulus.

As described herein, the base and/or functional polymers may each be dissolved in a desired solvent and mixed together prior to electrospinning. Polymers, such as a the base or functional polymers described herein, can be dissolved in a solvent such as dimethyl formamide (DMF), acetone, acetonitrile, aniline, n-butyl acetate, cyclohexanone, chloroform, diacetone alcohol, di(ethylene glycol), dimethyle sulfoxide, dichloromethane, ethanol, ethyl acetate, ethylene dichloride, formic acid, glycerol, methanol, methyl acetate morpholine, 2-nitropropane, 1-pentanol, n-propanol, pyridine, trifloroethanol, tetrahydrofuran, water, or any combination of solvents thereof.

Electrospinning

Polymer solutions containing any one of, or any combination of, the polymers described herein can be electrospun using an electrospinning apparatus including an emitter and a collector. Any form of fiber collected may be referred to as a membrane. Polymer solutions are sprayed from the emitter onto a collector, focused by a voltage differential between the emitter and the collector. The maximum concentration of polymer solution that can be spun can depend on viscosity and conductivity of the polymers, and can also vary with different base/functional polymers or different solvents. After satisfactory initial fiber formation, the x-axis translational stage of the emitter can be set to a repetitive linear pattern. Fibers can be collected on a rotating drum collector. Fibers can also be collected on a flat surface. Fibers can further be collected in the form of a membrane by collecting the fibers on a patterned structure. The resulting membrane can comprise a shape that is the same shape as the patterned structure.

Membranes (e.g., electrospun polymer membranes) are made of individual fibers, which are spun onto a structure, such as rotating drum collector or a patterned structure. These individual fibers can have a diameter from 180 nm to 240 nm, 520 nm to 560 nm, or equal to or less than 1000 nm. The individual fibers can have a diameter from 100 nm to 120 nm, from 120 nm to 140 nm, from 140 nm to 160 nm, from 160 nm to 180 nm, from 180 nm to 200 nm, from 200 nm to 220 nm, from 220 nm to 240 nm, from 240 nm to 260 nm, from 260 nm to 280 nm, from 280 nm to 300 nm, from 300 nm to 320 nm, from 320 nm to 340 nm, from 340 nm to 360 nm, from 360 nm to 380 nm, from 380 nm to 400 nm, from 400 nm to 420 nm, from 420 nm to 440 nm, from 440 nm to 460 nm, from 460 nm to 480 nm, from 480 nm to 500 nm, from 500 nm to 520 nm, from 520 nm to 540 nm, from 540 nm to 560 nm, from 560 nm to 580 nm, from 580 nm to 600 nm, from 600 nm to 620 nm, from 620 nm to 640 nm, from 640 nm to 660 nm, from 660 nm to 680 nm, from 680 nm to 700 nm, from 700 nm to 720 nm, from 720 nm to 740 nm, from 740 nm to 760 nm, from 760 nm to 780 nm, from 780 nm to 800 nm, from 800 nm to 820 nm, from 820 nm to 840 nm, from 840 nm to 860 nm, from 860 nm to 880 nm, from 880 nm to 900 nm, from 900 nm to 920 nm, from 920 nm to 940 nm, from 940 nm to 960 nm, from 960 nm to 980 nm, from 980 nm to 1000 nm.

Figure 1B:
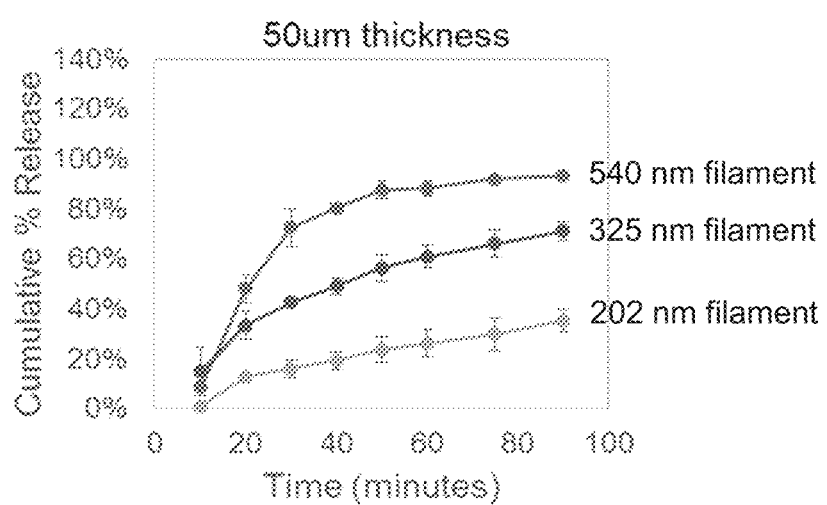
FIG. 1B illustrates a release profile of molecules in electrospun polymer membranes with differing filament diameters, in accordance with embodiments.

The diameter of the fibers can be important for the functional properties of the membrane (e.g., electrospun polymer membrane). For example, as shown in FIG. 1B, increasing the diameter of the individual fibers can increase diffusion of an encapsulated moiety from the membranes (e.g., electrospun polymer membranes), e.g., due to decreased porosity of the membrane. FIG. 1A shows membranes (e.g., electrospun polymer membranes) with individual fiber diameters of varying sizes, which can be obtained by modulating the concentration of the polymer solution prior to electrospinning and by modulating voltage. As further shown in FIG. 2A and FIG. 2B, increasing the fiber diameter to 540 nm (FIG. 2A) results in increased release of both a 4 kDa and a 500 kDa moiety, On the other hand, decreasing fiber diameter decreased the release of both a 4 kDa and a 500 kDa moiety. Reducing the diameter of individual fibers in the electrospun membrane can allow for an increase in the overall packing of the polymer matrix and interconnecting fiber filaments, thereby resulting in a concomitant increase in the porous tortuosity of the microstructure of the membrane. This increased tortuosity can decrease the release of any drugs that have been incorporated into the membrane. Thus, when designing membranes (e.g., electrospun polymer membranes) of the present disclosure, diameter can be varied to tune the desired release profile of moieties of differing molecular weights with high precision. For example, rapid release of a low flux molecular weight moiety can be achieved by increasing fiber diameter. Alternatively, dampening release of a low flux molecular weight moiety can be achieved by decreasing fiber diameter. Fiber filament diameter can be increased or decreased by modulating one or more of several of the electrospinning parameters, including but not limited to, polymer concentration in the electrospinning solution (e.g., percent (w/v) polymer in the electrospinning solution), the positive voltage, the negative voltage, the feed rate (mL/h), the distance of the needle from the fiber collector, and the time of electrospinning. Each of these parameters can be modulated either individually or in combination with any other parameter, to change the fiber filament diameter. For example, polymer concentration in the electrospinning solution can be modulated from as low as 0.01 wt % to as high as 10 wt %, from 6 wt % to 8 wt %, or from 8 wt % to 10 wt % as a parameter to change fiber filament diameter. Positive voltage can be modulated from 10 to 30, or from 20 to 22 as a parameter to change fiber filament diameter. Negative voltage can be modulated froml to 10 or can be held at 5 to change fiber filament diameter. Feed rate can be modulated from 0.1 to 5 mL/h or from 0.7 to 1.25 mL/h to change fiber filament diameter. Distance from needle to collector can be modulated from 0.1 to 30 cm or held constant at about 17.5 cm to change fiber filament diameter. Time of electrospinning can be modulated from 30 min to 504 min or can include spin times of 30 min to 60 min, 60 min to 120 min, 36 min to 72 min, 72 min to 144 min, 144 min to 252 min, or 252 min to 504 min to change fiber filament diameter.

Once electrospinning is complete and/or once crosslinking is complete, the membrane can have a thickness from 10 μm to 150 μm, or 80 μm to 120 μm. In some instances, membranes (e.g., electrospun polymer membranes) can have a thickness from 10 μm to 500 μm. For example, membranes (e.g., electrospun polymer membranes) can have a thickness from 10 μm to 20 μm, from 20 μm to 30 μm, from 30 μm to 40 μm, from 40 μm to 50 μm, from 50 μm to 60 μm, from 60 μm to 70 μm, from 70 μm to 80 μm, from 80 μm to 90 μm, from 90 μm to 100 μm, from 100 μm to 110 μm, from 110 μm to 120 μm, from 120 μm to 130 μm, from 130 μm to 140 μm, from 140 μm to 150 μm, from 150 μm to 160 μm, from 160 μm to 170 μm, from 170 μm to 180 μm, from 180 μm to 190 μm, from 190 μm to 200 μm, from 200 μm to 210 μm, from 210 μm to 220 μm, from 220 μm to 230 μm, from 230 μm to 240 μm, from 240 μm to 250 μm, from 250 μm to 260 μm, from 260 μm to 270 μm, from 270 μm to 280 μm, from 280 μm to 290 μm, from 290 μm to 300 μm, from 300 μm to 310 μm, from 310 μm to 320 μm, from 320 μm to 330 μm, from 330 μm to 340 μm, from 340 μm to 350 μm, from 350 μm to 360 μm, from 360 μm to 370 μm, from 370 μm to 380 μm, from 380 μm to 390 μm, from 390 μm to 400 μm, from 400 μm to 410 μm, from 410 μm to 420 μm, from 420 μm to 430 μm, from 430 μm to 440 μm, from 440 μm to 450 μm, from 450 μm to 460 μm, from 460 μm to 470 μm, from 470 μm to 480 μm, from 480 μm to 490 μm, from 490 μm to 500 μm. The thickness of the membrane (e.g., electrospun polymer membrane) can be used to modulate the release rate of encapsulated drugs. For example, by increasing the thickness of the membrane, encapsulated drugs can have a longer distance to traverse before exiting the polymer membrane. Thus, increasing thickness of the membrane can be another method to dampen rapid, burst release of drug from membranes. Furthermore, increasing thickness of the membrane (e.g., electrospun polymer membrane) can also result in membranes that are more bulky and have better long term mechanical strength. Increasing thickness alone can also decrease the resulting flux of incorporated drugs from the membrane. The membranes (e.g., electrospun polymer membranes) of the present disclosure can be hydrophilic. Hydrophilicity can be important in one aspect of the present invention to prevent de-wetting of the membrane surface to maintain continuous solute diffusion. In other aspects of the disclosure, the membranes (e.g., electrospun polymer membranes) described herein can also be hydrophobic.

Membranes (e.g., electrospun polymer membranes) can include functional polymers, which are subsequently crosslinked to obtain crosslinked, functional membranes (e.g., electrospun polymer membranes). Crosslinking agents and/or crosslinking initiators, further described below, can be included in the initial polymer solution. Crosslinking agents and/or crosslinking initiators, further described below, can also be incorporated by exposing membranes (e.g., electrospun polymer membranes) to a solution of a crosslinking agent and subsequently exposing the membranes (e.g., electrospun polymer membranes) to a crosslinking method, as described in detail below. Crosslinked, functional membranes (e.g., electrospun polymer membranes) can thus be obtained using these electrospinning and crosslinking synthetic strategies. For example, TEGDA, a crosslinking agent, can be dissolved in a solvent along with PAN and PEGMA, and then electrospun to generate PAN/PEGMA/TEGDA membranes. This PAN/PEGMA/TEGDA membrane can then be immersed in a solution, which can contain only a photoinitiator, and is further exposed to UV light for crosslinking, resulting in crosslinked PAN/PEGMA/TEGDA membranes. Alternatively, PAN and PEGMA can be dissolved in a solvent and electrospun to generate PAN/PEGMA membranes. This electrospun membrane is immersed in a solution, which can contain a crosslinker (e.g., TEGDA) and a photoinitiator. The membrane is then exposed to UV light to form the crosslinked PAN/PEGMA/TEGDA membrane. The crosslinked, functional membranes (e.g., electrospun polymer membranes) are also described herein as having a "coating" or an "overcoating." Membranes (e.g., electrospun polymer membranes) of the present disclosure can also not be crosslinked, and thus can be obtained without a coating.

Membranes (e.g., electrospun polymer membranes) (e.g., whether crosslinked or not) can be configured to allow passage of cells. For example, membranes (e.g., electrospun polymer membranes), before or after crosslinking, can be designed to have a pore size equal to or more than about 5 μm. The membranes (e.g., electrospun polymer membranes) can also be configured to block passage of cells. For example, membranes (e.g., electrospun polymer membranes), before or after crosslinking, can be designed to have a pore size equal to or more than about 3 μm. The pore size of the membrane (e.g., electrospun polymer membrane) can be anywhere between 10 nm and 10 μm. For example, the pore size can be from 10 nm to 50 nm, from 50 nm to 100 nm, from 100 nm to 150 nm, from 150 nm to 200 nm, from 200 nm to 250 nm, from 250 nm to 300 nm, from 300 nm to 350 nm, from 350 nm to 400 nm, from 400 nm to 450 nm, from 450 nm to 500 nm, from 500 nm to 550 nm, from 550 nm to 600 nm, from 600 nm to 650 nm, from 650 nm to 700 nm, from 700 nm to 750 nm, from 750 nm to 800 nm, from 800 nm to 850 nm, from 850 nm to 900 nm, from 900 nm to 950 nm, from 950 nm to 1 μm, from 1 μm to 2 μm, from 2 μm to 3 μm, from 3 μm to 4 μm, from 4 μm to 5 μm, from 5 μm to 6 μm, from 6 μm to 7 μm, from 7 μm to 8 μm, from 8 μm to 9 μm, from 9 μm to 10 μm. In some instances, membranes with a 5 μm or smaller pore size can result in limiting passage of cells and increasing the pore size can increase cell invasion or escape.

Membranes (e.g., electrospun polymer membranes) (e.g., whether crosslinked or not) of the present disclosure can have superior mechanical properties that allow them to be implanted in a subject for long periods of time without loss of structural integrity. These membranes can be designed to obtain a specific tensile strength or Young's modulus. For example, the tensile strength of a membrane (e.g., electrospun polymer membrane) of the present disclosure can be equal to or greater than about 1 MPa. The tensile strength of a membrane (e.g., electrospun polymer membrane) of the present disclosure can be from 0.5 MPa to 1 MPa, from 1 MPa to 1.5 MPa, from 1.5 MPa to 2 MPa, from 2 MPa to 2.5 MPa, from 2.5 MPa to 3 MPa, from 3 MPa to 3.5 MPa, from 3.5 MPa to 4 MPa, from 4 MPa to 4.5 MPa, from 4.5 MPa to 5 MPa, from 5 MPa to 5.5 MPa, from 5.5 MPa to 6 MPa, from 6 MPa to 6.5 MPa, from 6.5 MPa to 7 MPa, from 7 MPa to 7.5 MPa, from 7.5 MPa to 8 MPa, from 8 MPa to 8.5 MPa, from 8.5 MPa to 9 MPa, from 9 MPa to 9.5 MPa, from 9.5 MPa to 10 MPa, from 10 MPa to 20 Mpa, from 20 Mpa to 30 Mpa, from 30 Mpa to 40 Mpa, from 40 Mpa to 50 Mpa, from 50 Mpa to 60 Mpa, from 60 Mpa to 70 Mpa, from 70 Mpa to 80 Mpa, from 80 Mpa to 90 Mpa, or from 90 Mpa to 100 Mpa. The Young's modulus of a membrane (e.g., electrospun polymer membrane) of the present disclosure can be equal to or greater than about 30 MPa. The Young's modulus of a membrane (e.g., electrospun polymer membrane) of the present disclosure can be from 10 MPa to 100 MPa. For example, the Young's modulus can be from 10 MPa to 15 MPa, from 15 MPa to 20 MPa, from 20 MPa to 25 MPa, from 25 MPa to 30 MPa, from 30 MPa to 35 MPa, from 35 MPa to 40 MPa, from 40 MPa to 45 MPa, from 45 MPa to 50 MPa, from 50 MPa to 55 MPa, from 55 MPa to 60 MPa, from 60 MPa to 65 MPa, from 65 MPa to 70 MPa, from 70 MPa to 75 MPa, from 75 MPa to 80 MPa, from 80 MPa to 85 MPa, from 85 MPa to 90 MPa, from 90 MPa to 95 MPa, from 95 MPa to 100 MPa, from 100 MPa to 150 MPa, from 150 MPa to 200 MPa, from 200 MPa to 250 MPa, from 250 MPa to 300 MPa, from 300 MPa to 350 MPa, from 350 MPa to 400 MPa, from 400 MPa to 450 MPa, from 450 MPa to 500 MPa, from 500 MPa to 600 MPa, from 600 MPa to 700 MPa, from 700 MPa to 800 MPa, from 800 MPa to 900 MPa, from 900 MPa to 1,000 MPa, from 1,000 MPa to 2,000 MPa, from 2,000 MPa to 3,000 MPa, from 3,000 MPa to 4,000 MPa, from 4,000 MPa to 5,000 MPa, from 5,000 MPa to 6,000 MPa, from 6,000 MPa to 7,000 MPa, from 7,000 MPa to 8,000 MPa, from 8,000 MPa to 9,000 MPa, from 9,000 MPa to 10,000 MPa, from 10,000 MPa to 20,000 MPa, from 20,000 MPa to 30,000 MPa, from 30,000 MPa to 40,000 MPa, from 40,000 MPa to 50,000 MPa, from 50,000 MPa to 60,000 MPa, from 60,000 MPa to 70,000 MPa, from 70,000 MPa to 80,000 MPa, from 80,000 MPa to 90,000 MPa, or from 90,000 MPa to 100,000 MPa.

Crosslinking Techniques

Various methods of crosslinking can be employed to obtain the functional, crosslinked membranes (e.g., electrospun polymer membranes) of the present disclosure. These methods include, but are not limited to, UV crosslinking with photoinitiators, heat crosslinking with heat crosslinking initiators, transition metals, and other chemical methods of crosslinking. Crosslinking agents can include polymer crosslinkers or other molecular structures that can be used in one of the crosslinking reactions described below to form new bonds between reactive groups on functional polymers. In other words, crosslinking agents can be used to chemically link reactive groups on functional polymers in the membranes (e.g., electrospun polymer membranes) of the present disclosure. This can result in improved mechanical properties, better device integrity, modulation of porosity and, as a result, the modulation of the diffusion rates of various molecular weight moieties through the membranes (e.g., electrospun polymer membranes).

Crosslinking agents can include any functional polymer, as described above, or other chemical moieties. For example, a crosslinking agent can be a functional problem and can include, but is not limited to, polyethylene glycol (PEG), poly(ethylene glycol) methacylate (PEGMA), poly(ethylene glycol) diacylate (PEGDA), tetraethyleneglycol diacrylate (TEGDA), or any combination thereof. Crosslinking agents can also include bis(2-(succinimidyl-oxycarbonyloxyl)ethyl) sulfone, di(n-succinimidyl)glutarate, disuccinimidyl tartrate], 3,3'-dithiobis(sulfosuccinimidyl propionate, p-phenylene diisothiocyanate, sebacic acid bis (N-succinimidyl) ester, suberic acid bis(N-hydroxy succinimide ester), APN-CHO, bromoacetic acid N-hydroxy succinimide ester, CBTF, iodoacetic acid N-hydroxysuccinimide ester, maleimide-PEG-succinimidyl ester, maleimidoacetic acid N-hydroxysuccinimide ester, adipic acid dihydrazide, alkyne-PEG-maleimide, APN-amine, APN-azide, APN-BCN, APN-COCl, biotin-benzyl-tetrazine, biotin-PEG-TPG, 1,11-diazido-3,6,9-trioxaundecane, dibenzocyclooctyne-N-hydroxy succinimidyl ester, dibenzocyclooctyne-maleimide, dibenzocyclooctyne-PEG-maleimide, 4-(maleinimido)phenyl isocyanate purum, 4,4'-methylenebis(phenylisocyanate), 3-(2-pyridyldithio)propionyl hydrazide, propargyl-N-hydroxylsuccinimidyl ester, PTAD-azide, sulfo-NHS-diazirine) (sulfosuccinimidyl 4,4'-azipentanoate, 4-(N-maleimido)benzophenone, 4-azidopehenacyl bromide, 5-azido-2-nitriobenzoic acid N-hydroxy succinimide ester, succinimidyl-[4-(psoralen-8-yloxy)]butyrate, 4-benzoylbenzoic acid N-succinimidyl ester, 1,4-bis [3-(2-pyridyldithio)propionamido]butane, bis-maleimidoethane, dithio-bis-maleimidoethane and more.

Crosslinking agents can be included at 2% (w/v) or 7% (w/v). In some instances, crosslinking agents can be included at 0.01% (w/v), 0.1% (w/v), 0.5% (w/v), 1% (w/v), 10% (w/v), 20% (w/v). In some instances, crosslinking agents can be included from about 0.01% (w/v) to about 20% (w/v), from 0.01% (w/v) to about 0.05% (w/v), from 0.05% (w/v) to about 0.1% (w/v), from 0.1% (w/v) to about 0.2% (w/v), from 0.2% (w/v) to about 0.3% (w/v), from 0.3% (w/v) to about 0.4% (w/v), from 0.4% (w/v) to about 0.5% (w/v), from 0.5% (w/v) to about 1% (w/v), from 1% (w/v) to about 2% (w/v), from 2% (w/v) to about 3% (w/v), from 3% (w/v) to about 4% (w/v), from 4% (w/v) to about 5% (w/v), from 5% (w/v) to about 10% (w/v), from 10% (w/v) to about 15% (w/v), or from 15% (w/v) to about 20% (w/v).

UV Photoinitiators. Ultraviolet (UV) photoinitiators can be employed to crosslink the functional membranes (e.g., electrospun polymer membranes) of the present disclosure. Photoinitiators can be used to catalyze crosslinking upon exposure to UV light. Photoinitiators can be incorporated into the initial polymer solution, which is subsequently electrospun into a functional membrane (e.g., electrospun polymer membrane) and placed under UV light to initiate crosslinking. Photoinitiators can also be incorporated by soaking functional membranes (e.g., electrospun polymer membranes) in a solution that contains the photoinitiator. Functional membranes (e.g., electrospun polymer membranes) are then dried and placed under UV light to initiate crosslinking. Suitable photoinitiators compatible with the present disclosure and which can be incorporated into functional membranes (e.g., electrospun polymer membranes) include, but are not limited to, acetophenone, anisoin, anthraquinone, benzyl, benzoin, benzene tricarbonylchromium, benzoin ethyl ether, benzoin isobutyl ether, benzoin methyl ether, benzophenone, 3,3',4,4'-benzophenonetetracarboxylic dianhydride, 4-benzoylbiphenyl, 2-benzyl-2-(dimethylamino)-4'-morpholinobutyrophenone, 4,4'-bis(diethylamino)benzophenone, camphorquinone, 2-chlorothioxanthen-9-one, (cumene)cyclopentadienyliron (II) hexafluorophosphate, dibenzosuberenone, 2,2-diethoxyacetophenone, 4,4'-dihydroxybenzophenone, 2,2-dimethoxy-2-phenylacetophenone, 4-(dimethylamino)benzophenone, 4,4'-dimethylbenzil, 2,5-dimethylbenzonphenone, 3,4-dimethylbenzophenone, diphenyl(2,4,6-trimethylbenzoyl)phosphine oxide, 4'-ethoxyacetophenone, 2-ethylanthraquinone, ferrocene, 3-hydroxyacetophenone, 4-hydroxyacetophenone, 1-hydroxycyclohexyl phenyl ketone, 2-hydroxy-2-methylpropiophenone, 2-methylbenzophenone, 3-methylbenzophenone, methybenzoylformate, 2-methyl-4'-(methylthio)-2-morpholinoproiophenone, phenanthrenequinone, 4'-phenoxyacetophenone, thioxanthene-9-one, triarylsulfonium, hexafluoroantimonate salts, triarylsulfonium hexafluorophosphate salts and more.

Figure 8A:
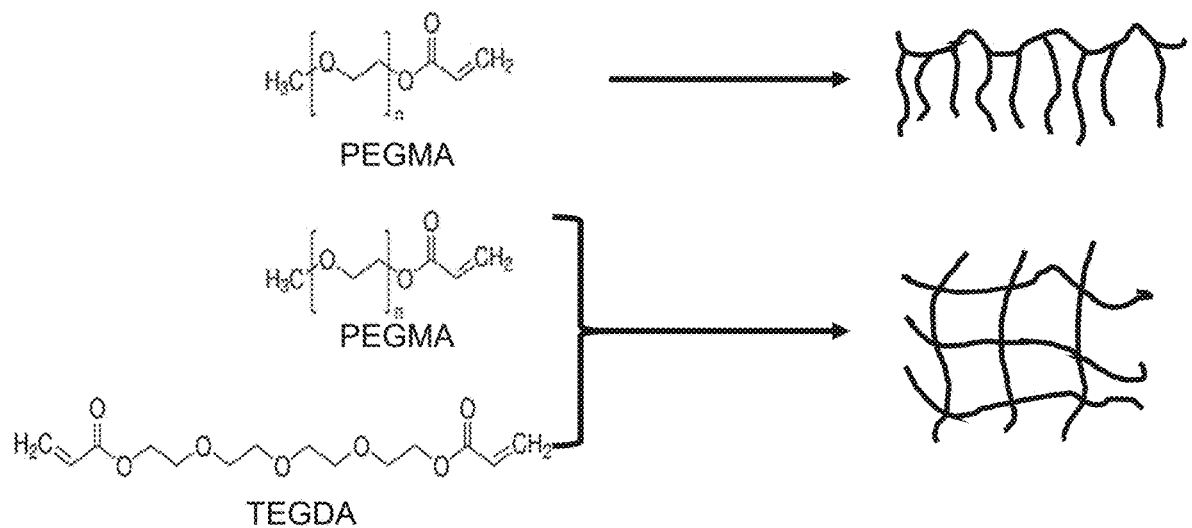
FIG. 8A illustrates how a photoinitiator and ultraviolet light (UV) affects structure of PEGMA and PEGMA with TEGDA, a secondary crosslinker, TEGDA, in accordance with embodiments.
Figure 8B:
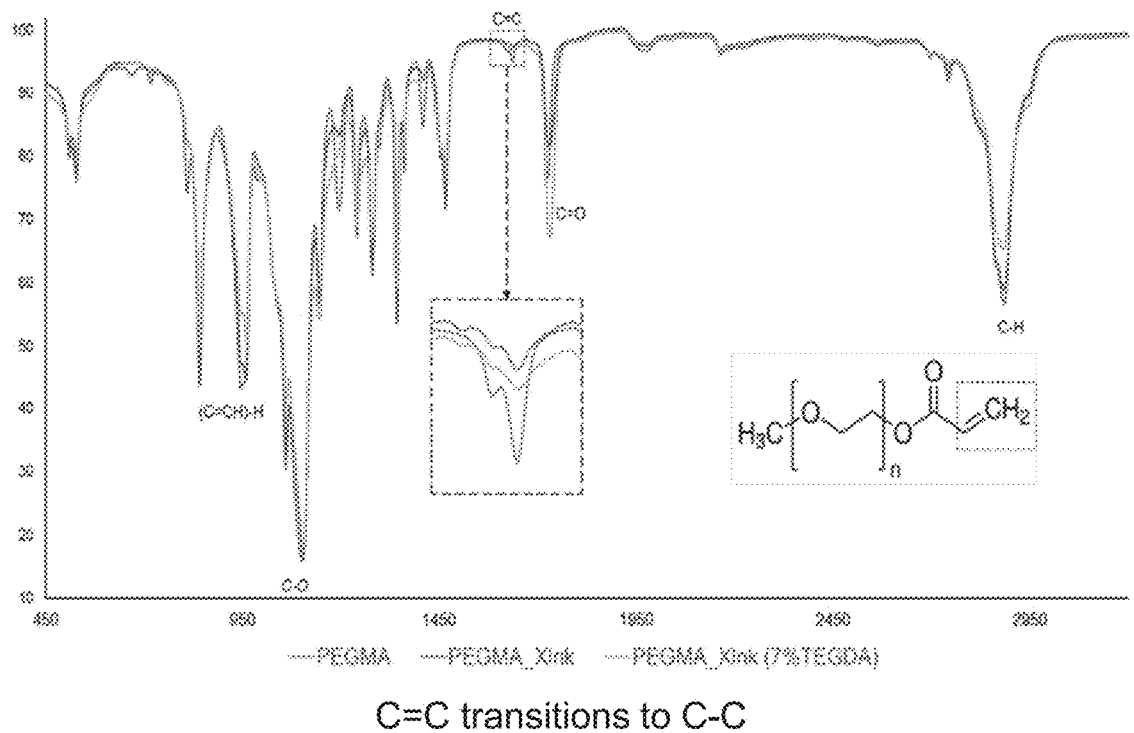
FIG. 8B illustrates Fourier transform infrared spectroscopy (FTIR) results showing the transition from C=C bonds to C—C bonds in the PEGMA polymer upon crosslinking, in accordance with embodiments.

FIG. 8A shows a schematic of an exemplary crosslinked, functional electrospun polymer membrane of the present disclosure made by UV crosslinking. PEGMA (a functional polymer) or PEGMA and TEGDA (a functional polymer and crosslinker polymer) can be incorporated in membranes (e.g., electrospun polymer membranes) and exposed to a photoinitiator and UV light to crosslink the electrospun polymer device. FIG. 8B further confirms that upon UV crosslinking, carbon-carbon double bonds are converted to carbon-carbon single bonds, thereby demonstrating successful crosslinking of functional polymers.

Figure 7A:
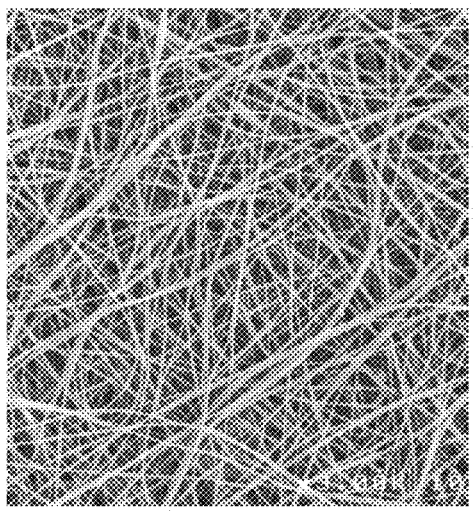
FIG. 7A illustrates an SEM image of a non-crosslinked, electrospun polymer membrane, in accordance with embodiments.
Figure 7B:
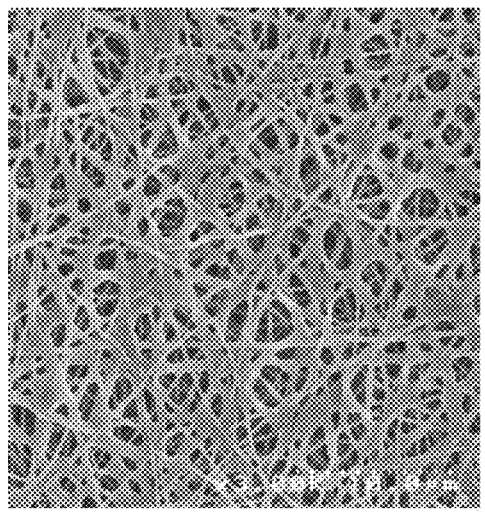
FIG. 7B illustrates an SEM image of a crosslinked, electrospun polymer membrane, in accordance with embodiments.
Figure 7C:
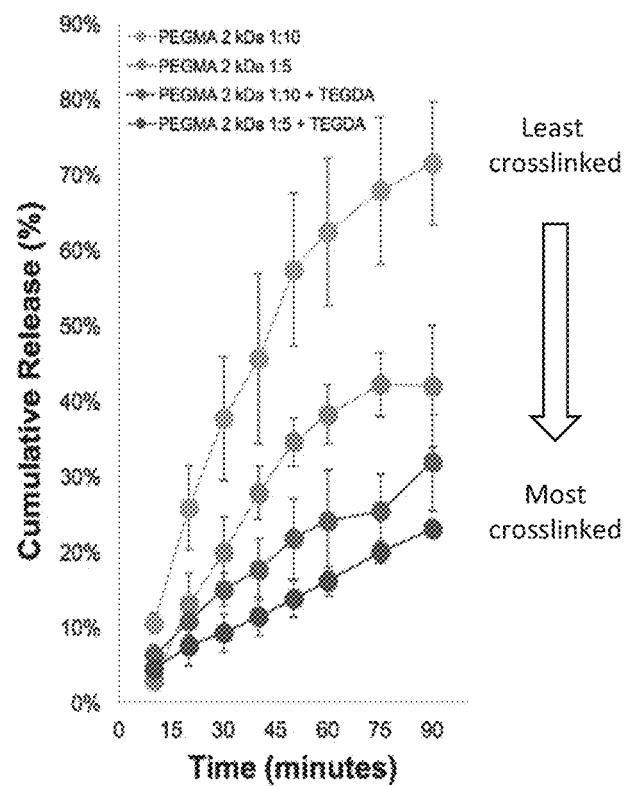
FIG. 7C shows a release profile of a molecule from electrospun polymer membranes of the present disclosure varying in a degree of crosslinking, in accordance with embodiments.

Another example of a crosslinked, functional membrane (e.g., electrospun polymer membrane) comprising of PAN and PEGMA is shown in FIG. 7. FIG. 7A shows a membrane (e.g., electrospun polymer membrane) prior to UV crosslinking and FIG. 7B shows a membrane (e.g., electrospun polymer membrane) after crosslinking with the TEGDA crosslinking agent. As can be seen from a comparison of FIG. 7A and FIG. 7B, post-UV crosslinking, the porosity of the polymer membrane decreases and the polymers appear to be more webbed. FIG. 7C demonstrates modulation of release of a 4 kDa FITC-dextran molecule, representative of insulin, from PAN/PEGMA membranes (e.g., electrospun polymer membranes) at different ratios of base polymer to functional polymer and in the presence of TEGDA. This figure shows that the UV crosslinking method described above can be effectively used to dampen burst release of an encapsulated drug. Thus, depending on the desired flux of the low molecular weight therapeutic moiety (e.g., the desired $D_{first}$ of the low molecular weight therapeutic moiety), UV-based crosslinking of functional, electrospun polymers can be employed to modulate $D_{first}$.

FIG. 9A and FIG. 9B illustrate some of the improvements in mechanical strength and device integrity imparted by UV-based crosslinking of functional membranes (e.g., electrospun polymer membranes). As shown in these figures, the overall tensile strength and the Young's modulus can be improved by inclusion of a crosslinking agent such as TEGDA. FIG. 9C further shows modulation of release of a low molecular weight therapeutic moiety (e.g., the desired $D_{first}$ of the low molecular weight therapeutic moiety) from crosslinked, functional membranes (e.g., electrospun polymer membranes) of the present disclosure. This figure illustrates that overall dampening in the $D_{first}$ coefficient of the present disclosure can be achieved by UV-based crosslinking.

Heat Initiators. Heat initiators can be employed to crosslink the functional membranes (e.g., electrospun polymer membranes) of the present disclosure. Heat initiators can be used to catalyze crosslinking upon exposure to heat. The temperature used in the present disclosure to catalyze the heat-mediated crosslinking can be from 40° C. to 100° C. The temperature used in the present disclosure to catalyze the heat-mediated crosslinking can be from 40° C. to 45° C., from 45° C. to 50° C., from 50° C. to 55° C., from 55° C. to 60° C., from 60° C. to 65° C., from 65° C. to 70° C., from 70° C. to 75° C., from 75° C. to 80° C., from 80° C. to 85° C., from 85° C. to 90° C., from 90° C. to 95° C., or from 95° C. to 100° C. Heat initiators can be incorporated into the initial polymer solution, which is subsequently electrospun into a functional membrane (e.g., electrospun polymer membrane) and heated to initiate crosslinking. Heat initiators can also be incorporated by soaking functional membranes (e.g., electrospun polymer membranes) in a solution that contains the photoinitiator. Functional membranes (e.g., electrospun polymer membranes) are then dried and placed under UV light to initiate crosslinking.

Suitable heat initiators compatible with the present disclosure and which can be incorporated into functional membranes (e.g., electrospun polymer membranes) include, but are not limited to, ammonia persulfate, tert-amyl peroxybenzoate, 4,4-azobis(4-cyanovaleric acid), 1,1'-azobis(cyclohexanecarbonitrile), 2,2'-azobissobutyronitrile, benzoyl peroxide, 2,2-bis(tert-butylperoxy)butane, 1,1-bis(tert-butylperoxy)cyclohexane, 2,5-bis(tert-butylperoxy)-2,5-dimethylhexane, 2,5-bis(tert-butylperoxy)-2,5-dimethyl-3-hexyne, bis(1-(tert-butylperoxyl)-1-methylethyl)benzene, 1,1-bis(tert-butylperoxy)-3,3,5-trimethylcyclohexane, tert-butyl hydroperoxide, tert-butyl peracetate, tert-butyl peroxide, tert-butyl peroxybenzoate, tert-butylperoxy isopropyl carbonate, cumene, hydroperoxide, cyclohexanone peroxide, dicumyl peroxide, lauroyl peroxide, 2,4-pentanedione peroxide, peracetic acid, potassium persulfate and more.

Transition Metals. Transition metals can be employed to crosslink the functional membranes (e.g., electrospun polymer membranes) of the present disclosure. Transition metals can interact with reactive groups on functional polymers to coordinate crosslinking of functional membranes (e.g., electrospun polymer membranes). Transition metals can be incorporated by soaking functional membranes (e.g., electrospun polymer membranes) in a solution to initiate. Suitable transition metals compatible with the present disclosure and which can be incorporated into functional membranes (e.g., electrospun polymer membranes) include, but are not limited to, ions of beryllium, magnesium, calcium, barium, manganese, copper, iron and more.

Diffusion Ratios

The present disclosure provides membranes (e.g., electrospun polymer membranes), which can be characterized by a ratio of a first diffusion coefficient ($D_{first}$) and a second diffusion coefficient ($D_{second}$). $D_{first}$ and $D_{second}$ correspond to a first moiety with a first molecular weight and a second moiety with a second molecular weight moiety. In some instances, the first moiety may be a moiety disposed or comprised within the membrane, such as a therapeutic moiety. It may be desirable to be able to provide effective release or diffusion of the first moiety out of or across the membrane. In some instances, the second moiety may be a moiety disposed or comprised outside the membrane (e.g., within a host body). It may be desirable to be able to prevent or dissuade diffusion of the second moiety into or across the membrane. As one example, the first moiety may be insulin and the second moiety may be IgG.

The first molecular weight moiety can have a molecular weight from 100 Da to 100,000 Da. In some instances, the first molecular weight moiety can have a molecular weight equal to or less than about 50 Da, 100 Da, 200 Da, 400 Da, 600 Da, 800 Da, 1000 Da, 1500 Da, 2000 Da, 2500 Da, 3000 Da, 3500 Da, 4000 Da, 5000 Da, 6000 Da, 7000 Da, 8000 Da, 9000 Da, 10000 Da, 12000 Da, 14000 Da, 16000 Da, 18000 Da, 20000 Da, 25000 Da, 30000 Da, 35000 Da, 40000 Da, 45000 Da, 50000 Da, 55000 Da, 60000 Da, 65000 Da, 70000 Da, 75000 Da, 80000 Da, 85000 Da, 90000 Da, 95000 Da, 100000 Da, 110000 Da, 120000 Da, 130000 Da, 140000 Da, or 150000 Da. In some instances, the first molecular weight moiety can have a molecular weight equal to or more than about 50 Da, 100 Da, 200 Da, 400 Da, 600 Da, 800 Da, 1000 Da, 1500 Da, 2000 Da, 2500 Da, 3000 Da, 3500 Da, 4000 Da, 5000 Da, 6000 Da, 7000 Da, 8000 Da, 9000 Da, 10000 Da, 12000 Da, 14000 Da, 16000 Da, 18000 Da, 20000 Da, 25000 Da, 30000 Da, 35000 Da, 40000 Da, 45000 Da, 50000 Da, 55000 Da, 60000 Da, 65000 Da, 70000 Da, 75000 Da, 80000 Da, 85000 Da, 90000 Da, 95000 Da, 100000 Da, 110000 Da, 120000 Da, 130000 Da, 140000 Da, or 150000 Da. In some instances, the first molecular weight moiety can have a molecular weight in between any of the following values: 50 Da, 100 Da, 200 Da, 400 Da, 600 Da, 800 Da, 1000 Da, 1500 Da, 2000 Da, 2500 Da, 3000 Da, 3500 Da, 4000 Da, 5000 Da, 6000 Da, 7000 Da, 8000 Da, 9000 Da, 10000 Da, 12000 Da, 14000 Da, 16000 Da, 18000 Da, 20000 Da, 25000 Da, 30000 Da, 35000 Da, 40000 Da, 45000 Da, 50000 Da, 55000 Da, 60000 Da, 65000 Da, 70000 Da, 75000 Da, 80000 Da, 85000 Da, 90000 Da, 95000 Da, 100000 Da, 110000 Da, 120000 Da, 130000 Da, 140000 Da, or 150000 Da.

The second molecular weight moiety can have a molecular weight from 50000 Da to 1,000,000 Da. In some instances, the second molecular weight moiety can have a molecular weight equal to or less than about 50000 Da, 75000 Da, 100000 Da, 120000 Da, 140000 Da, 160000 Da, 180000 Da, 200000 Da, 250000 Da, 300000 Da, 350000 Da, 400000 Da, 450000 Da, 500000 Da, 600000 Da, 700000 Da, 800000 Da, 900000 Da, or 1000000 Da. In some instances, the second molecular weight moiety can have a molecular weight equal to or more than about 50000 Da, 75000 Da, 100000 Da, 120000 Da, 140000 Da, 160000 Da, 180000 Da, 200000 Da, 250000 Da, 300000 Da, 350000 Da, 400000 Da, 450000 Da, 500000 Da, 600000 Da, 700000 Da, 800000 Da, 900000 Da, or 1000000 Da. In some instances, the second molecular weight moiety can have a molecular weight in between any of the following values: 50000 Da, 75000 Da, 100000 Da, 120000 Da, 140000 Da, 160000 Da, 180000 Da, 200000 Da, 250000 Da, 300000 Da, 350000 Da, 400000 Da, 450000 Da, 500000 Da, 600000 Da, 700000 Da, 800000 Da, 900000 Da, or 1000000 Da.

A ratio of the molecular weights of the second molecular weight moiety to the first molecular weight moiety can be within 1 to 100. In some instances, the ratio of the molecular weights of the second molecular weight moiety to the first molecular weight moiety can be equal to or greater than about 1, 2, 3, 4, 5, 6, 7, 8, 9, 10, 12, 14, 16, 18, 20, 24, 26, 28, 30, 35, 40, 45, 50, 60, 70, 80, 90, or 100. In some instances, the ratio of the molecular weights of the second molecular weight moiety to the first molecular weight moiety can be equal to or less than about 1, 2, 3, 4, 5, 6, 7, 8, 9, 10, 12, 14, 16, 18, 20, 24, 26, 28, 30, 35, 40, 45, 50, 60, 70, 80, 90, or 100. In some instances, the ratio of the molecular weights of the second molecular weight moiety to the first molecular weight moiety can be within any of the following values: 1, 2, 3, 4, 5, 6, 7, 8, 9, 10, 12, 14, 16, 18, 20, 24, 26, 28, 30, 35, 40, 45, 50, 60, 70, 80, 90, or 100.

The ratio of the molecular weights of the second molecular weight moiety to the first molecular weight moiety can be equal to or greater than about 10. The ratio of the second molecular weight moiety to the first molecular weight moiety can also be equal to or greater than about 20. The ratio of the second molecular weight moiety to the first molecular weight moiety can also be equal to or greater than about 30. The first molecular weight moiety can be less than about 10 kDa. The second molecular weight moiety can be greater than about 100 kDa. In exemplary embodiments of the present disclosure, the first molecular weight moiety can be equal to about 4 kDa and the second molecular weight moiety can be equal to about 150 kDa.

Figure 3A:
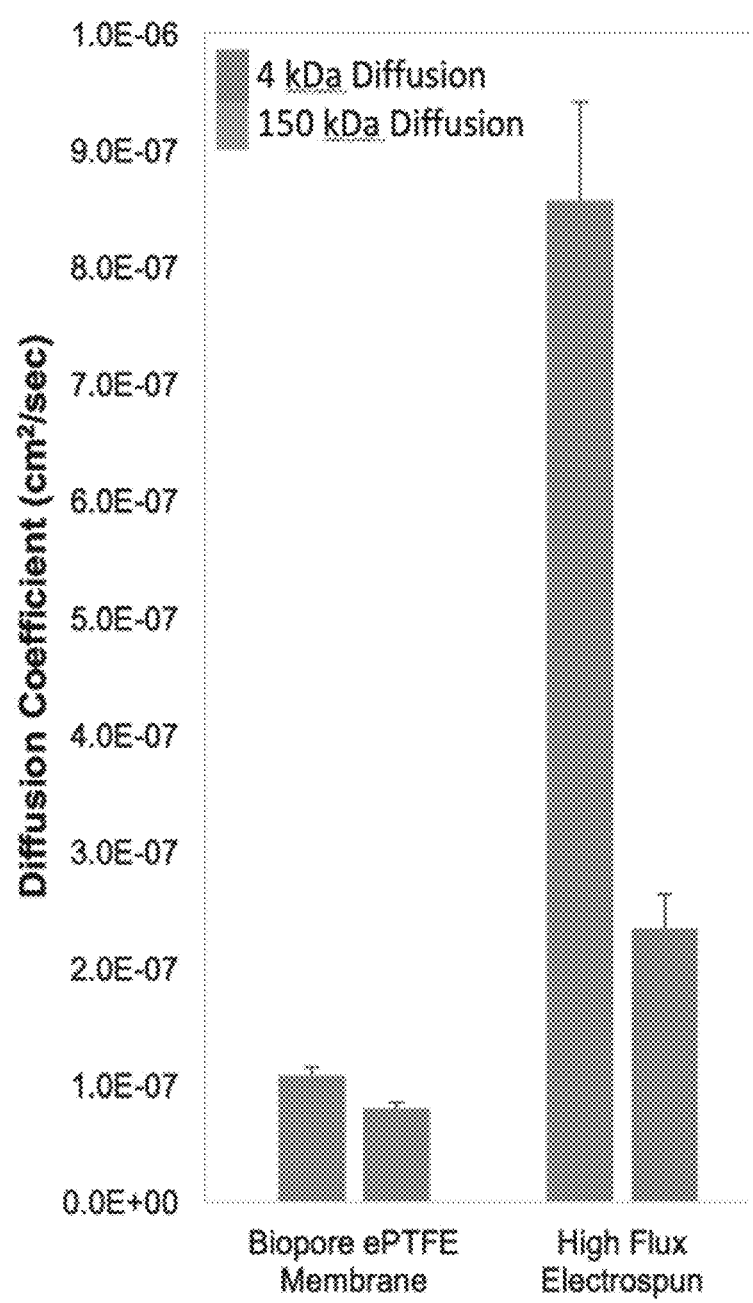
FIG. 3A illustrates the diffusion coefficient of an electrospun polymer membranes fabricated from poly(acrylonitrile)(PAN) compared to a Biopore ePTFE membrane, in accordance with embodiments.

The membrane (e.g., electrospun polymer membrane) can comprise a $D_{first}/D_{second}$ ratio equal to or greater than about 2, 3, 4, 5, 6, 7, 8, 9, 10, 12, 14, 16, 18, 20, 22, 24, 26, 28, 30, 35, 40, or 50. For example, membranes (e.g., electrospun polymer membranes) with a high $D_{first}/D_{second}$ ratio (high flux electrospun polymer membrane) are shown in FIG. 3A. This figure compares commercially available membranes and other formulations of membranes to high flux membranes (e.g., electrospun polymer membranes), which have not been crosslinked. The high flux membrane (e.g., electrospun polymer membrane) exhibited a $D_{first}$ ($D_{4\ kDa}$) of ~8.5×10$^7$ cm$^2$/sec and a $D_{second}$ ($D_{150\ kDa}$) of ~2×10$^7$ cm$^2$/sec. In this example, the $D_{first}/D_{second}$ ratio was ~4.

$D_{first}$ can be equal to or more than $10^{-7}$ cm$^2$/sec and can correspond to the diffusion coefficient for insulin. $D_{second}$ can correspond to a diffusion coefficient for IgG. The $D_{first}/D_{second}$ ratio of the membrane (e.g., electrospun polymer membrane) can be imparted by crosslinking of functional membranes (e.g., electrospun polymer membranes). Alternatively, the $D_{first}/D_{second}$ ratio can define a characteristic of any membrane (e.g., electrospun polymer membrane) of the present disclosure. For example, the $D_{first}/D_{second}$ ratio can also define a characteristic of membranes (e.g., electrospun polymer membranes) that have not been crosslinked. The $D_{first}/D_{second}$ ratio can be controlled by a variety of techniques presented herein including, varying the molecular weight of the base polymer(s), varying the molecular weight of the functional polymer(s), selecting particular base polymers and/or functional polymers that have increased interactions or reduced interactions with the first and second moiety, changing the pore size of the membrane (e.g., electrospun polymer membrane), changing the diameter of individual fibers in the membranes (e.g., electrospun polymer membranes), amount of crosslinker, time of crosslinking, and other variables.

The $D_{first}/D_{second}$ ratio of a membrane (e.g., electrospun polymer membrane) of the present disclosure can be designed based on the desired application. For example, a membrane (e.g., electrospun polymer membrane), including a crosslinked, functional membrane (e.g., electrospun polymer membrane), can be designed for the purposes of implantation and long-term insulin delivery to a subject for the purposes of treating diabetes. In this example, the crosslinked, functional membrane (e.g., electrospun polymer membrane), can be designed to encapsulate engineered stem cells, which secrete insulin. Thus, the crosslinked, functional membrane (e.g., electrospun polymer membrane) can be designed to provide high flux of secreted insulin ($D_{first}$) from the membranes and restrict diffusion of encapsulated cells ($D_{second}$) or host moieties ($D_{second}$), such as host cells or host proteins, or any combination thereof by selecting particular polymers, crosslinkers, crosslinker concentration, crosslinking time, membrane porosity, fiber diameter, or any combination thereof. In another example, a crosslinked, functional membrane (e.g., electrospun polymer membrane) can be designed to encapsulate insulin first. Here, the crosslinked, functional membrane (e.g., electrospun polymer membrane) can be designed to provide high flux of insulin ($D_{first}$) from the membranes while restricting diffusion of host moieties ($D_{second}$), such as host cells or host proteins.

Therapeutic Agents

The membranes (e.g., electrospun polymer membranes) disclosed herein, whether crosslinked or not, can be loaded with therapeutic agents. Therapeutic agents of the present disclosure can include moieties that exhibit a therapeutic benefit either indirectly or directly. Therapeutic agents can be embedded in the membrane (e.g., electrospun polymer membrane) by incorporation into the initial polymer solution, which is subsequently electrospun into a functional membrane (e.g., electrospun polymer membrane). Therapeutic agents can also be incorporated by soaking crosslinked, functional membranes (e.g., electrospun polymer membranes) in a solution that contains the therapeutic agent.

Cells. Therapeutic agents that impart an indirect therapeutic benefit can include cells, such as cells that have been engineered to secrete a drug, which has a therapeutic benefit. For example, cells can be engineered to produce insulin. For example, the cells can be stem cell-derived beta islet cells engineered to express insulin. After incorporation into cross-linked, functional membranes (e.g., electrospun polymer membranes), cells secrete insulin after implantation of membranes in a subject. In some cases, the cells can be a population of non-native pancreatic β cells. The cells can be stem cell-derived islet cells that contain several types of cells: alpha-2 cells, which produce the hormone glucagon; β cells (also referred to herein as "pancreatic β cells"), which manufacture the hormone insulin; and alpha-1 cells, which produce the regulatory agent somatostatin.

The cells can be mature cells. The cells can exhibit an in vitro glucose stimulated insulin secretion (GSIS) response. The cells can exhibit an in vivo GSIS response. The cells can exhibit in vitro glucose stimulated insulin secretion (GSIS) responses. The cells can exhibit in vitro and in vivo glucose stimulated insulin secretion (GSIS) responses. The cells can exhibit a GSIS response to at least one glucose challenge. The cells can exhibit a GSIS response to at least two sequential glucose challenges. The cells can exhibit a GSIS response to at least three sequential glucose challenges. The GSIS response can be observed immediately upon transplanting the cells into a human or animal. The GSIS response can be observed within approximately 24 hours of transplanting the cell into a human or animal. The GSIS response can be observed within approximately two weeks of transplanting the cell into a human or animal.

The cells can be stem cell-derived β cells. The cells can be non-native pancreatic β cells. The stem cell-derived β cells can be non-native. As used herein, "non-native" means that the cells are markedly different in certain aspects (e.g., gene expression profiles) from cells which exist in nature, e.g., native β cells. For example, the non-native pancreatic β cells may not express somatostatin, glucagon, or both.

The may not express at least one marker (e.g., a marker not expressed by endogenous mature pancreatic β cells) selected from the group consisting of a) a hormone selected from the group consisting of i) glucagon (GCG), and ii) somatostatin (SST); b) an acinar cell marker selected from the group consisting of i) amylase, and ii) carboxypeptdase A (CPA1), c) an a cell marker selected from the group consisting of i) GCG, Arx, Irx1, and Irx2, d) a ductal cell marker selected from the group consisting of i) CFTR, and ii) Sox9. The cells can be differentiated in vitro from any starting cell as the invention is not intended to be limited by the starting cell from which the cells are derived. Exemplary starting cells include, without limitation, insulin-positive endocrine cells or any precursor thereof such as a Nkx6-1-positive pancreatic progenitor cell, a Pdx1-positive pancreatic progenitor cell, and a pluripotent stem cell, an embryonic stem cell, and induced pluripotent stem cell. The cells can be differentiated in vitro from a reprogrammed cell, a partially reprogrammed cell (i.e., a somatic cell, e.g., a fibroblast which has been partially reprogrammed such that it exists in an intermediate state between an induced pluripotency cell and the somatic cell from which it has been derived), or a transdifferentiated cell. The cells can be differentiated in vitro from an insulin-positive endocrine cell or a precursor thereof. The cells can be differentiated in vitro from a precursor selected from the group consisting of a Nkx6-1-positive pancreatic progenitor cell, a Pdx1-positive pancreatic progenitor cell, and a pluripotent stem cell. The pluripotent stem cell can be selected from the group consisting of an embryonic stem cell and induced pluripotent stem cell. The cell or the pluripotent stem cell from which the cells are derived from is a human cell.

The cells can be exocrine cells (e.g., cell of an exocrine gland, i.e. a gland that discharges its secretion via a duct). The cells can be a pancreatic cell, which can be a pancreatic cell that produces enzymes that are secreted into the small intestine. These enzymes can help digest food as it passes through the gastrointestinal tract. Pancreatic cells can secrete two hormones, insulin and glucagon. A pancreatic cell can be one of several cell types: alpha-2 cells (which can produce the hormone glucagon); or β cells (which can manufacture the hormone insulin); and alpha-1 cells (which can produce the regulatory agent somatostatin). Non-insulin-producing cells can be alpha-2 cells or alpha-1 cells. Pancreatic cells can be pancreatic exocrine cells. Pancreatic cells can be pancreatic endocrine cells, which refer to a pancreatic cell that produces hormones (e.g., insulin (produced from β cells), glucagon (produced by alpha-2 cells), somatostatin (produced by delta cells) and pancreatic polypeptide (produced by F cells) that are secreted into the bloodstream.

The cells disclosed herein can be hormone-secreting cells. The hormone-secreting cells can be alpha cells, beta cells, corticotropic cells, delta cells, gastric chief cells, gonadotropic cells, lactotropic cells, parafollicular cells, parathyroid chief cells, somatomammotrophic cells, somatotropic cells, or thyrotropic cells. In one example, the hormone-secreting cells can be the stem cell-derived beta cells and/or the insulin-secreting cells described in Example 7. In another example, the hormone-secreting cells can be the cells secreting parathyroid hormone, as described in Example 13.

The hormone secreted from the cells can be an amino acid derived hormone (such as epinephrine, melatonin, triiodothyronine, and thyroxine), an eicosanoid (such as prostaglandins, leukotrienes, prostacyclin, and therocis), a peptide hormone (such as amylin, calcitonin, encephalin, erythropoietin, galanin, glucagon, growth hormone, growth hormone-releasing hormone, insulin, pancreatic polypeptide, parathyroid hormone, renin, somatostatin, and vasoactive intestinal peptide), or a steroid (such as androgen, estrogen, glucocorticoid, progestogen, and secosteroid).

The cells disclosed herein can be enzyme-secreting cells. The enzyme-secreting cells can be pancreatic cells. The enzyme-secreting cells can secret protease (such as trypsinogen and chymotrypsinogen), lipase, amylase, phospholipase A2, lysophospholipase, or cholesterol esterase. The enzyme-secreting cells can also secret proenzymes, such as angiotensinogen, trypsinogen, chymotrypsinogen, pepsinogen, fibrinogen, procaspases, pacifastin, proelastase, prolipase, and procarboxypolypeptidases.

Cells can be encapsulated within the membranes (e.g., electrospun polymer membranes) from about $10^4$ to about $10^6$ cells per µl of volume, in which the volume may refer to a luminal volume within a fabricated device. For example, the volume, or luminal volume, may be the amount of cell volume that the device can accommodate. In some instances, cells can be encapsulated within the membranes (e.g., electrospun polymer membranes) from about $4\times10^6$ to about $1\times10^9$ cells per µl. In some instances, cells can be encapsulated within the membranes (e.g., electrospun polymer membranes) from about $4\times10^6$ to about $5\times10^6$, from about $5\times10^6$ to about $6\times10^6$, from about $6\times10^6$ to about $7\times10^6$, from about $7\times10^6$ to about $8\times10^6$, from about $8\times10^6$ to about $9\times10^6$, from about $9\times10^6$ to about $1\times10^7$, from about $1\times10^7$ to about $2\times10^7$, from about $2\times10^7$ to about $3\times10^7$, from about 3×10⁷ to about 4×10⁷, from about 4×10⁷ to about 5×10⁷, from about 5×10⁷ to about 6×10⁷, from about 6×10⁷ to about 7×10⁷, from about 7×10⁷ to about 8×10⁷, from about 8×10⁷ to about 9×10⁷, from about 9×10⁷ to about 1×10⁸, from about 1×10⁸ to about 2×10⁸, from about 2×10⁸ to about 3×10⁸, from about 3×10⁸ to about 4×10⁸, from about 4×10⁸ to about 5×10⁸, from about 5×10⁸ to about 6×10⁸, from about 6×10⁸ to about 7×10⁸, from about 7×10⁸ to about 8×10⁸, from about 8×10⁸ to about 9×10⁸, or from about 9×10⁸ to about 1×10⁹ cells per Drugs. Therapeutic agents that impart a direct therapeutic benefit can include drugs, such as a small molecule, a peptide, a protein, or any combination thereof. These drugs can also be encapsulated as a prodrug, which is metabolized after being released from the crosslinked, functional membranes (e.g., electrospun polymer membranes) into their active therapeutic form. These drugs can include therapeutic agents of varying physiochemical properties including hydrophilic drugs, or any combination thereof. Hydrophobic drugs can be included in the initial polymer solution, which is subsequently electrospun. Hydrophilic drugs can be encapsulated in the form of micronized particulates or is incorporated within the membrane (e.g., electrospun polymer membrane). Drugs can also be conjugated to reactive groups on functional polymers using bioconjugation chemistries. Drugs can be dissolved or suspended in a solvent that is different but miscible with the solvent in which polymers are dissolved prior to electrospinning. Drugs can also be dissolved or suspended in a solvent that is different and not miscible with the solvent in which polymers are dissolved prior to electrospinning. Alternatively, drugs can also be dissolved or suspended in the same solvent as the solvent in which polymers are dissolved prior to electrospinning.

The drug can be present in the membranes (e.g., electrospun polymer membranes) from about 0.01 mg drug/mg polymer to about 0.5 mg drug/mg polymer, from about 0.01 mg drug/mg polymer to about 0.05 mg drug/mg polymer, from about 0.05 mg drug/mg polymer to about 0.1 mg drug/mg polymer, from about 0.1 mg drug/mg polymer to about 0.15 mg drug/mg polymer, from about 0.15 mg drug/mg polymer to about 0.2 mg drug/mg polymer, from about 0.2 mg drug/mg polymer to about 0.25 mg drug/mg polymer, from about 0.25 mg drug/mg polymer to about 0.3 mg drug/mg polymer, from about 0.3 mg drug/mg polymer to about 0.35 mg drug/mg polymer, from about 0.35 mg drug/mg polymer to about 0.4 mg drug/mg polymer, from about 0.4 mg drug/mg polymer to about 0.45 mg drug/mg polymer, or from about 0.45 mg drug/mg polymer to about 0.5 mg drug/mg polymer. For example, the drug can be present in the membrane (e.g., electrospun polymer membrane) from about 0.01 mg drug/mg polymer to about 0.05 mg drug/mg polymer or 0.05 mg drug/mg polymer to 0.1 mg drug/mg polymer. The drug can be less than 10 kDa in molecular weight. Therapeutic agents of the present disclosure can include anti-fibrotic agents, anti-inflammatory agents, pro-vascularizing agents, hydrophilizing agents, antioxidants, macrophage inhibitors, cytotoxic drugs, chemotherapeutic drugs, or any combination thereof. Specific therapeutic agents of the present disclosure can include insulin.

In some embodiments, the drug comprises a recombinant growth factor, a cytokines, an anti-inflammatory agent, a targeted therapy, an adjunct agent, or any combination thereof. In some embodiments, the drug comprises GM-CSF, G-CSF, PDGF, BMP-2, bFGF, VEGF, SDF1, CXCL12, BMP-7, Ghrelin, Tocilizumab, Anti-IL-6R, Infliximab, others, Anti-TNFα, Steroids, Anakinra, IL-1RAntag, Canakinumab, Anti-IL1β, Ixekizumab, Anti-IL17A, Rituximab, Anti-CD20, Ocrelizumab, Abatacept, Belatacept, CTLA4-Ig, Alefacept, LFA3-Ig, Alemtuzumab, Anti-CD52, ATG, Natalizumab, Anti-α4-integrin, Ruxolitinib, Tofacitinib, JAK inhibitors, Resveratrol, Clodronate, GW2580, BLZ945, NPFF, Cilostazol, Pirfenidone, Zafirlukast, Aspirin, Apremilast, Famotidine, Certrizine, Cilostazol, Zafirlukast, Apremilast, Aspirin, or any combination thereof. Drugs can be released from the membrane for at least 3 days, at least 4 days, at least 5 days, at least 6 days, at least 1 week, at least 2 weeks, at least 3 weeks, at least 1 month, at least 2 months, at least 3 months, at least 4 months, at least 5 months, or at least 6 months.

Drug delivery can be achieved through one or more of coating, embedding, and/or encapsulating drugs on/into the membrane (e.g., electrospun polymer membrane). Drug coating can be achieved through incubating the drug with the membrane (e.g., electrospun polymer membrane). In some embodiments, the drug is incubated with the membrane after the electrospinning. In some embodiments, at least one of the fiber and the solvent polarity, pH, ionic strength can enable adsorption of the drug. Drug embedding can be achieved through dissolving drugs in polymer solutions. Drug encapsulation can be achieved through dissolving drugs in polymer solution through a heterogenous processes during the preparation of the polymer solution (e.g. coaxial or emulsion electrospinning of two phase system). In some embodiments, the drug is dissolved in the polymer solution prior to the electrospinning.

Treatment of Disease

The membranes (e.g., electrospun polymer membranes) disclosed herein including the crosslinked, functional membranes (e.g., electrospun polymer membranes) of the present disclosure can be employed to impart a therapeutic benefit to a subject in need thereof. A subject in need thereof can have a condition, such as a chronic disease. Chronic diseases that can be treated with the membranes (e.g., electrospun polymer membranes) disclosed herein can include diabetes. Membranes (e.g., electrospun polymer membranes) can be implanted subcutaneously, in the organ parenchyma, in the peritoneal cavity, or intramuscularly in a subject.

Subjects in need thereof can be a human or a non-human primate. Subjects in need thereof can also be other animals, including mice, rats, rabbits, and pigs. Membranes (e.g., electrospun polymer membranes) can be implanted in a subject in need thereof and can be configured to remain in the user for a period of more 1 day, more than 2 days, more than 3 days, more than 4 days, more than 5 days, more than 6 days, more than 1 week, more than 2 weeks, more than 3 weeks, more than 1 month, more than 2 months, more than 3 months, more than 4 months, more than 5 months, or more than 6 months.

Membranes (e.g., electrospun polymer membranes) disclosed herein can also be used for purposes other than implantation in a subject for a therapeutic benefit. For example, these membranes can be used in filtration devices or material handling or as unloaded cell scaffolds in which cells can be seeded prior to implantation. Other applications can include subretinal implant substrates, wound healing matrices, tissue culture substrates, tissue bulking agents, or bandages.

EXAMPLES

The invention is further illustrated by the following non-limiting examples.

Example 1

Manufacture of Membranes

This example describes the manufacture of membranes (e.g., electrospun polymer membranes). The membrane fabrication process was carried out using a climate controlled electrospinning apparatus (EC-CLI, IME Technologies), consisting of a single emitter with a 19-gauge needle spaced between 5 and 17 cm from a rotating drum collector operating at 500 rpm with a diameter of 6 cm. A polymer solution (6% w/v) was passed through a 0.8 mm PTFE tube into the emitter at 50% humidity and at 23° C. at a flow rate of 16.7 µL/min. The emitter was set between 15 kV and 18 kV, with the collection drum held at −4 kV. After satisfactory fiber formation, the x-axis translational stage of the emitter was set to a repetitive linear pattern at a velocity of 100 mm/s and a 200 ms delay at the edges. The total collection time following activation of the translational stage was 140 min. The membrane (e.g., electrospun polymer membrane) can also be collected on a patterned structure.

The polymer solution includes base polymers, functional polymer, and/or a crosslinking agent. The base polymer includes PAN, PET, PLG, PHEMA, PCL, and/or PLLA. The functional polymer includes PEG, PEGMA, PEGDA, and/or TEGDA. The crosslinking initiator includes a photoinitiator, a heat initiator, and/or transition metals.

Example 2

PAN Membranes of Varying Diameters

This example describes scanning electron microscopy and cumulative release of a protein from PAN membranes (e.g., electrospun polymer membranes) of varying diameters. The membranes (e.g., electrospun polymer membranes) were manufactured according to EXAMPLE 1. PAN polymers were electrospun with a 6% (w/v) PAN polymer solution. Diameters of the filaments in the resulting electrospun polymer membrane were varied by controlling the polymer concentration and voltage. TABLE 1 shows electrospinning parameters, including polymer solution concentration (w/v), positive and negative voltage settings (kV), feed rate, distance, and time of electrospinning, used to obtain 50 µm thick polymer membranes with fiber filaments that are 540 nm, 325 nm, and 202 nm in diameter.

TABLE 1

| | | Electrospinning Parameters | | | | |
|---|---|---|---|---|---|---|
| Sample | Solution | Voltage+ (kV) | Voltage− (kV) | Feed Rate (mL/h) | Distance (cm) | Time (min) |
| 540 nm | 10 wt % | 20 | 5 | 1.25 | 17.5 | 30 |
| 325 nm | 8 wt % | 20 | 5 | 1.25 | 17.5 | 36 |
| 202 nm | 6 wt % | 22 | 5 | 0.7 | 17.5 | 144 |

Electrospun polymer membranes were spun to a thickness of 50 µm. Electrospun membranes were coated with a palladium-gold composite for visualization by scanning electron microscopy (SEM) at 8 kV. Release studies were performed using a Franz cell diffusion apparatus. Briefly, the membrane was mounted between two fluid chambers. FITC-dextran was used as a model drug and a phosphate buffered saline (PBS) buffer was used as the release medium. Aliquots of the release medium were taken at various time points and diffused FITC-dextran was quantified based on fluorescent intensity.

FIG. 1 illustrates an electrospun polymer membrane made of PAN base polymer. FIG. 1A illustrates scanning electron microscopy (SEM) images of PAN base polymer that was electrospun to give filaments of different diameters. The top row shows electrospun polymer membranes at 1500× magnification and the bottom row shows electrospun polymer membranes at 5000× magnification. FIG. 1B illustrates the cumulative release over time of a 4 kDa FITC-dextran molecule in electrospun polymer membranes with a 540 nm filament diameter, a 325 nm filament diameter, and a 202 nm filament diameter.

SEM images show that fibers can be spun to achieve filaments of different diameters. As filament diameter increased, burst release of the 4 kDa FITC-dextran molecule increased.

Example 3

Protein Release from PAN Electrospun Polymer Membranes

This example describes release of different molecular weight proteins from PAN electrospun polymer membranes. Electrospun polymer membranes were manufactured according to EXAMPLE 1. PAN polymers were electrospun in a 6% (w/v) polymer solution. The release study was carried out as described above in EXAMPLE 2.

Figure 2A:
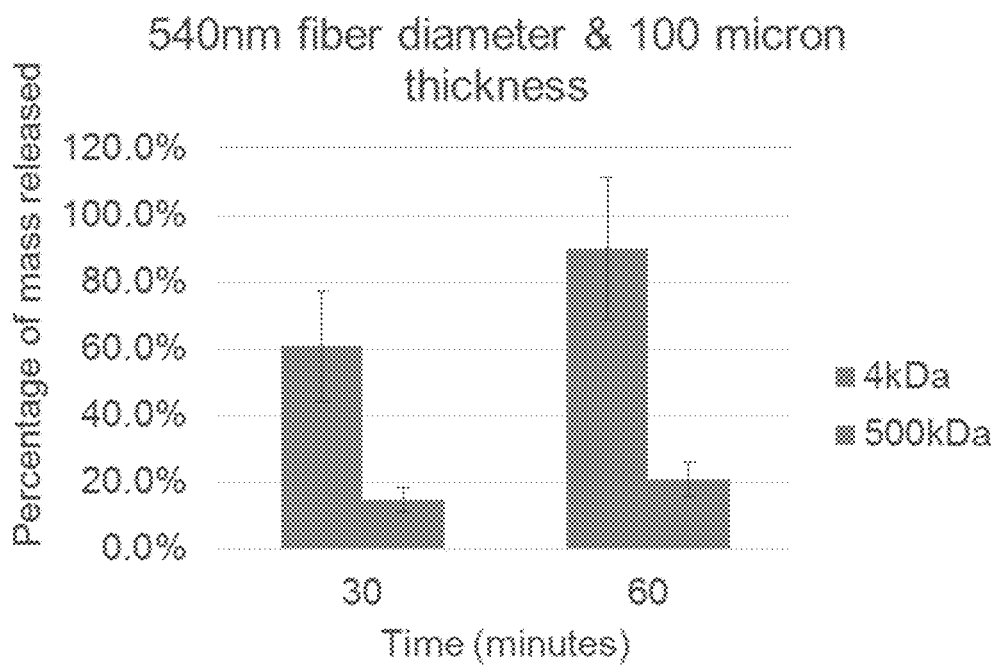
FIG. 2A illustrates diffusion of different molecules out of electrospun polymer membranes having a filament 540 nm in diameter, in accordance with embodiments.
Figure 2B:
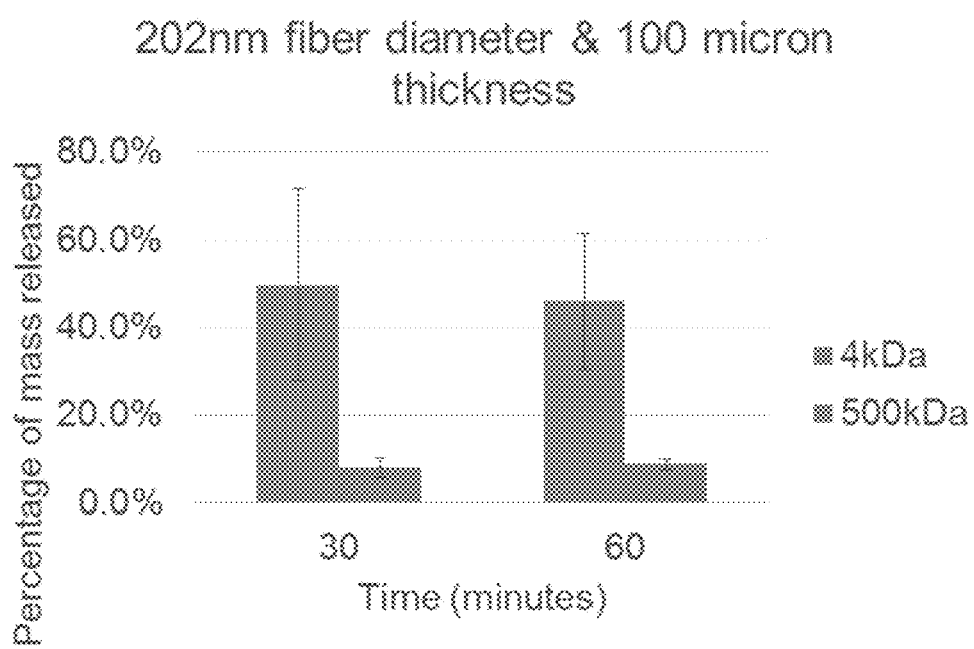
FIG. 2B illustrates diffusion of different molecules out of electrospun polymer membranes having a filament 202 nm in diameter, in accordance with embodiments.
Figure 3B:
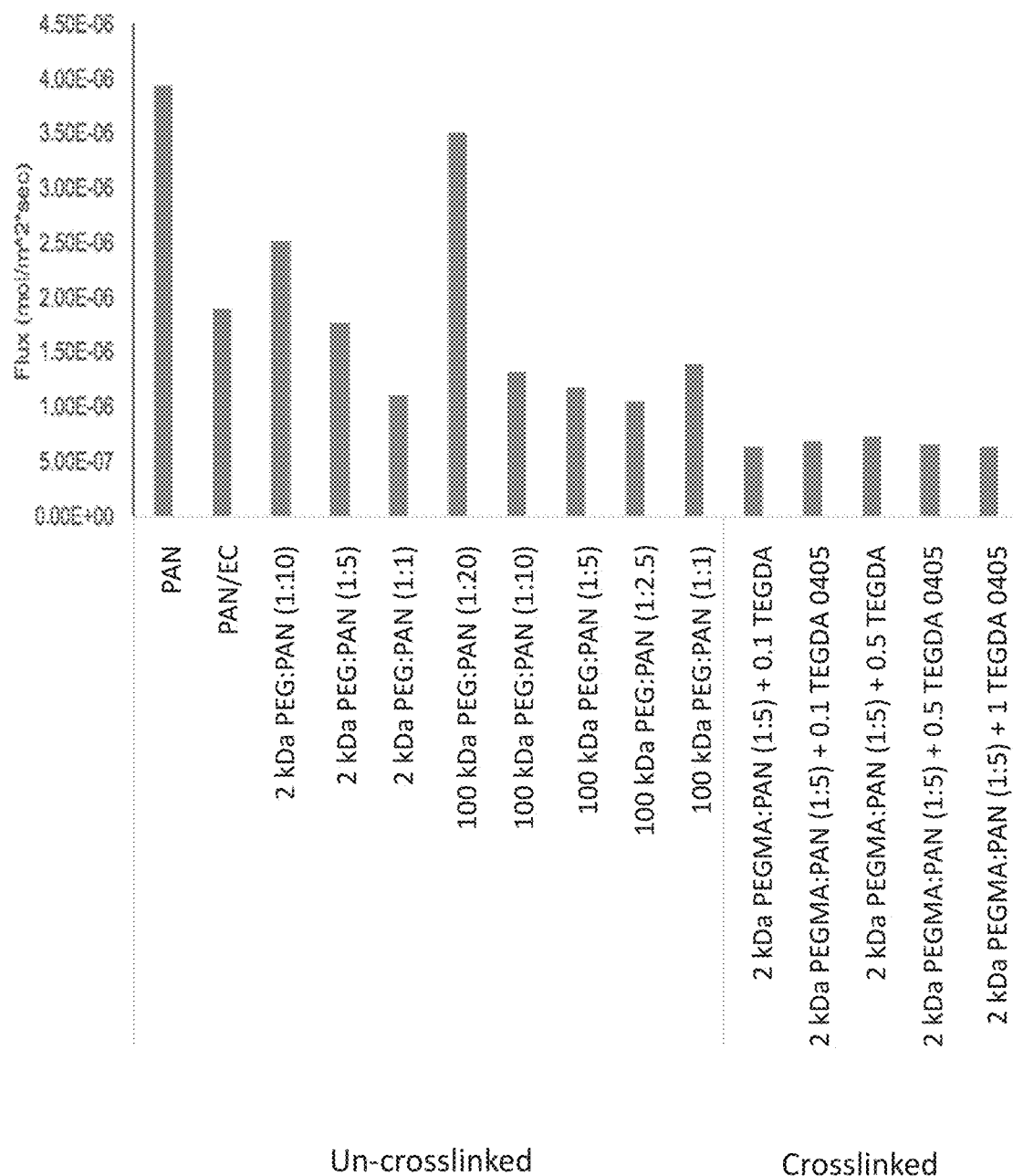
FIG. 3B illustrates the flux of a 4 kDa solute across a range of electrospun polymer membranes both in the uncrosslinked and crosslinked state.

FIG. 2 illustrates diffusion of a 4 kDa FITC-dextran molecule and a 500 kDa FITC-dextran molecule from base polymer blends that were electrospun to give 540 nm filament diameters or 202 nm filament diameters. FIG. 2A illustrates diffusion at 30 min and 60 min of a 4 kDa FITC-dextran molecule and a 500 kDa FITC-dextran molecule from base polymer blends that were electrospun into a 100 micron thick membrane with filaments 540 nm in diameter. FIG. 2B illustrates diffusion at 30 min and 60 min of a 4 kDa FITC-dextran molecule and a 500 kDa X moiety from base polymer blends that were electrospun into a 100 micron thick membrane with filaments 202 nm in diameter. PAN electrospun membranes demonstrated good selectivity in terms of flux of 4 kDa versus 500 kDa molecules. These membranes were permeable to the 4 kDa FITC-dextran, but not quite as permeable to the 500 kDa FITC-dextran. FIG. 3 illustrates diffusion coefficients of 4 kDa and 500 kDa moieties in various polymer membranes and the flux of a 4 kDa moiety in uncrosslinked and crosslinked electrospun polymer membranes of the present disclosure. FIG. 3A illustrates the diffusion coefficient of an electrospun polymer membranes fabricated from poly(acrylonitrile)(PAN) compared to a Biopore ePTFE membrane, in accordance with embodiments. In comparison to commercially available membranes (Biopore ePTFE), the high flux electrospun polymer membrane of this example exhibits especially high flux of the 4 kDa protein, while restricting diffusion of the 150 kDa protein. FIG. 3B illustrates the flux of the 4 kDa FITC-dextran in a range of uncrosslinked and crosslinked electrospun membranes, which were synthesized using the methods set forth in EXAMPLE 1 and EXAMPLE 2.

Example 4

Histological Analysis of Electrospun Polymer Membranes Implanted in Mice

This example describes histological analysis of electrospun polymer membranes implanted in mice. PAN electrospun polymer membranes were manufactured according to EXAMPLE 1. PAN polymers were dissolved in a 6% (w/v) polymer solution and electrospun as described in EXAMPLE 2. Electrospun polymer membranes were implanted into the epidydimal fat pad of NOD scid gamma (NSG) mice for 60 days. Mice were euthanized, tissues containing the electrospun polymer membrane were necropsied and section, and stained with hematoxylin and eosin (H&E).

Figure 4A:
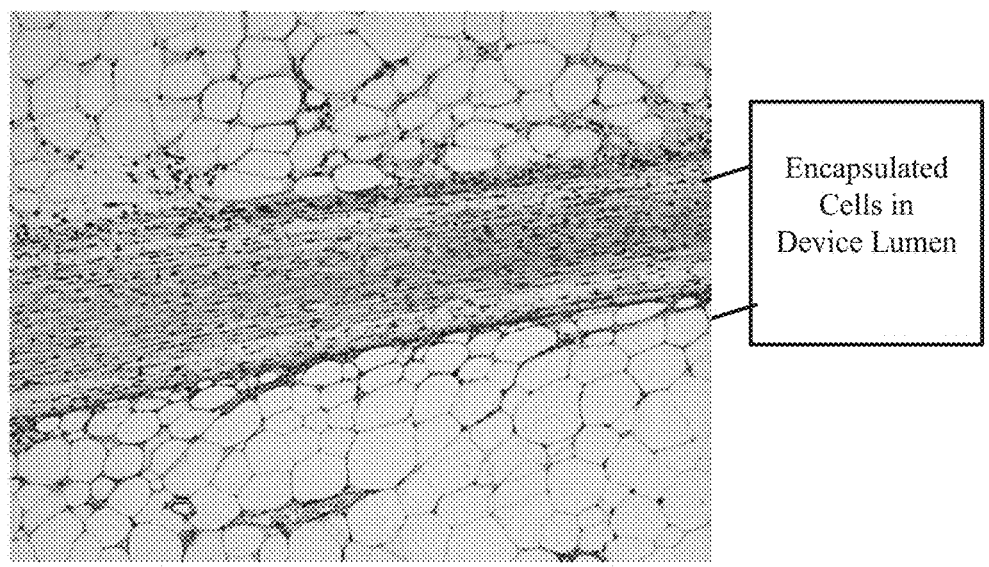
FIG. 4A illustrates the epididymal fat pad of a mouse implanted with the cell-loaded, planar device constructed from electrospun polymer membrane, in accordance with embodiments.
Figure 4B:
FIG. 4B illustrates the ingress of host cells into the wall of the electrospun polymer membrane after being implanted into the epididymal fat pad of a mouse, in accordance with embodiments.

FIG. 4 illustrates photomicrographs of hematoxylin and eosin (H&E) stained tissue section from mice implanted in the epididymal fat pad with the cell-loaded, PAN electrospun polymer membranes of the present disclosure. FIG. 4A illustrates the epididymal fat pad of a mouse implanted with the cell-loaded, planar device construction from an electrospun polymer membrane. FIG. 4B illustrates the ingress of host cells into the wall of the electrospun polymer membrane after being implanted into the epididymal fat pad of a mouse. These studies showed that cells encapsulated in the membrane were capable of diffusing out of the polymer network. These results demonstrated that electrospun polymer membranes can be designed to allow for cellular migration. Electrospun polymer membranes can also be designed to prevent cellular migration, for example, by crosslinking functional electrospun polymers.

Example 5

Mechanical Strength of Electrospun Polymer Membranes

This example describes the mechanical strength of electrospun polymer membranes. Electrospun polymer membranes were manufactured according to EXAMPLE 1. Various formulations of ethylene carbonate:PAN, and PAN:PEG were electrospun in a 6% (w/v) polymer solutions. Tensile properties were measured by stretching a strip of a given size membrane under a controlled manner.

Figure 5:
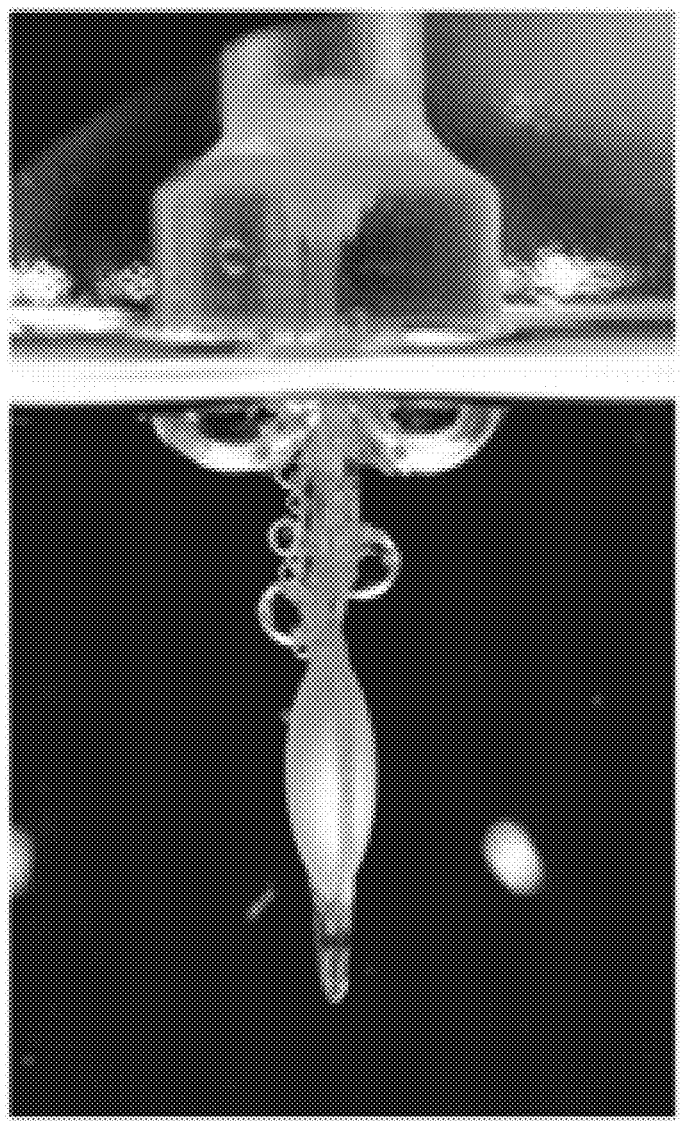
FIG. 5 illustrates the test system used to measure the burst strength of planar devices fabricated from electrospun polymer membranes.

FIG. 5 illustrates the test system used to measure the burst strength of planar devices fabricated from electrospun polymer membranes. FIG. 6 illustrates a burst analysis of various electrospun polymer membranes of the present disclosure. FIG. 6A illustrates the pressure (psi) at which electrospun polymer membranes burst for the following electrospun polymer membrane compositions: 1% ethylene carbonate:PAN, 1:1 PEG:PAN, 1:2.5 PEG:PAN, 1:5 PEG:PAN, and 1:10 PEG:PAN. FIG. 6B illustrates the maximum load (mN) as measured per ASTM D790-03 using a Flexion instrument withstood by electrospun polymer membranes for the following electrospun polymer membrane compositions: 1:1 PEG:PAN, 1:2.5 PEG:PAN, 1:5 PEG:PAN, and 1:10 PEG:PAN. Maximum load mechanical tests were conducted using ASTM D790 methods. The 1:10 PEG:PAN electrospun polymer membrane withstood the highest burst pressure and highest maximum load as compared to the 1% ethylene carbonate:PA membrane and other tested PAN:PEG electrospun polymer membranes.

Example 6

Manufacture and Testing of Crosslinked, Functional Electrospun Polymer Membranes This example describes the manufacture and testing of crosslinked, functional electrospun polymer membranes of this disclosure. Electrospun polymer membranes were manufactured according to EXAMPLE 1. PEGMA:PAN polymers were electrospun with a 1:1 to 1:10 ratio of PEGMA:PAN in a 6% (w/v) polymer solution. Preparation of membranes for SEM and release studies are described above in EXAMPLE 2. Separately, PAN:PEGMA polymers were electrospun in a 6% (w/v) polymer solution with 2% TEGDA. After electrospun polymer membranes were collected, membranes were irradiated under a UV light to initiate crosslinking to obtain crosslinked, functional electrospun polymer membranes. UV exposure was carried out using a UV crosslinker, which is an enclosed chamber with a UV lamp shining from above. Photoinitiator is present at a concentration of 1% and UV exposure is carried out for 10 minutes.

FIG. 7 illustrates crosslinked, functional, electrospun polymer membranes of the present disclosure. FIG. 7A illustrates an SEM image of a non-crosslinked, electrospun polymer membrane consisting of a 1:5 ratio of PEGMA (2 kDa):PAN (150 kDa). FIG. 7A shows the same electrospun membranes as in FIG. 7B, but were not UV-crosslinked. FIG. 7B illustrates an SEM image of a UV-crosslinked, electrospun polymer membrane consisting of a 1:5 ratio of PEGMA (2 kDa):PAN (150 kDa), in which 2% TEGDA was introduced at the UV crosslinking stage. Electrospun membranes were soaked in a solution of 2% TEGDA and dimethoxyacetophenone, which is a UV-initiator, and exposed to UV light for crosslinking. FIG. 7C shows cumulative release over time of a 4 kDa FITC-dextran molecule from electrospun polymer membranes of the present disclosure including a 1:10 PEGMA (2 kDa):PAN (150 kDa), a 1:5 PEGMA (2 kDa):PAN (150 kDa), a 1:10 PEGMA (2 kDa):PAN (150 kDa) with 2% TEGDA (0.3 kDa), and a 1:10 PEGMA (2 kDa):PAN (150 kDa) with 2% TEGDA (0.3 kDa). SEM images confirmed the change in ultrastructure of the polymer network post crosslinking. For example, porosity was visually observed in SEM image to reduce after crosslinking. Release experiments showed that an increase in the amount of PEGMA in an electrospun polymer membrane (1:10 PEGMA:PAN) dampened burst release of the 4 kDa FITC-dextran molecule from electrospun polymer membranes. Release experiments also showed that crosslinking of the electrospun polymer membrane further dampened burst release of the 4 kDa FITC-dextran molecule from electrospun polymer membranes.

Attenuated total reflection-FTIR (ATR-FTIR) was employed with 32 scans. FIG. 8 illustrates crosslinking of base and functional polymers after electrospinning. FIG. 8A illustrates that PEGMA itself can be UV-crosslinked with a photoinitiator to provide a functional, electrospun polymer membrane. Alternatively, PEGMA can be UV-crosslinked with a crosslinker, TEGDA, to obtain a crosslinked, functional electrospun polymer membrane. FIG. 8B illustrates Fourier transform infrared spectroscopy (FTIR) results showing the transition from C=C bonds to C—C bonds in the PEGMA polymer upon crosslinking. These results confirmed that chemical crosslinking did occur in UV-exposed, crosslinked, functional electrospun polymer membranes.

Tensile strength and Young's modulus values were measured using an Instron Tensile with an ASTM-882 02 Standard Test Method for Tensile Properties of Plastics. Release studies were carried out as described above in EXAMPLE 2. FIG. 9 illustrates the tensile properties and permeability of crosslinked, functional, electrospun polymer membranes. FIG. 9A illustrates the tensile strength (MPa) of 1:5 PEGMA (2 kDa):PAN (150 kDa) without TEGDA and with 2% (w/v) TEGDA and 1:5 PEGMA (480 Da):PAN (150 kDa) without TEGDA and with 2% (w/v) TEGDA. FIG. 9B illustrates the Young's modulus (MPa) of 1:5 PEGMA (2 kDa):PAN (150 kDa) without TEGDA and with 2% (w/v) TEGDA and 1:5 PEGMA (480 Da):PAN (150 kDa) without TEGDA and with 2% (w/v) TEGDA. FIG. 9C illustrates the cumulative release of a 4 kDa FITC-dextran molecule over time for various formulations of 150 kDa PAN and 2 kDa or 480 Da PEGMA in crosslinked electrospun membranes, with and without 2% (w/v) TEGDA.

Tensile strength increased in crosslinked, functional electrospun polymer membranes with TEGDA and were roughly the same for both 1:5 PAN (150 kDa):PEGMA (2 kDa) and 1:5 PAN (150 kDa):PEGMA (480 Da). Without the TEGDA crosslinker, PAN:PEGMA electrospun polymer membranes decreased in tensile strength as the molecular weight of PEGMA was reduced. The Young's modulus very slightly increased in crosslinked, functional electrospun polymer membranes with TEGDA in the 1:5 PAN (150 kDa): PEGMA (2 kDa) and the Young's modulus significant increase in crosslinked, functional electrospun polymer membranes with TEGDA in the 1:5 PAN (150 kDa): PEGMA (480 Da). Without the TEGDA crosslinker, PAN: PEGMA electrospun polymer membranes decreased in Young's modulus as the molecular weight of PEGMA was reduced. Release experiments showed that inclusion of TEGDA crosslinker in crosslinked, functional electrospun polymer membrane dampened release of the 4 kDa FITC-dextran. An increase in the amount of PEGMA in electrospun polymer membranes without TEGDA increased release of the FITC-dextran. In TEGDA crosslinked, functional electrospun polymer membranes, a decrease in the molecular weight of PEGMA dampened release of the FITC-dextran.

FIG. 10 illustrates SEM images showing the ultrastructure of functional, electrospun polymer membranes after UV-crosslinking without and with 2% (w/v) TEGDA. Electrospun polymer membranes were composed of 1:5 PEGMA (2 kDa):PAN (150 kDa) and 1:5 PEGMA (480 Da)PAN (150 kDa). SEM images show the change in the overcoating after crosslinking in electrospun polymer membranes without TEGDA and with 2% TEGDA. Porosity was observed visually in SEM images to be smaller in size for the membrane containing the 480 Da PEGMA and crosslinked with 2% TEGDA.

Example 7

Insulin-Secreting Cell Delivery in Crosslinked, Functional Electrospun Polymer Membranes This example describes delivery of insulin-secreting cells in crosslinked, functional electrospun polymer membranes. Membranes (e.g., electrospun polymer membranes) are manufactured according to EXAMPLE 1. Base polymers, crosslinker, and photoinitiator are electrospun using techniques to obtain a functional electrospun polymer membrane of suitable thickness. Base polymers include PAN and PEGMA, crosslinker includes TEGDA, and photoinitiator includes dimethoxyacetophenone Base polymers, crosslinker, and photoinitator can also be any of the polymers and compounds described herein. Functional electrospun polymer membranes are crosslinked with UV light to obtain crosslinked, functional electrospun polymer membranes. Cells are loaded in crosslinked, functional electrospun polymer membrane by incorporation in the polymer solution prior to electrospinning or seeded on crosslinked, functional electrospun polymer membranes. Cells are stem cells, such as stem cell-derived beta cells engineered to express insulin.

Example 8

Drug Delivery in Crosslinked, Functional Electrospun Polymer Membranes

This example describes delivery of drug in crosslinked, functional electrospun polymer membranes. Electrospun polymer membranes are manufactured according to EXAMPLE 1. Base polymers, crosslinker, and photoinitiator are electrospun using techniques to obtain a functional electrospun polymer membrane of suitable thickness. Base polymers include PAN and PEGMA, crosslinker includes TEGDA, and photoinitiator includes dimethoxyacetophenone. Base polymers, crosslinker, and photoinitator can also be any of the polymers and compounds described herein. Functional electrospun polymer membranes are crosslinked with UV light to obtain crosslinked, functional electrospun polymer membranes. Drug is loaded in crosslinked, functional electrospun polymer membrane by incorporation in the polymer solution prior to electrospinning or seeded on crosslinked, functional electrospun polymer membranes. Drugs include small molecules, such as hydrophobic drugs or hydrophilic drugs, or biologics, such as peptides or proteins. Specific drugs include immune response suppressors or oxygen generating reagents.

Example 9

Treatment of Diabetes

This example describes treatment of diabetes in a subject in need thereof. Any crosslinked, functional electrospun polymer membrane of the present disclosure is manufactured according to EXAMPLE 1. Cells or drugs are loaded in the crosslinked, functional electrospun polymer membrane as described in EXAMPLE 7 and EXAMPLE 8. Cells are stem cell-derived beta cells engineered to express insulin. The drug is insulin protein. These cell or drug-loaded, crosslinked, functional electrospun polymer membrane is implanted into a subject in need thereof. The subject is any animal, such as a mouse, a rat, a rabbit, a non-human primate, or a human. The subject in need thereof has a condition. The condition is diabetes. Upon implantation of the membranes, the diabetes condition is ameliorated. The membrane manages the diabetes condition by release of insulin for up to 6-36 months.

Example 10

Manufacture of Electrospun Polymer Membranes with Parallel Filaments

This example describes the manufacture of functional electrospun polymers with parallel filaments. The electrospinning membrane fabrication process was carried out using a climate controlled electrospinning apparatus (EC-CLI, IME Technologies), consisting of a single emitter with a 19-gauge needle spaced between 5 and 17 cm from a rotating drum collector operating at 500 rpm with a diameter of 6 cm. A polymer solution (6% w/v) was passed through a 0.8 mm PTFE tube into the emitter at 50% humidity and at 23° C. at a flow rate of 16.7 µL/min. The emitter was set between 15 kV and 18 kV, with the collection drum held at −4 kV. After satisfactory fiber formation, the x-axis translational stage of the emitter was set to a repetitive linear pattern at a velocity of 100 mm/s and a 200 ms delay at the edges. The total collection time following activation of the translational stage was 140 min. The electrospun polymer membrane can also be collected on a patterned structure.

The polymer solution includes base polymers, functional polymer, and/or a crosslinking agent. The base polymer includes PAN, PET, PLG, PHEMA, PCL, and/or PLLA. The functional polymer includes PEG, PEGMA, PEGDA, and/or TEGDA. The crosslinking initiator includes a photoinitiator, a heat initiator, and/or transition metals.

Parallel filament formation will ensured by measuring the angle of a representative sample of filaments in the electrospun membrane with reference to the y-axis orientation by scanning electron microscopy. This is conducted with a sample size of at least 100 filaments at a magnification of 1,000×.

Example 11

Cell Delivery in Crosslinked, Functional Electrospun Polymer Membranes

This example describes delivery of cells in crosslinked, functional electrospun polymer membranes. Electrospun polymer membranes are manufactured according to EXAMPLE 1. Base polymers, crosslinker, and photoinitiator are electrospun using techniques to obtain a functional electrospun polymer membrane of suitable thickness. Base polymers include PAN and PEGMA, crosslinker includes TEGDA, and photoinitiator includes dimethoxyacetophenone Base polymers, crosslinker, and photoinitator can also be any of the polymers and compounds described herein. Functional electrospun polymer membranes are crosslinked with UV light to obtain crosslinked, functional electrospun polymer membranes. Cells are loaded in crosslinked, functional electrospun polymer membrane by incorporation in the polymer solution prior to electrospinning or seeded on crosslinked, functional electrospun polymer membranes. Cells are parathyroid cells, retinal pigmented epithelium, or cardiomyocytes.

Example 12

Treatment of Ischemic Wounds

This example describes treatment of ischemic wounds in a subject in need thereof. Any crosslinked, functional electrospun polymer membrane of the present disclosure is manufactured according to EXAMPLE 1. Cells or drugs are loaded in the crosslinked, functional electrospun polymer membrane as described in EXAMPLE 7 and EXAMPLE 8. Cells are engineered to express an appropriate drug to treat ischemic wounds, such as platelet-derived growth factor (PDGF), connective tissue growth factor (CTGF), hepatocyte growth factor (HGF), stem cell factor (SCF), insulin-like growth factor (IGF-I), transforming growth factor beta-1 (TGF-B1), and others. These cell or drug-loaded, crosslinked, functional electrospun polymer membrane is implanted into a subject in need thereof. The subject is any animal, such as a mouse, a rat, a rabbit, a non-human primate, or a human. The subject in need thereof has a condition. The condition is ischemic wounds. Upon implantation of the membranes, the ischemic wounds condition is ameliorated.

Example 13

Treatment of Hypoparathyroidism

This example describes treatment of hypoparathyroidism in a subject in need thereof. Any crosslinked, functional electrospun polymer membrane of the present disclosure is manufactured according to EXAMPLE 1. Cells or drugs are loaded in the crosslinked, functional electrospun polymer membrane as described in EXAMPLE 7 and EXAMPLE 8. Cells are engineered to express or secrete an appropriate drug to treat hypoparathyroidism, namely parathyroid hormone. These cell or drug-loaded, crosslinked, functional electrospun polymer membrane is implanted into a subject in need thereof. The subject is any animal, such as a mouse, a rat, a rabbit, a non-human primate, or a human. The subject in need thereof has a condition. The condition is hypoparathyroidism. Upon implantation of the membranes, the hypoparathyroidism condition is ameliorated.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An implantable device comprising:
a porous polymeric membrane including a plurality of open pores, wherein the open pores have an average pore size equal to or less than 1 µm, wherein said membrane has an average thickness of between 10 µm and 150 µm, and wherein said membrane has a tensile strength of at least 1 MPa; and
a population of cells, wherein said population of cells comprises at least one selected from the group of pancreatic progenitor cells, endocrine cells, alpha cells, delta cells, and beta cells, wherein said membrane is configured to exhibit a ratio of $D_{first}/D_{second}$ equal to or greater than 2 and less than or equal to 50, wherein $D_{first}$ is a first diffusion coefficient for a first molecule having a first molecular weight between or equal to 50 Da and 10 kDa, wherein $D_{second}$ is a second diffusion coefficient for a second molecule having a second molecular weight between or equal to 50 kDa and 500 kDa, and wherein a ratio of said second molecular weight to said first molecular weight is equal to or greater than 10.

2. The device of claim 1, wherein the membrane at least partially encapsulates said population of cells.

3. The device of claim 2, wherein said population of cells is encapsulated within said device in an amount of $10^4$ to $10^6$ cells per µL.

4. The device of claim 1, wherein said device is configured to produce and release insulin when implanted into a subject.

5. The device of claim 1, wherein said first molecule is 4 kDa FITC-dextran, and said second molecule is 500 kDa FITC-dextran.

6. The device of claim 1, wherein said second molecule comprises at least one selected from the group of pepsinogen, lipase 2, prolipase, angiotensinogen, amylase, and cholesterol esterase.

7. The device of claim 1, wherein said cell population comprises non-native beta cells.

8. The device of claim 7, wherein said non-native beta cells exhibit a glucose-stimulated insulin secretion (GSIS) response to an in vitro glucose challenge.

9. The device of claim 1, wherein said membrane is an electrospun polymer membrane.

10. The device of claim 1, wherein the membrane comprises polymers having a molecular weight of less than or equal to 1,500,000 Da.

11. The device of claim 1, wherein the membrane comprises polyacrylonitrile (PAN), polysulfone (PSf), polytetrafluoroethylene (PTFE), polyurethane (PU), polyvinylidene fluoride (PVDF), or any combination thereof.

12. The device of claim 1, wherein the membrane comprises polytetrafluoroethylene (PTFE).

13. The device of claim 1, wherein the membrane has a Young's Modulus of at least 60 MPa.

14. The device of claim 1, wherein the population of cells is a population of human cells.

15. The device of claim 1, wherein the plurality of open pores comprises pores that are substantially open.

16. The device of claim 1, wherein the membrane has a thickness of between 10 µm and 20 µm.

17. The device of claim 1, wherein the membrane has a thickness of between 20 µm and 30 µm.

18. An implantable device comprising:
a porous polymeric membrane including a plurality of open pores;
a population of human cells within said membrane, wherein said membrane is configured to at least partially encapsulate said population of human cells, wherein said population of human cells comprises at least one selected from the group of human pancreatic progenitor cells, human endocrine cells, human alpha cells, human delta cells, and human beta cells, wherein said membrane has:
an average pore size equal to or less than 1 µm; and
an average thickness equal to or less than of between 10 µm and 150 µm; wherein said membrane is configured to exhibit a ratio of $D_{first}/D_{second}$ equal to or greater than 2 and less than or equal to 50, wherein $D_{first}$ is a first diffusion coefficient for a first molecule having a first molecular weight between or equal to 50 Da and 10 kDa, wherein $D_{second}$ is a second diffusion coefficient for a second molecule having a second molecular weight between or equal to 50 kDa and 500 kDa, and wherein a ratio of said second molecular weight to said first molecular weight is equal to or greater than 10.

19. The device of claim 18, wherein said membrane has an average fiber diameter of equal to or less than 1000 nm.

20. The device of claim 18, wherein said membrane is an electrospun polymer membrane.

21. The device of claim 18, wherein said membrane has a molecular weight of at least 400 Da.

22. The device of claim 18, wherein $D_{first}$ is equal to or greater than $10^{-7}$ cm$^2$/sec.

23. The implantable device of claim 18, wherein said population of cells comprises at least one insulin producing cell and at least one glucagon or somatostatin producing cell, and wherein said device, when implanted into a subject, releases said insulin at a different flux rate than said device releases said glucagon or said somatostatin.

24. The device of claim 18, wherein said population of cells comprises non-native beta cells.

25. The device of claim 24, wherein said non-native beta cells exhibit a glucose-stimulated insulin secretion (GSIS) response to an in vitro glucose challenge.

26. The device of claim 18, wherein said first molecule is 4 kDa FITC-dextran, and said second molecule is 500 kDa FITC-dextran.

27. The device of claim 18, wherein the membrane comprises polymers having a molecular weight of less than or equal to 1,500,000 Da.

28. The device of claim 18, wherein the membrane comprises polyacrylonitrile (PAN), polysulfone (PSf), polytetrafluoroethylene (PTFE), polyurethane (PU), polyvinylidene fluoride (PVDF), or any combination thereof.

29. The device of claim 18, wherein the membrane comprises polytetrafluoroethylene (PTFE).

30. The device of claim 18, wherein the plurality of open pores comprises pores that are substantially open.

31. An implantable device comprising:
a porous crosslinked electrospun polymeric membrane configured to encapsulate a population of cells, wherein the membrane includes a plurality of open pores, wherein the membrane has:
an average pore size equal to or less than 1 µm,
an average thickness of between 10 µm and 150 µm; and
an average fiber diameter of equal to or less than 1000 nm;
wherein the membrane is hydrophilic,
wherein said membrane is configured to exhibit a ratio of $D_{first}/D_{second}$ equal to or greater than 2 and less than or equal to 50, wherein $D_{first}$ is a first diffusion coefficient for a first molecule having a first molecular weight between or equal to 50 Da and 10 kDa, wherein $D_{second}$ is a second diffusion coefficient for a second molecule having a second molecular weight between or equal to 50 kDa and 500 kDa, and wherein a ratio of said second molecular weight to said first molecular weight is equal to or greater than 10.

32. The device of claim 31, wherein said first molecule is 4 kDa FITC-dextran, and said second molecule is 500 kDa FITC-dextran.

33. The device of claim 31, wherein the membrane comprises polyacrylonitrile (PAN), polysulfone (PSf), polytetrafluoroethylene (PTFE), polyurethane (PU), polyvinylidene fluoride (PVDF), or any combination thereof.

34. The device of claim 31, wherein the membrane comprises polytetrafluoroethylene (PTFE).

35. The device of claim 31, further comprising the population of cells, wherein the population of cells includes at least one selected from the group of pancreatic progenitor cells, endocrine cells, alpha cells, delta cells, and beta cells.

36. The device of claim 31, wherein the plurality of open pores comprises pores that are substantially open.

* * * * *